US 11,969,557 B1

(12) United States Patent
English

(10) Patent No.: US 11,969,557 B1
(45) Date of Patent: Apr. 30, 2024

(54) WEARABLE DEVICES FOR PROVIDING PRESSURE THERAPY TO A USER

(71) Applicant: New Heights Energy, LLC, Williamston, MI (US)

(72) Inventor: Trent K. English, Williamston, MI (US)

(73) Assignee: New Heights Energy, LLC, Williamston, MI (US)

( * ) Notice: Subject to any disclaimer, the term of this patent is extended or adjusted under 35 U.S.C. 154(b) by 0 days.

(21) Appl. No.: 18/404,002

(22) Filed: Jan. 4, 2024

Related U.S. Application Data

(60) Continuation of application No. 17/941,056, filed on Sep. 9, 2022, which is a division of application No. 16/984,222, filed on Aug. 4, 2020, now Pat. No. 11,478,606.

(60) Provisional application No. 63/043,471, filed on Jun. 24, 2020, provisional application No. 62/958,383, filed on Jan. 8, 2020.

(51) Int. Cl.
*A61M 21/02* (2006.01)
*A61M 21/00* (2006.01)

(52) U.S. Cl.
CPC ..... *A61M 21/02* (2013.01); *A61M 2021/0022* (2013.01); *A61M 2210/083* (2013.01); *A61M 2230/06* (2013.01); *A61M 2230/205* (2013.01)

(58) Field of Classification Search
None
See application file for complete search history.

(56) References Cited

U.S. PATENT DOCUMENTS

| | | | |
|---|---|---|---|
| 4,728,934 | A | 3/1988 | Pfander et al. |
| 5,097,828 | A | 3/1992 | Deutsch |
| 5,575,761 | A | 11/1996 | Hajianpour |
| 6,076,018 | A | 6/2000 | Sturman et al. |
| 6,155,995 | A | 12/2000 | Lin |
| 6,228,103 | B1 | 5/2001 | Grey et al. |
| 6,567,695 | B1 | 5/2003 | Gruzdowich et al. |
| 6,918,879 | B2 | 7/2005 | Ting et al. |
| 7,127,288 | B2 | 10/2006 | Sturman et al. |
| 7,241,303 | B2 | 7/2007 | Reiss et al. |
| 7,293,383 | B2 | 11/2007 | Fishman et al. |
| 7,544,168 | B2 | 6/2009 | Nitzan |
| 7,637,878 | B2 | 12/2009 | Lin |
| 7,755,602 | B2 | 7/2010 | Tremblay et al. |

(Continued)

FOREIGN PATENT DOCUMENTS

| | | |
|---|---|---|
| CN | 103284874 A | 9/2013 |
| CN | 106333667 A | 1/2017 |

(Continued)

OTHER PUBLICATIONS

Waveforms published at least before Jan. 8, 2020; 1 page <https://vault.netvoyage.com/neWeb2/goid.aspx?id=4839-7611-9493>.

(Continued)

*Primary Examiner* — Thaddeus B Cox
(74) *Attorney, Agent, or Firm* — Howard & Howard Attorneys PLLC

(57) ABSTRACT

Wearable devices can be used to provide therapy to users and/or to monitor various physiological parameters of the user. In some cases, therapy can be triggered automatically based on the monitored physiological parameters reaching or exceeding predefined thresholds.

20 Claims, 53 Drawing Sheets

(56) References Cited

U.S. PATENT DOCUMENTS

| | | |
|---|---|---|
| 7,763,046 B2 | 7/2010 | Schouten et al. |
| 8,086,301 B2 | 12/2011 | Cho et al. |
| 8,585,605 B2 | 11/2013 | Caros et al. |
| 8,668,045 B2 | 3/2014 | Cohen |
| 8,787,006 B2 | 7/2014 | Golko et al. |
| 8,944,958 B1 | 2/2015 | Brumback et al. |
| 9,042,971 B2 | 5/2015 | Brumback et al. |
| 9,049,998 B2 | 6/2015 | Brumback et al. |
| 9,307,906 B2 | 4/2016 | Harte et al. |
| 9,320,676 B2 | 4/2016 | Chou |
| 9,600,994 B2 | 3/2017 | Park et al. |
| 9,655,548 B2 | 5/2017 | Hong et al. |
| 9,675,782 B2 | 6/2017 | Connolly |
| 9,730,591 B2 | 8/2017 | Ahmed et al. |
| 9,884,164 B2 | 2/2018 | Tass |
| 9,886,093 B2 | 2/2018 | Moussette et al. |
| 10,058,148 B1 | 8/2018 | Wittenberg et al. |
| 10,076,662 B2 | 9/2018 | Tuan |
| 10,092,224 B2 | 10/2018 | Chowdhury |
| 10,191,550 B1 | 1/2019 | Nussbaum et al. |
| 10,216,894 B2 | 2/2019 | Hong et al. |
| 10,238,575 B2 | 3/2019 | Darna |
| 10,258,117 B2 | 4/2019 | Graber et al. |
| 10,448,711 B2 | 10/2019 | Kallman et al. |
| 10,487,127 B2 | 11/2019 | Stimson |
| 10,497,246 B2 | 12/2019 | Arnold et al. |
| 10,512,407 B2 | 12/2019 | Richards et al. |
| 10,532,181 B2 | 1/2020 | Hooper et al. |
| 10,627,861 B2 | 4/2020 | Connor |
| 10,702,171 B2 | 7/2020 | Narasimhan et al. |
| 10,735,831 B2 | 8/2020 | Dixit |
| 10,758,451 B1 | 9/2020 | McDevitt et al. |
| 10,772,394 B1 | 9/2020 | Michalske |
| 10,786,666 B2 | 9/2020 | Chu et al. |
| 10,849,822 B2 | 12/2020 | Zhang et al. |
| 10,854,103 B2 | 12/2020 | O'Dowd et al. |
| 10,881,307 B1 | 1/2021 | Sullivan et al. |
| 10,925,541 B2 | 2/2021 | Tokko et al. |
| 10,974,019 B2 | 4/2021 | Sunnen et al. |
| 10,993,872 B2 | 5/2021 | Novich et al. |
| 10,993,874 B1 | 5/2021 | Marton et al. |
| 11,000,437 B2 | 5/2021 | Mayo et al. |
| 11,031,117 B2 | 6/2021 | Mayo et al. |
| 11,033,708 B2 | 6/2021 | Blahnik et al. |
| 11,033,709 B2 | 6/2021 | Mayo et al. |
| 11,079,851 B2 | 8/2021 | Eagleman et al. |
| 11,079,854 B2 | 8/2021 | Eagleman et al. |
| 11,092,999 B2 | 8/2021 | Fu et al. |
| 11,185,237 B2 | 11/2021 | Peters et al. |
| 11,260,198 B2 | 3/2022 | Rabin et al. |
| D963,189 S | 9/2022 | Qiao |
| 11,602,454 B1 | 3/2023 | Aguiar et al. |
| 11,730,916 B1 | 8/2023 | Hill |
| 2002/0156502 A1 | 10/2002 | Tuan |
| 2003/0130690 A1 | 7/2003 | Porrata et al. |
| 2004/0044384 A1 | 3/2004 | Leber et al. |
| 2004/0098037 A1 | 5/2004 | Grey et al. |
| 2005/0209504 A1 | 9/2005 | Elliott |
| 2007/0088234 A1 | 4/2007 | Tseng |
| 2007/0088385 A1 | 4/2007 | Perry |
| 2007/0100262 A1 | 5/2007 | Simos et al. |
| 2008/0027363 A1 | 1/2008 | Brueckmann et al. |
| 2008/0195006 A1 | 8/2008 | Stark et al. |
| 2009/0177129 A1 | 7/2009 | Chan et al. |
| 2011/0178360 A1 | 7/2011 | Gavish et al. |
| 2011/0313239 A1 | 12/2011 | Ahne |
| 2012/0316480 A1* | 12/2012 | Nolan .................. A61F 13/085 |
| | | 601/151 |
| 2012/0323149 A1 | 12/2012 | Chou |
| 2013/0123570 A1* | 5/2013 | Ly ........................ A61M 21/02 |
| | | 600/27 |
| 2013/0184623 A1* | 7/2013 | Fraser .................. A61H 9/0078 |
| | | 601/151 |
| 2013/0218197 A1 | 8/2013 | Tarumi |
| 2015/0049591 A1 | 2/2015 | Adams et al. |
| 2015/0190607 A1 | 7/2015 | Sugio et al. |
| 2015/0224025 A1 | 8/2015 | Darna |
| 2015/0351999 A1 | 12/2015 | Brouse |
| 2015/0379880 A1 | 12/2015 | Sethi |
| 2016/0000640 A1* | 1/2016 | Lai ........................ G16H 20/30 |
| | | 601/149 |
| 2016/0008206 A1* | 1/2016 | Devanaboyina ....... A61H 7/007 |
| | | 601/136 |
| 2016/0058375 A1 | 3/2016 | Rothkopf |
| 2016/0155362 A1 | 6/2016 | Joshi et al. |
| 2016/0166463 A1* | 6/2016 | Douglas .................. A61F 5/012 |
| | | 601/150 |
| 2016/0213558 A1 | 7/2016 | Stanbridge |
| 2016/0255944 A1* | 9/2016 | Baranski ............... A44C 5/2071 |
| 2016/0346501 A1 | 12/2016 | Hooper et al. |
| 2016/0374886 A1 | 12/2016 | Wyatt et al. |
| 2017/0027459 A1 | 2/2017 | Shimuta |
| 2017/0036009 A1 | 2/2017 | Hughes et al. |
| 2017/0049611 A1 | 2/2017 | Rosh Vora et al. |
| 2017/0113039 A1 | 4/2017 | Tuan |
| 2017/0209333 A1* | 7/2017 | Shoup .................... A61M 21/02 |
| 2017/0216546 A1 | 8/2017 | Henry et al. |
| 2017/0246076 A1 | 8/2017 | Miller et al. |
| 2017/0265563 A1 | 9/2017 | Ma et al. |
| 2017/0296429 A1 | 10/2017 | Mayo et al. |
| 2017/0340209 A1 | 11/2017 | Klaassen et al. |
| 2017/0372565 A1 | 12/2017 | Do et al. |
| 2018/0028396 A1 | 2/2018 | Brodsky |
| 2018/0033263 A1 | 2/2018 | Novich et al. |
| 2018/0036534 A1 | 2/2018 | Shin |
| 2018/0056029 A1 | 3/2018 | Akimoto et al. |
| 2018/0078206 A1 | 3/2018 | Aimone et al. |
| 2018/0085283 A1 | 3/2018 | Rahman |
| 2018/0099143 A1 | 4/2018 | Kim et al. |
| 2018/0110960 A1 | 4/2018 | Youngblood et al. |
| 2018/0192947 A1 | 7/2018 | Tokko et al. |
| 2018/0228689 A1 | 8/2018 | Lach et al. |
| 2018/0231939 A1 | 8/2018 | Kim |
| 2018/0256432 A1 | 9/2018 | Mayo et al. |
| 2018/0318545 A1 | 11/2018 | Jones et al. |
| 2019/0001131 A1 | 1/2019 | Ziv |
| 2019/0029878 A1 | 1/2019 | Linder et al. |
| 2019/0070057 A1 | 3/2019 | Conner et al. |
| 2019/0108852 A1 | 4/2019 | Eagleman et al. |
| 2019/0110950 A1 | 4/2019 | Smith et al. |
| 2019/0125619 A1 | 5/2019 | Zeutzius et al. |
| 2019/0163270 A1 | 5/2019 | Da Silva et al. |
| 2019/0223781 A1 | 7/2019 | Arrington et al. |
| 2019/0269914 A1* | 9/2019 | Moaddeb ................. A61N 7/00 |
| 2019/0290143 A1 | 9/2019 | Iwata et al. |
| 2019/0298181 A1 | 10/2019 | Iwata et al. |
| 2019/0298265 A1 | 10/2019 | Keating et al. |
| 2020/0061377 A1 | 2/2020 | Siegle et al. |
| 2020/0085380 A1 | 3/2020 | Sampson |
| 2020/0178887 A1 | 6/2020 | Correa Ramirez et al. |
| 2020/0202120 A1 | 6/2020 | Shelly et al. |
| 2020/0215296 A1 | 7/2020 | Rabin et al. |
| 2020/0215298 A1 | 7/2020 | Rabin et al. |
| 2020/0219615 A1 | 7/2020 | Rabin et al. |
| 2020/0222279 A1 | 7/2020 | Spring et al. |
| 2020/0261303 A1 | 8/2020 | Bennett |
| 2020/0268602 A1 | 8/2020 | Akaikine et al. |
| 2020/0289001 A1 | 9/2020 | Mantrawadi et al. |
| 2020/0297574 A1* | 9/2020 | Poon ...................... A61H 31/005 |
| 2020/0306493 A1 | 10/2020 | Lee |
| 2020/0324104 A1 | 10/2020 | Labuschagne et al. |
| 2020/0356172 A1 | 11/2020 | Fainstain |
| 2020/0389711 A1 | 12/2020 | Dixit |
| 2021/0085559 A1 | 3/2021 | Smith et al. |
| 2021/0089130 A1 | 3/2021 | Novich et al. |
| 2021/0117002 A1 | 4/2021 | Eagleman et al. |
| 2021/0205169 A1 | 7/2021 | Schnieder et al. |
| 2021/0236370 A1 | 8/2021 | Mayo et al. |
| 2021/0275386 A1* | 9/2021 | Ravikumar ............... A61F 5/34 |
| 2021/0307630 A1 | 10/2021 | Sano et al. |
| 2021/0338971 A1 | 11/2021 | Blahnik et al. |
| 2021/0386594 A1 | 12/2021 | Ramanan et al. |
| 2021/0393152 A1 | 12/2021 | Young et al. |
| 2022/0105359 A1 | 4/2022 | Rappaport |

(56) References Cited

U.S. PATENT DOCUMENTS

| | | |
|---|---|---|
| 2022/0241137 A1 | 8/2022 | Solana et al. |
| 2022/0287909 A1 | 9/2022 | Sanchez Solana et al. |
| 2023/0001191 A1 | 1/2023 | Schwarz et al. |
| 2023/0096515 A1 | 3/2023 | McDevitt et al. |
| 2023/0165746 A1 | 6/2023 | Wersland et al. |
| 2023/0277410 A1 | 9/2023 | Cisneros et al. |
| 2023/0347102 A1 | 11/2023 | Nazarian et al. |

FOREIGN PATENT DOCUMENTS

| | | | |
|---|---|---|---|
| CN | 107349092 A | | 11/2017 |
| CN | 107349093 A | | 11/2017 |
| CN | 108514470 A | | 9/2018 |
| CN | 210019307 U | | 2/2020 |
| CN | 210228475 U | * | 4/2020 |
| CN | 210673734 U | | 6/2020 |
| CN | 210932663 U | | 7/2020 |
| CN | 211934039 U | | 11/2020 |
| CN | 107129690 B | | 1/2021 |
| CN | 212489876 U | | 2/2021 |
| CN | 212574862 U | | 2/2021 |
| CN | 213215683 U | | 5/2021 |
| CN | 112971751 A | | 6/2021 |
| CN | 113080904 A | | 7/2021 |
| CN | 113142758 A | | 7/2021 |
| CN | 113143234 A | | 7/2021 |
| CN | 113273984 A | | 8/2021 |
| CN | 113349747 A | | 9/2021 |
| CN | 113520357 A | | 10/2021 |
| CN | 113520358 A | | 10/2021 |
| CN | 214317214 U | | 10/2021 |
| CN | 113739986 A | | 12/2021 |
| JP | 2002035066 A | | 2/2002 |
| KR | 101951917 B1 | | 4/2019 |
| KR | 102311560 B1 | | 10/2021 |
| TW | M543073 U | | 6/2017 |
| WO | 9930612 A1 | | 6/1999 |
| WO | 0039765 A1 | | 7/2000 |
| WO | 2011127918 A1 | | 10/2011 |
| WO | 2016097821 A1 | | 6/2016 |
| WO | 2017173436 A1 | | 10/2017 |
| WO | 2018139150 A1 | | 8/2018 |
| WO | 2019128768 A1 | | 7/2019 |
| WO | 2021147664 A1 | | 7/2021 |
| WO | 2021190377 A1 | | 9/2021 |
| WO | 2021190599 A1 | | 9/2021 |
| WO | 2021203921 A1 | | 10/2021 |
| WO | 2021208679 A1 | | 10/2021 |
| WO | 2021213071 A1 | | 10/2021 |
| WO | 2021213170 A1 | | 10/2021 |
| WO | 2021229276 A1 | | 11/2021 |
| WO | 2022133222 A1 | | 6/2022 |
| WO | 2023004186 A1 | | 1/2023 |

OTHER PUBLICATIONS

Wigram, Anthony Lewis, "The Effects of Vibroacoustic Therapy on Clinical and Non-Clinical Populations", Thesis Submitted for the Degree of Doctor of Philosophy, St. Georges Hospital Medical School, London University, 1996, 290 pages.

Wikipedia, "Silicone Rubber Keypad", https://en.wikipedia.org/wiki/Silicone_rubber_keypad; pages of website downloaded on Oct. 19, 2020; 3 pages <https://vault.netvoyage.com/neWeb2/goid.aspx?id=4850-9014-5487>.

Wiorek, Alexander et al., "Epidermal Patch with Glucose Biosensor: pH and Temperature Correction Toward More Accurate Sweat Analysis During Sport Practice", Analytial Chemistry, vol. 92, 2020, 9 pages.

Yamane, Takahiro et al., "Simple Wearable Device to Reduce Stress When Delivering a Speech Without Pre-Training", The Korean Society of Medical Informatics, 2021, 10 pages.

Youtube, "Breo iSee4 vs. Renpho Eye Massager Video", https://www.youtube.com/watch?v=kgWLp-Mrxrw, 2021, 2 pages.

Youtube, "Does This Thing Work? Renpho Eye Massager Review Video", https://www.youtube.com/watch?v=kDivgRIStaQ, 2021, 2 pages.

Youtube, "Getting Energized with Acupressure & Diet—Dr. Suzanna M. Zick at National Cancer Survivors Day Video", https://www.youtube.com/watch?v=sArsCf4Pkk4, 2017, 2 pages.

Youtube, "Headaches . . . ? Eye Massager Entered the Chat! RENPHO Eye Massager Review Video", Jul. 7, 2022, 2 pages.

Youtube, "Renpho Eye Massager Reviews", https://www.youtube.com/results?search_query=renpho+eye+massager+reviews, 2020, 7 pages.

Youtube, "Renpho Shiatsu Eye Massager with Heat Air Compression and Bluetooth Music Video", 2020, 3 pages.

ZD NET, "Microsoft Patent Shows Wearable Band with Haptic Feedback", https://www.zdnet.com/article/microsoft-filed-a-patent-for-a-haptic-wearable-muscle-stimulator/; pages of website downloaded on Oct. 19, 2020; 8 pages <https://vault.netvoyage.com/neWeb2/goid.aspx?id=4819-9273-4927>.

Zhao, Jiangqi et al. "A Fully Integrated and Self-Powered Smartwatch for Continuous Sweat Glucose Monitoring", ACS Sens., vol. 4, 2019, pp. 1925-1933.

Zick, ND, MPH, Suzanna Maria et al., "Acupressure for Cancer-Fatique in Ovarian Cancer Survivor (The AcuOca Study): A Community-Based Clinical Trial Study Protocol Examining the Impact of Self-Acupressure on Persistant Cancer Related Fatigue in Ovarian Cancer Survivors", University of Michigan, Elsevier, 2021, 37 pages.

Kozyackin, "Professor Kozyavkin Method_ Vibratin Therapy Webpage", https://kozyavkin.com/en/treatment/rehab-components/content/vibration-therapy/; pages of website downloaded on Oct. 16, 2020; 5 pages <https://vault.netvoyage.com/neWeb2/goid.aspx?id=4830-8375-9311>.

Lee, Anna, Chan, Simon K.C., Fan, Lawrence T.Y., Stimulation of the wrist acupuncture point PC6 for preventing postoperative nausea and vomiting, pp. 3-137, Cochrane Database of Systematic Reviews 2015, Issue 11., 2016 The Cochrane Collaboration. Published by John Wiley & Sons, Ltd.

Linked In, "Dr. Grame Massagers", https://www.drgraeme.com/articles/2019/08/scientific-effects; pages of website downloaded on Oct. 19, 2020; 9 pages <https://vault.netvoyage.com/neWeb2/goid.aspx?id=4838-7938-4271>.

Liu, Zeng-Ding et al., "Cuffless Blood Pressure Estimation Using Pressure Pulse Wave Signals", Sensors, vol. 18, 2018, 15 pages.

Ludeberg, T. et al., "Pain Alleviation by Vibratory Stimulation", Pain, vol. 20, 1984, pp. 25-44.

Machine-assisted English language abstract and machine-assisted English translation for CN 113349747 A extracted from espacenet.com database on Jan. 18, 2022, 31 pages.

Machine-assisted English language abstract and machine-assisted English translation for CN 113739986 A extracted from espacenet.com database on Jan. 18, 2022, 26 pages.

Machine-assisted English language abstract and machine-assisted English translation for CN 214317214 U extracted from espacenet.com database on Jan. 18, 2022, 22 pages.

Machine-assisted English translation for TWM 543073 U extracted from espacenet.com database on Apr. 20, 2022, 6 pages.

Mattsson, Adam et al., "Vibraaesthetics of Music—The Design of BEATHOVEN: a Haptic Device of Enjoying Music Through Vibrotactile Sensations", Lulea University of Technology, Industrial Design Engineering, Master's Level, 2021, 106 pages.

Men's Health, "Meet the Vibrating Wristband That Claims to Reduce Stress in Seconds", https://www.menshealth.com/health/a19530192/this-wristband-reduces-stress/#:~:text=But%20a%20brand%20called%20TouchPoints,the%20brain's%20response%20to%20stress <https://www.menshealth.com/health/a19530192/this-wristband-reduces-stress/>; pages of website downloaded on May 11, 2021; 5 pages.

NCBI, "Local Application of Vibratin in Motor Rehabilitation—Scientific and Practical Considerations", https://www.ncbi.nlm.nih.gov/pmc/articles/PMC5486165/; pages of website downloaded on Oct. 16, 2020; 7 pages <https://vault.netvoyage.com/neWeb2/goid.aspx?id=4831-0617-2879>.

(56) References Cited

OTHER PUBLICATIONS

Nexquest, "Nexquest Website", https://nexquest.com/; pages of website downloaded on Oct. 16, 2020; 5 pages <https://vault.netvoyage.com/neWeb2/goid.aspx?id=4828-1951-9439>.
Nomisk, "Maia Massager Webpage", https://nomisk.com/products/maia?tw_source=google&tw_adid=552654779945&tw_campaign=14934575409&gclid=Cj0KCQjwtsCgBhDEARIsAE7RYh0Wvv77DO9_7poiBR0ZGITz_1G8CQFIOHgVn1rNwTNej-_Xy--eLAlaAiv6EALw_wcB, 2023, 11 pages.
Novasentis, "Haptic Wristbands for Smartwatches", Glassninja, •published at least before Jan. 8, 2022.
OCAD, "Body-Centric Technologies; Category 5: Workship Notes 5—Expressive Haptic Throw Blanket" http://blog.ocad.ca/wordpress/digf6044-fw201803-01/category/workshop-notes-5/; pages of website downloaded on Oct. 16, 2020; 101 pages <https://vault.netvoyage.com/neWeb2/goid.aspx?id=4843-9933-0255>.
Ohio State University, "Easeband Webpage", 2019, 2 pages.
Omron Healthcare, Inc., "HeartGuide Wrist Blood Pressure Monitor Model BP8000-M Instruction Manual", 2019, 72 pages.
Pain Care Labs, "VibraCool Webpage", https://paincarelabs.com/pages/vibracool 2021, 13 pages.
Paredes, Pablo Enrique et al., CalmMeNow: Exploratory Research and Design of Stress Mitigating Mobile Interventions, Proceedings of the International Conference on Human Factors in Computing Systems, CHI 2011 Work-in-Progress, Extended Abstracts Volume, pp. 1699-1704, Vancouver, BC, Canada, <https://vault.netvoyage.com/neWeb2/goid.aspx?id=4825-8367-6101>. May 7-12, 2011; 6 pages.
Percardium 6 Image; published at least before Jan. 8, 2020, 1 page <https://vault.netvoyage.com/neWeb2/goid.aspx?id=4849-8281-7989>.
Philip Stein, "Natural Frequency Watches & Natural Frequency Bracelets", https://philipstein.com/; pages of website downloaded on Oct. 16, 2020; 12 pages <https://vault.netvoyage.com/neWeb2/goid.aspx?id=4845-0641-5055>.
Pournot, Herve et al., "The Acute Effect of Local Vibration as a Recovery Modality from Exercise_Induced Increased Muscle Stiffness", J Sports Sci Med, vol. 15, No. 1, Feb. 23, 2016, pp. 142-147; https://www.ncbi.nlm.nih.gov/pmc/articles/PMC4763833/; pages of website downloaded on Oct. 19, 2020; 12 pages <https://vault.netvoyage.com/neWeb2/goid.aspx?id=4831-1431-7263>.
PR Web, "New Reliefband Wearable Devices Unveiled at CES 2020 Expand Innovative Lineup of Nausea Prevention Products", 2020, 4 pages.
Practical Pain Management (PPM), "Vibration for Chronic Pain", https://www.practicalpainmanagement.com/treatments/rehabilitation/vibration-chronic-pain; pages of website downloaded on Oct. 16, 2020; 13 pages <https://vault.netvoyage.com/neWeb2/goid.aspx?id=4816-8364-8463>.
Precision Microdrives, "How to Drive a Vibration Motor With Arduino and Genuino", https://www.precisionmicrodrives.com/content/how-to-drive-a-vibration-motor-with-arduino-and-genuino/; pages of website downloaded on Oct. 19, 2020; 7 pages <https://vault.netvoyage.com/neWeb2/goid.aspx?id=4836-4850-1711>.
Pulse Band Clip published at least before Jan. 8, 2020; 1 page <https://vault.netvoyage.com/neWeb2/goid.aspx?id=4812-2478-7141>.
Relief Band Technologies LLC, "Relief Band 2.0", published at least before Jan. 8, 2020; 1 page <https://vault.netvoyage.com/neWeb2/goid.aspx?id=4822-4819-7317>.
RENPHO, "RENPHO Shiatsu Eye Massager with Heat, Air Compression, and Bluetooth Music", https://renpho.com/products/renpho-shiatsu-eye-massager, 2020, 9 pages.
Rosello, Oscar, "HeartBit: Mindful Control of Heart Rate Using Haptic Biofeedback", Massachusetts Institute of Technology, Feb. 2020, 69 pages.
Schreurs, B.G. et al., "Classical Conditioning of the Rabbit's Nictating Membrane Response to a Piezoceramic Vibrotactile CS", Behavior Research Methods, Intruments, & Computers, vol. 18, No. 4, 1986, pp. 359-362.
SEA Band, "Sea Band Product Webpage", https://www.sea-band.com/; pages of website downloaded on Oct. 19, 2020; 8 pages <https://vault.netvoyage.com/neWeb2/goid.aspx?id=4833-4821-5759>.
SEA Products, "SEA Bands: SEA Bands Relieve Motion Sickness by Applying Pressue on the P6 Acupressure Point on the Under Side of Your Wrist", https://www.seaproductsonline.com/SEA-Bands-SEA-Bands-relieve-motion-sickness-by-applying-pressure-on-the-P6-acupressure-point-on-the-under-side-of-your-wrist-_p_183.html; pages of website downloaded on Oct. 19, 2020; 2 pages <https://vault.netvoyage.com/neWeb2/goid.aspx?id=4837-6908-7951>.
Segman, Yosef (Joseph), "New Method for Computing Optical Hemodynamic Blood Pressure", J. Clin. Exp. Cardiolog., vol. 7, No. 12, 2016, 7 pages.
Sense Relief, "Sense Relief Application Webpage", https://sensereliefapp.com/, 2022, 4 pages.
Therabody, "RecoveryAir JetBoots Manual", 2023, 24 pages.
Therabody, Inc., "Theragun PRO Plus Webpage", https://www.therabody.com/us/en-us/theragun-proplus.html, 2023, 9 pages.
Touchpoint, "Wear Calm website", https://thetouchpointsolution.com/; pages of website downloaded on May 11, 2021, 7 pages.
TWM image published at least before Jan. 8, 2020; 1 page <https://vault.netvoyage.com/neWeb2/goid.aspx?id=4840-9369-1077>.
U.S. National Library of Medicine, "Wearable Emotion Prosthetics for Post Traumatic Stress Disorder (EP-PTSD)", https://clinicaltrials.gov/ct2/show/NCT03529981, Jan. 13, 2021, 11 pages.
Umair, Muhammad et al., "Exploring Personalized Vibrotactile and Thermal Patterns for Affect Regulation", Virtual Event, USA, DIS, 2021, 24 pages.
U.S. Appl. No. 16/984,222, filed Aug. 4, 2020.
U.S. Appl. No. 17/577,890, filed Jan. 18, 2022.
USPTO, "Final Office Action dated Oct. 25, 2023 for U.S. Appl. No. 18/059,247", 25 pages.
USPTO, "Non-Final Office Action dated Nov. 21, 2023 for U.S. Appl. No. 17/588,570", 18 pages.
USPTO, "Non-Final Office Action for U.S. Appl. No. 17/933,419", Mar. 2, 2023, 26 pages.
USPTO, "Pending Claims for U.S. Appl. No. 18/059,247 as of Aug. 21, 2023", 4 pages.
Wang, Michael T.M. et al., "Abstract of Randomised Trial of the Clinical Utility of an Eyelid Massage Device for the Management of Meibomian Gland Dysfunction", Cont Lens Anterior Eye, vol. 42, No. 6, 2019, pp. 620-624.
WAT Medical Enterprise Ltd., EmeTerm Sea Sickness bands clip published at least before Jan. 8, 2020.
Waveform Gernerators, "555 Timer Tutorials", https://www.electronics-tutorials.ws/waveforms/555_timer.html; pages of website downloaded on Oct. 19, 2020; 19 pages <https://vault.netvoyage.com/neWeb2/goid.aspx?id=4842-4946-6063>.
English language abstract and machine-assisted English translation for CN 107349092 A extracted from espacenet.com database on Apr. 20, 2022, 8 pages.
English language abstract and machine-assisted English translation for CN 107349093 A extracted from espacenet.com database on Apr. 20, 2022, 9 pages.
English language abstract and machine-assisted English translation for CN 108514470 A extracted from espacenet.com database on Jan. 4, 2024, 15 pages.
English language abstract and machine-assisted English translation for CN 11271751 A extracted from espacenet.com database on Jan. 18, 2022, 25 pages.
English language abstract and machine-assisted English translation for CN 113080904 A extracted from espacenet.com database on Jan. 18, 2022, 18 pages.
English language abstract and machine-assisted English translation for CN 113142758 A extracted from espacenet.com database on Jan. 18, 2022, 38 pages.

(56) References Cited

OTHER PUBLICATIONS

English language abstract and machine-assisted English translation for CN 113143234 A extracted from espacenet.com database on Jan. 18, 2022, 16 pages.
English language abstract and machine-assisted English translation for CN 113273984 A extracted from espacenet.com database on Jan. 18, 2022, 28 pages.
English language abstract and machine-assisted English translation for CN 113520357 A extracted from espacenet.com database on Jan. 18, 2022, 30 pages.
English language abstract and machine-assisted English translation for CN 113520358 A extracted from espacenet.com database on Jan. 18, 2022, 31 pages.
English language abstract and machine-assisted English translation for CN 210019307 U extracted from espacenet.com database on Jan. 18, 2022, 9 pages.
English language abstract and machine-assisted English translation for CN 210673734 U extracted from espacenet.com database on Mar. 14, 2023, 15 pages.
English language abstract and machine-assisted English translation for CN 210932663 U extracted from espacenet.com database on Mar. 14, 2023, 8 pages.
English language abstract and machine-assisted English translation for CN 211934039 U extracted from espacenet.com database on Jan. 18, 2022, 32 pages.
English language abstract and machine-assisted English translation for CN 212489876 U extracted from espacenet.com database on Jan. 18, 2022, 18 pages.
English language abstract and machine-assisted English translation for CN 212574862 U extracted from espacenet.com database on Jan. 18, 2022, 32 pages.
English language abstract and machine-assisted English translation for CN 213215683 U extracted from espacenet.com database on Jan. 18, 2022, 38 pages.
English language abstract and machine-assisted English translation for JP 2002-035066 A extracted from espacenet.com database on Mar. 14, 2023, 8 pages.
English language abstract and machine-assisted English translation for KR 101951917 B1 extracted from espacenet.com database on Mar. 14, 2023, 10 pages.
English language abstract and machine-assisted English translation for KR 102311560 B1 extracted from espacenet.com database on Mar. 14, 2023, 14 pages.
English language abstract and machine-assisted English translation for WO 2018/139150 A1 extracted from espacenet.com database on Mar. 14, 2023, 31 pages.
English language abstract and machine-assisted English translation for WO 2019/128768 A1 extracted from espacenet.com database on Jan. 18, 2022, 16 pages.
English language abstract and machine-assisted English translation for WO 2021/147664 A1 extracted from espacenet.com database on Jan. 18, 2022, 39 pages.
English language abstract and machine-assisted English translation for WO 2021/190377 A1 extracted from espacenet.com database on Jan. 18, 2022, 30 pages.
English language abstract and machine-assisted English translation for WO 2021/190599 A1 extracted from espacenet.com database on Jan. 18, 2022, 59 pages.
English language abstract and machine-assisted English translation for WO 2021/203921 A1 extracted from espacenet.com database on Jan. 18, 2022, 31 pages.
English language abstract and machine-assisted English translation for WO 2021/208679 A1 extracted from espacenet.com database on Jan. 18, 2022, 32 pages.
English language abstract and machine-assisted English translation for WO 2021/213071 A1 extracted from espacenet.com database on Jan. 18, 2022, 30 pages.
English language abstract and machine-assisted English translation for WO 2021/213170 A1 extracted from espacenet.com database on Jan. 18, 2022, 25 pages.

English language abstract for International Patent Publication No. WO 99/30612 and machine-assisted English translation of equivalent Russian Federation Patent No. RU 2141250 extracted from www.espacenet.com database on Nov. 2, 2020; 6 pages.
English language abstract for WO 2011/127918 A1 extracted from espacenet.com database on Mar. 14, 2023, 2 pages.
Flanigan, Tara, "These Vibrating Wristbands Claim to Melt Stress Way in Just 30 Seconds", <https://mashable.com/2017/08/14/vibrating-stress-wearable-relieve/>; Aug. 14, 2017, 7 pages.
Frey, Jeremy et al., "Breeze: Sharing Biofeedback Through Wearable Technologies", Ubiquitous Computing Lab, Interdisciplinary Center, Israell, France, 2018, 12 pages.
Google Play, "MeTime Acupressure Application Information", https://play.google.com/store/apps/details?id=edu.umich.metime&hl=en, 2023, 3 pages.
Google, "Flat Capacitors", https://www.google.com/search?q=flat+capacitors&rlz=1 C1CHBF_enUS874US874&oq=flat +capacitors&aqs=chrome..69i57jOI5.3473jOj8&sourceid=chrome&ie=UTF-8; pages of website downloaded on Oct. 19, 2020; 3 pages <https://vault.netvoyage.com/neWeb2/goid.aspx?id=4840-6648-9551>.
Google, "Seaband With Haptics", https://www.google.com/search?q=sea+band+with+haptics&tbm=isch&ved=2ahUKEwjbocjT-8DsAhXMAN8KHe5eDtEQ2-cCegQIABAA&oq=sea+band+with+haptics&gs_lcp=CgNpbWcQAzIECCMQJ1DFPVjFPWCLSGgAcAB4AIABSIgBSJIBATGYAQCgAQGqAQtnd3Mtd2I6LWItZ8ABAQ&sclient=img&ei=-q-NX9u8BsyB_AbuvbmIDQ&bih=96+9&biw=1920&rlz=1+C1+CHBF+enUS874US874; pages of website downloaded on Oct. 19, 2020; 2 pages <https://vault.netvoyage.com/neWeb2/goid.aspx?
Haddad, Serj et al., "Continuous PPG-Based Blood Pressure Monitoring Using Multi-Linear Regression", 2020, 9 pages.
Haining Beyond Seals Co., Ltd, "DN 10 mm Black Color Silicone Push Button Cover for Power Key Switch" http://www.molded-rubberseals.com/sale-11816310-dn-10-mm-black-color-silicone-push-button-cover-for-power-key-switch.html; pages of website downloaded on Oct. 16, 2020; 4 pages <https://vault.netvoyage.com/neWeb2/goid.aspx?id=4813-5138-1967>.
Hosanee, Manish et al., "Cuffless Single-Site Photoplethysmography for Blood Pressure Monitoring", Journal of Clinical Medicine, 2020, 14 pages.
Indiegogo, "WrisLax—Wearable Wrist Massager & Sleeping Help Webpage", https://www.indiegogo.com/projects/wrislax-wearable-wrist-massager-sleeping-help#/, 2023, 5 pages.
Inner Solutions, "Creating Quality Vibroacoustic Sound Tables for Over 20 Years", https://innersoulutions.com/faqs/; pages of website downloaded on Oct. 16, 2020; 8 pages <https://vault.netvoyage.com/neWeb2/goid.aspx?id=4830-4830-4079>.
Instagram, "Neosensory", Dec. 6, 2019, 1 page.
Interaxan, "Muse Devices Webpage", https://choosemuse.com/?utm source=google&utm medium=cpc&utmcampaign=BoF USA Search Brand&utm term=muse--e&utm_content=Brand_Name443962996222&gclid=Cj0KCQjw6uT4BRD5ARIsADwJQ1884JE4EjSS1aMYPhaiHDu-iaqOtX74WpyTtZtcUlg9D4gsYqLTbosaAk4REALw_wcB; pages of website downloaded on Oct. 16, 2020; 9 pages <https://vault.netvoyage.com/neWeb2/goid.aspx?id=4825-1831-6239>.
Interaxan, "Muse Guided Meditation Bundle Webpage", https://choosemuse.com/muse-s-guided-bundle/?gclid=C]0KCQjwuJz3BRDTARIsAMg-HxVO_OCiMfrIDLDL8eTIssNH6VhV-ICVhKr4YdRrRfwAMaeej91Mwt4aAwaEALw_wcB; pages of website downloaded on Oct. 16, 2020; 7 pages <https://vault.netvoyage.com/neWeb2/goid.aspx?id=4825-1831-6239>.
International Search Report for Application No. PCT/US2023/014896 dated Nov. 6, 2023, 1 page.
Joicom Corporation, "Renpho Model: SD-002 Electric Eye Massager User Manual", 2019, 16 pages.
Kelling, Chelsea et al., "Good Vibes: The Impact of Haptic Patterns on Stress Levels", Conference Paper, Academic Mindtrek, 2016, 8 pages.
Kirmayer, MD, Laurence J., "Unpacking the Placebo Response: Insights from Ethnographic Studies of Healing", The Journal of Mind_Body Regulation, vol. 1, No. 3, 2011, 13 pages.

(56) References Cited

OTHER PUBLICATIONS

KOHEEL, "KOHEEL Wearable Device for Headache, Migraine, Tenision Relief—Support Acupressure Relaxation, Stress Alleviation, Soothing Muscle Pain Webpage", https://www.koheel.com/products/wearable-device-for-headache-migraine-tension-relief, 2023, 4 pages.

Kozin, Gene, Livongo—How Do Blood Pressure Monitors Work?:, https://techblog.livongo.com/how-do-blood-pressure-monitors-work/; pages of website downloaded on Oct. 19, 2020; 6 pages <https://vault.netvoyage.com/neWeb2/goid.aspx?id=4847-4544-1999>.

Acu First Clip Image, published at least before Jan. 8, 2020; 1 page <https://vault.netvoyage.com/neWeb2/goid.aspx?id=4813-7571-6549>.

Amazon, "Acuressure SCAT Motion-Aid Wrist Straps w/Magnets from AME", https://www.amazon.com/exec/obidos/ASIN/B000K5ONQ2/26090703msg-20/; pages of website downloaded on Oct. 19, 2020; 7 pages <https://vault.netvoyage.com/neWeb2/goid.aspx?id=4821-6895-9695>.

Amazon, Band for Motion Sickness (i-Trans Wristband DM-800 HIVOX), https://www.amazon.com/Motion-Sickness-i-Trans-Wristband-DM-800/dp/B002ECWTKQ; pages of website downloaded on Oct. 16, 2020; 7 pages <https://vault.netvoyage.com/neWeb2/goid.aspx?id=4840-4202-6703>.

Amazon, "Bioband Motion Sickness Band Black", https://www.amazon.com/exec/obidos/ASIN/B001KN5790/26090703msg-20/; pages of website downloaded on Oct. 19, 2020; 8 pages <https://vault.netvoyage.com/neWeb2/goid.aspx?id=4833-1059-6815>.

Amazon, "EmeTerm Relieve Nausea Electrode Stimulator", https://www.amazon.com/dp/B07LFXLV5J/ref=vp_d_pb_TIER2_trans_Ip_B07B84TZ6Z_pd?_encoding=UTF8&pd_rd_i=B07LFXLV5J&pd_rd_w=pAJIQ&pf_rd_p=e97d49af- c67a-4ec8-8fd9-01 d649d9c891&pf_rd_r=4c2b3f49-a49b-49e1 -96fa-0ca7234f0356&pd_rd_r=4c2b3f49- a49b-49e1-96fa-0ca7234f0356&pd_rd_wg=hV1 bq; pages of website downloaded on Oct. 19, 2020; 11 pages <https://vault.netvoyage.com/neWeb2/goid.aspx?id=4824-8680-9295>.

Amazon, "Motion Cure Wristband", https://www.amazon.com/exec/obidos/ASIN/B018P6YX8U/26090703msg-20/; pages of website downloaded on Oct. 19, 2020; 9 pages <https://vault.netvoyage.com/neWeb2/goid.aspx?id=4830-5992-1615>.

Amazon, "NoMo Nausea Instant Relief Aromatherapy Anti-Nausea Bands with Acupressure", https://www.amazon.com/s?k=nomo+nausea+band&i=hpc&rh=n %3A3760901&linkCode=II2&linkId=784bf82778438a3f266816a1ba30b4ef&tag=26090703msg-20&ref=as_li_ss_tl; pages of website downloaded on Oct. 19, 2020; 10 pages <https://vault.netvoyage.com/neWeb2/goid.aspx?id=4848-0639-0479>.

Amazon, "PSI Bands", https://www.amazon.com/stores/node/3039422011?_encoding=UTF8&field-Ibr_brands_browse-bin=Psi%20Bands&linkCode=II2&linkId=820afd077657430640cb993654a862d6&ref_=as_li_ss_tl&tag=26090703msg-20; pages of website downloaded on Oct. 19, 2020; 4 pages <https://vault.netvoyage.com/neWeb2/goid.aspx?id=4812-7301-7807>.

Amazon, "Reliefband Classic Anti-Nausea Writstband", https://www.amazon.com/dp/B07HCPYNXQ/ref=dp_cerb_3; pages of website downloaded on Oct. 16, 2020; 10 pages <https://vault.netvoyage.com/neWeb2/goid.aspx?id=4828-5459-7327>.

Amazon, "Reliefband Premier Motion Sickness Wristband", https://www.amazon.com/exec/obidos/ASIN/B07B84TZ6Z/26090703msg-20/; pages of website downloaded on Oct. 19, 2020; 8 pages <https://vault.netvoyage.com/neWeb2/goid.aspx?id=4848-0560-4047>.

Amazon, "RENPHO Eye Massager with Heat, Bluetooth Music Heated Eyeris 1 Massager for Migraines, Relax and Reduce Eye Strain Dark Circles Eye Bags Dry Eye Improve Sleep, Ideal Gift", https://www.amazon.com/RENPHO-Massager-Compression-Bluetooth-Rechargeable/dp/B07SM61FCT/ref=sr_1_4?crid=Q6B7L0D439Y0&keywords=eye%2Bmassager&qid=1677542344&s=hpc&sprefix=eye%2Bmassager%2Chpc%2C107&sr=1-4&ufe=app_do%3Aamzn1.fos.08f69ac3-fd3d-4b88-bca2-8997e41410bb&th=1, 1996-2023, 15 pages.

Amazon, "Wonder Healing Motion Sickness Nausea Relief Wristbands", https://www.amazon.sg/Wristbands-Acupressure-Anti-Nausea-Pregnancy-healing/dp/B07XJ7FV7D; pages of website downloaded on Oct. 19, 2020; 4 pages <https://vault.netvoyage.com/neWeb2/goid.aspx?id=4812-1298-7599>.

Apex Moon, "Wearable.com Website", <https://www.wearable.com/health-and-wellbeing/living-with-doppel-wearable-change-mood-7270>; pages of website downloaded on May 11, 2021; 3 pages.

Apollo, "90% of Children Experienced an Over 50% Reduction in Stress Scores, as Well as Improvements in Mood and Attention Control", https://apolloneuro.com/blogs/news/100-of-children-with-adhd-and-anxiety-experience-symptom-improvement-with-apollo-in-pilot-study, Apr. 17, 2020, 5 pages.

Apollo, "Apollo Improves Recovery and Performance in Elite Athletes", https://apolloneuro.com/blogs/news/apollo-improves-recovery-and-performance-in-athletes, Aug. 20, 2021, 4 pages.

Apollo, "Apollo Reduces Stress in Nursing Staff by 40% in Two Weeks", https://apolloneuro.com/blogs/news/apollo-reduces-stress-in-nursing-staff-by-40-in-two-weeks, Oct. 13, 2019, 3 pages.

Apollo, "Apollo Studies for PTSD Are Underway", https://apolloneuro.com/blogs/news/apollo-studies-for-ptsd-are-underway, Oct. 13, 2019, 3 pages.

Apollo, "Clinical Study Validates that Apollo Improves Cognitive Performance and Heart Rate Variability (HRV)", https://apolloneuro.com/blogs/news/clinical-study-validates-that-apollo-improves-cognitive-performance-and-heart-rate-variability-hrv, Jan. 20, 2020, 5 pages.

Apollo, "Life Can Be Chaotic. Apollo is Here to Help", https://web.archive.org/web/20191216155436/https://shop.apolloneuro.com/, 2019, 10 pages.

Apollo, "Preliminary Apollo Sleep Study Results Are in", https://apolloneuro.com/blogs/news/apollo-neuro-sleep-study-is-underway, Sep. 29, 2021, 6 pages.

Apollo, "Research Study Shows EEG Similarity Between Apollo Neuro Users and Experienced Meditators", https://apolloneuro.com/blogs/news/can-apollo-neuro-make-meditation-easier, May 27, 2021, 4 pages.

Apple, "Sense Relief App", https://apps.apple.com/us/app/sense-relief/id1457764420; pages of website downloaded on Oct. 16, 2020; 3 pages <https://vault.netvoyage.com/neWeb2/goid.aspx?id=4846-0780-0271>.

Applie, "Apple Watch Series 5 Smartwatch clip", published at least before Jan. 8, 2020; 1 page <https://vault.netvoyage.com/neWeb2/goid.aspx?id=4817-2154-6959>.

Arduino, "Arduino Program—VibrationMotor PWM", published at least before Jan. 8, 2020; 1 page <https://vault.netvoyage.com/neWeb2/goid.aspx?id=4820-6358-2405>.

ARS Technica, "Hear the Pulse: Heart Rate Monitoring Fitness Earbuds Tested", https://arstechnica.com/gadgets/2016/12/hear-the-pulse-heart-rate-monitoring-fitness-earbuds-tested/; pages of website downloaded on Oct. 16, 2020; 6 pages <https://vault.netvoyage.com/neWeb2/goid.aspx?id=4828-8184-4431>.

Auto Desk; indestructibles.com, "Haptic Interface Arduino Prototype", https://www.instructables.com/id/Haptic-Interface-Arduino-Prototype/; pages of website downloaded on Oct. 19, 2020; 7 pages <https://vault.netvoyage.com/neWeb2/goid.aspx?id=4814-4944-0719>.

Autodesk; indestructibles.com, "Pulse Sensor Wearable", https://www.instructables.com/id/Pulse-Sensor-Wearable/; pages of website downloaded on Oct. 19, 2020; 15 pages <https://vault.netvoyage.com/neWeb2/goid.aspx?id=4811-3257-4159>.

Azevedo, Ruben T. et al., "The Calming Effect of a New Wearable Device During the Anticipation of Public Speech", May 23, 2017, 7 pages.

Best Massage Chair Guide, "Vibration Massage: Its Positive Effects on Mind, Body, and Well-Being", https://bestmassagechairguide.com/vibrational-massage-and-its-positive-effects-on-your-body/; pages of website downloaded on Oct. 16, 2020; 8 pages <https://vault.netvoyage.com/neWeb2/goid.aspx?id=4818-3647-7903>.

(56) References Cited

OTHER PUBLICATIONS

Bioniva Wellness International, "Bionica Painless Wearable Well-Being Pendant Webpage", https://www.bioniva.com/therapeutic-devices/, 2018, 10 pages.
Blisslets, "Blisslets Product Webpage", https://myblisslets.com/; pages of website downloaded on Oct. 19, 2020; 15 pages <https://vault.netvoyage.com/neWeb2/goid.aspx?id=4828-1501-3583>.
Born to Invent, "The 555 Timer", https://www.bournetoinvent.com/projects/gcse_theory/4.html; pages of website downloaded on Oct. 19, 2020; 5 pages <https://vault.netvoyage.com/neWeb2/goid.aspx?id=4818-5609-0831>.
Breo, "Breo iSee4 Eye Massager Webpage", https://us.breo.com/products/breo-isee4-eye-massager, 2023, 7 pages.
CarpalRx, "CarpalRx Webpage", https://www.carpalrx.com/myofascial-release-massage-carpal-tunnel, 2022, 6 pages.
Castaneda, Denisse et al., "A Review on Wearable Photoplethysmography Sensors and Their Potential Futrue Applicatons ion Health Care", Int J. Bioelectron., vol. 4, No. 4, 2018, pp. 195-202, https://www.ncbi.nlm.nih.gov/pmc/articles/PMC6426305/; pages of website downloaded on Oct. 19, 2020; 19 pages <https://vault.netvoyage.com/neWeb2/goid.aspx?id=4821-5401-8767>.
Chinavasion, "P6 Smart Bracelet Heart Rate Blood Pressure Waterproof Smart Watch Webpage", http://chinavasion.com/china/wholesale/electronics/smart-watch/android-watch/p6-smart-bracelet-heart-rate-blood-pres-pel-0dcdeyg5; pages of website downloaded on Oct. 16, 2020; 6 pages <https://vault.netvoyage.com/neWeb2/goid.aspx?id=4825-7434-9263>.
Choi, Kyung Yun et al., "aSpire: Clippable, Mobile Pneumatic-Haptic Device for Breathing Rate Regulation via Personalizable Tactle Feedback", 2021, 8 pages.
Colloca, L. et al., "The Role of Learning in Nocebo and Placebo Effects", Pain, vol. 136, 2008, pp. 211-218.
Cool Wearables, "NovaSentis: Haptic Wristbands for Smartwatches", https://www.coolwearable.com/novasentis-haptic-wristbands-for-smartwatches/; pages of website downloaded on Oct. 16, 2020; 5 pages <https://vault.netvoyage.com/neWeb2/goid.aspx?id=4844-9979-5407>.
Costa, Jean et al., "BoostMeUp: Improving Cognitive Performance in the Moment by Unobtrusively Regulating Emotions with a SmartWatch", Association for Computing Machinery, 2018, 23 pages.
Costa, Jean et al., "EmotionCheck: Leveraging Bodilty Signals and False Feedback to Regulate Our Emotions", 2016, 12 pages.
Creganna Tactx Medical, "Deflectable & Steerable Catheter Handbook—Terminology Guide & Design Options", 2022, 7 pages.
Doppel, "Product Guide", 2018, 45 pages.
Dougherty, Donald M., "Generalization of a Tactile Stimulus in Horses", Journal of the Experimental Analysis of Behavior, vol. 59, 1993, pp. 521-528.
Dual Vibration Motors, published at least before Jan. 8, 2020; 1 page <https://vault.netvoyage.com/neWeb2/goid.aspx?id=4835-3479-7007>.
Durand, E. et al., "Plasticity in Respiratory Motor Control Selected Contriubtion: Classical Conditioning of Breathing Pattern After Two Acquisistion Trials in 2-day-old Mice", J. Apl Physiol, vol. 94, 2003, pp. 812-818.
Engadget, "Website", <https://www.engadget.com/apollo-neuro-stress-relief-wearable-155545997.html>; pages of website downloaded on May 11, 2021,8 pages.
English language abstract and machine-assisted English language translation of Chinese Patent No. CN 106333667 A extracted from www.espacenet. com database on Dec. 29, 2020, 99 pages.
English language abstract and machine-assisted English translation for CN 103284874 A extracted from espacenet.com database on Jan. 4, 2024, 11 pages.
English language abstract and machine-assisted English translation for CN 107129690 B extracted from espacenet.com database on Mar. 14, 2023, 21 pages.

\* cited by examiner

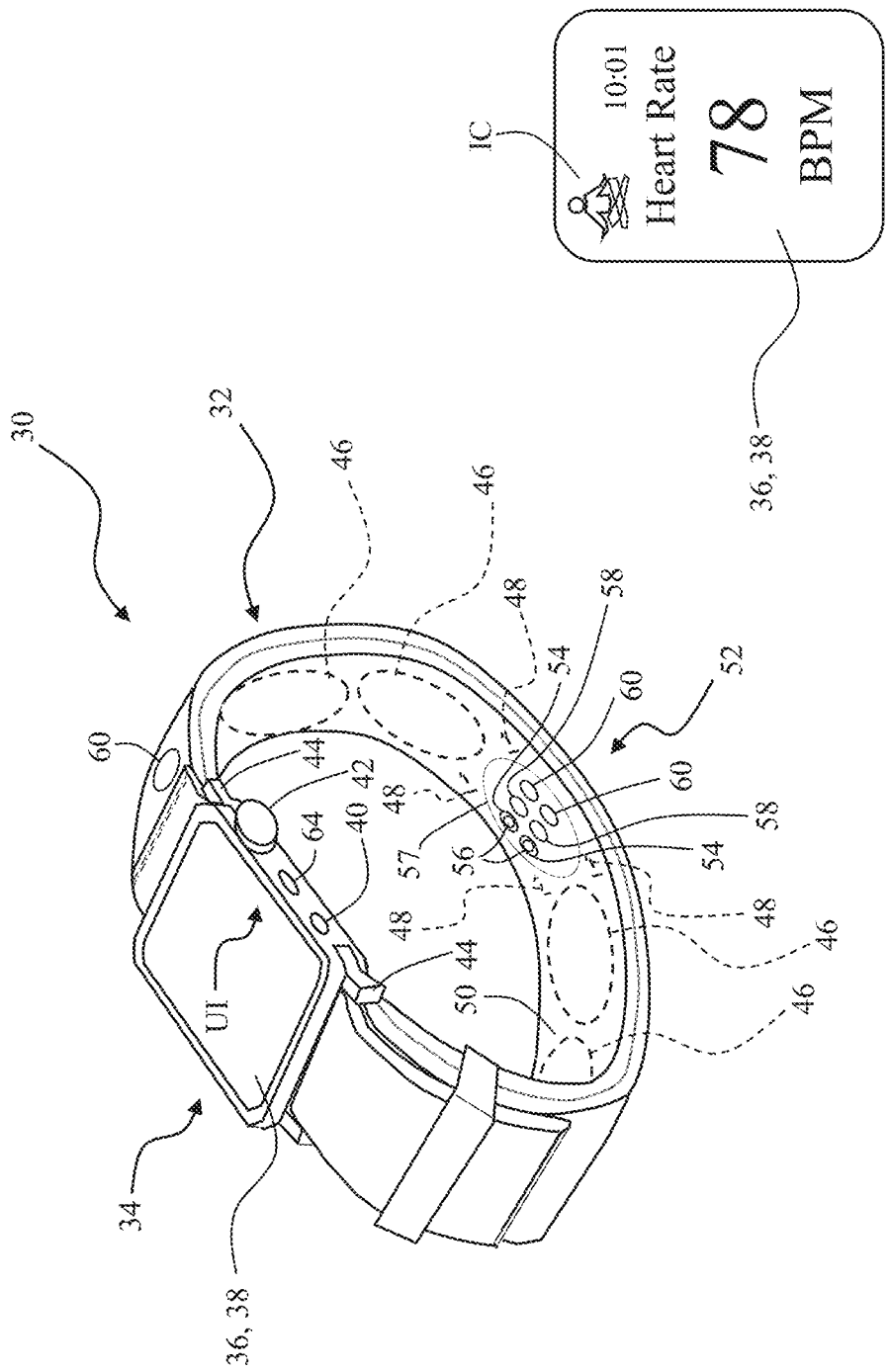

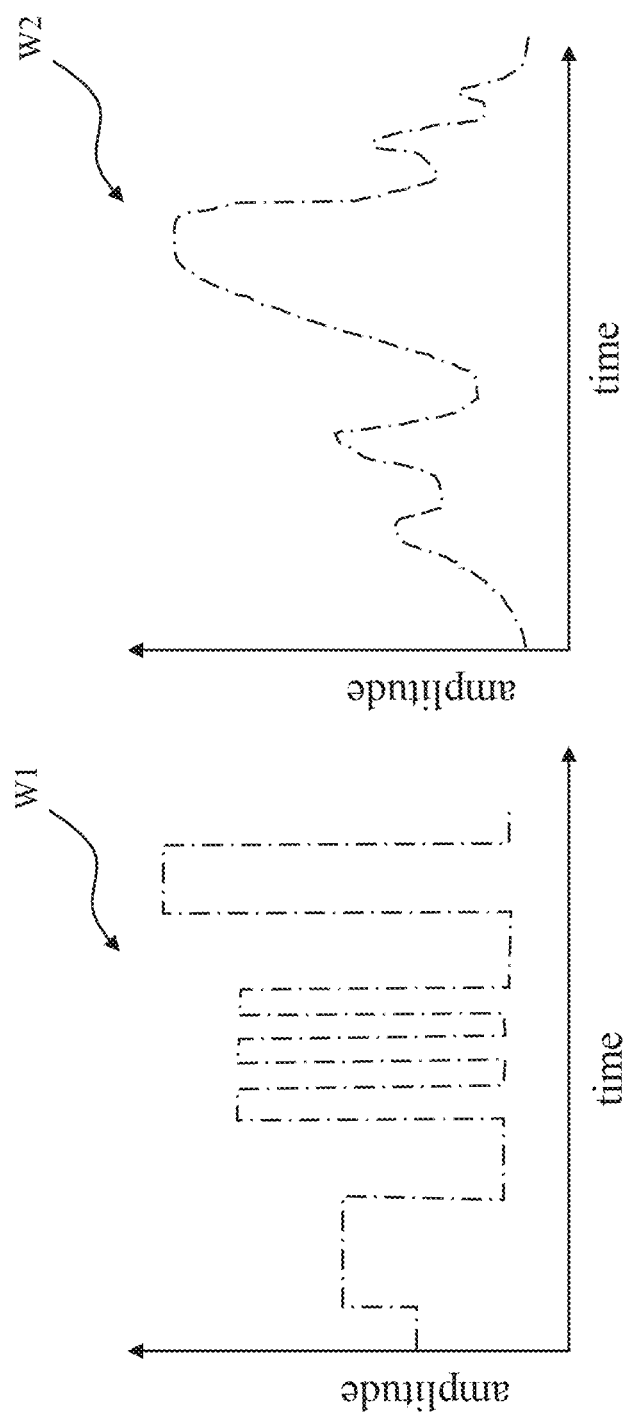

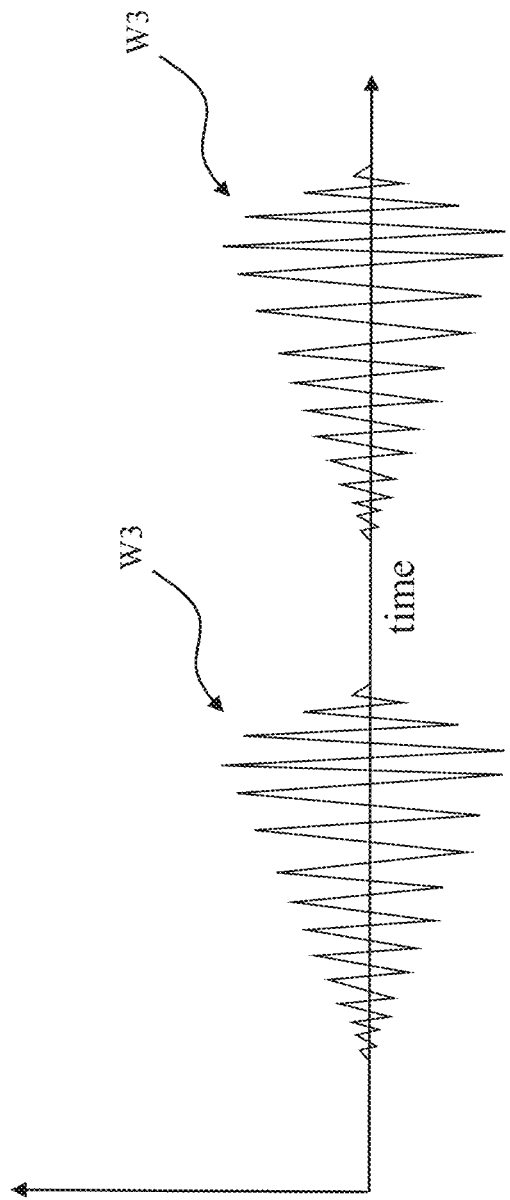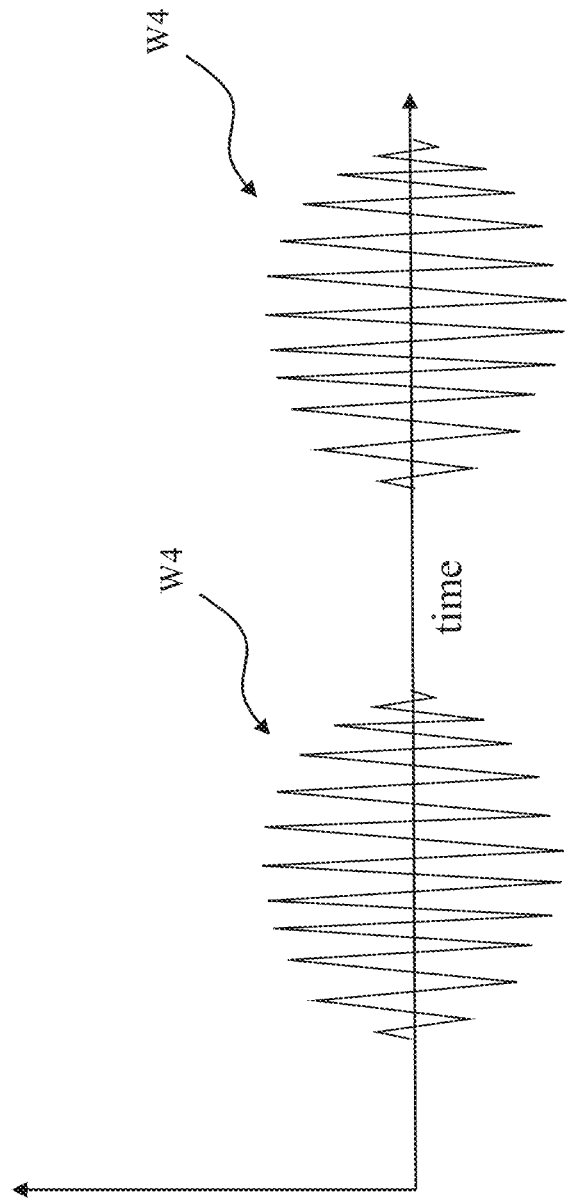

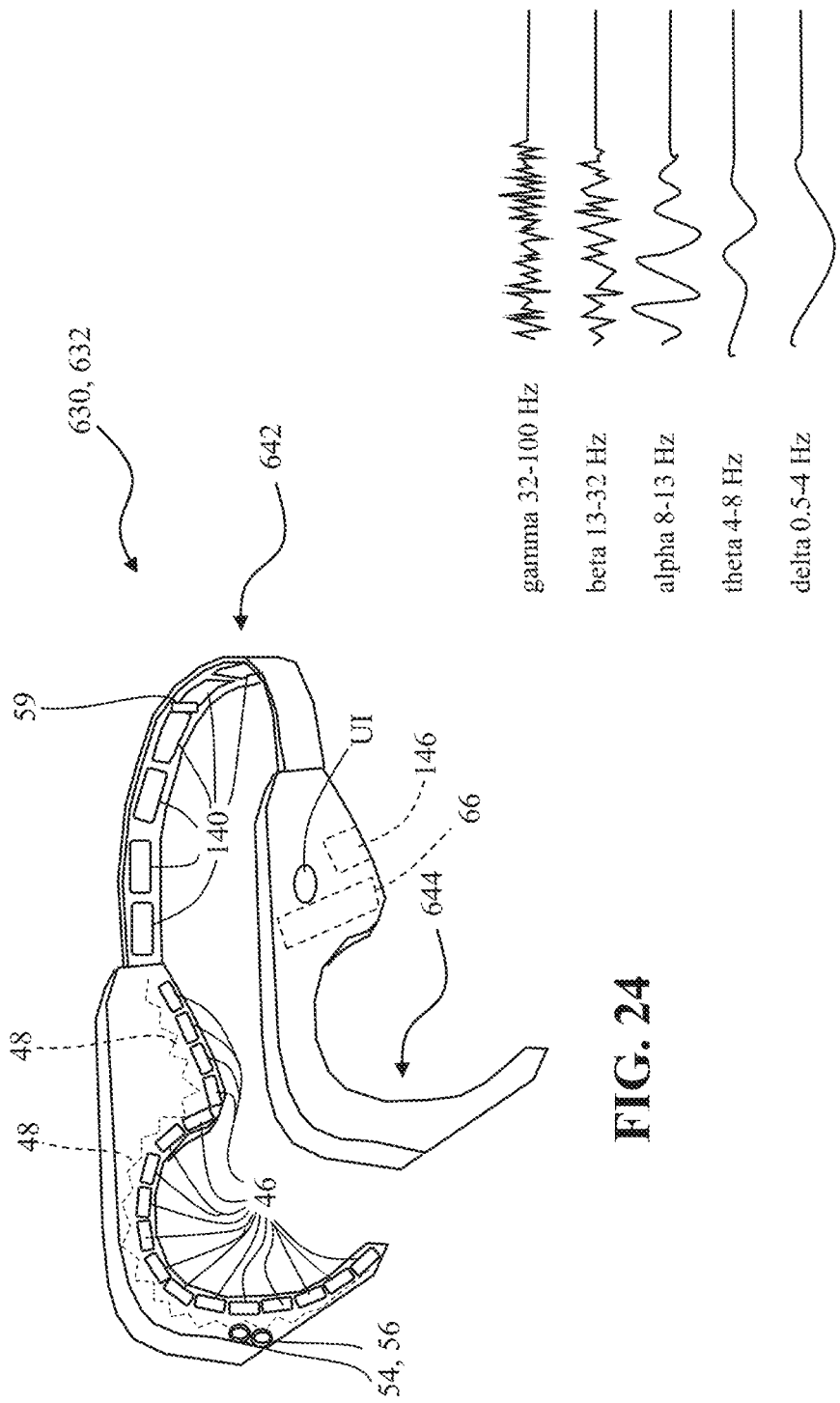

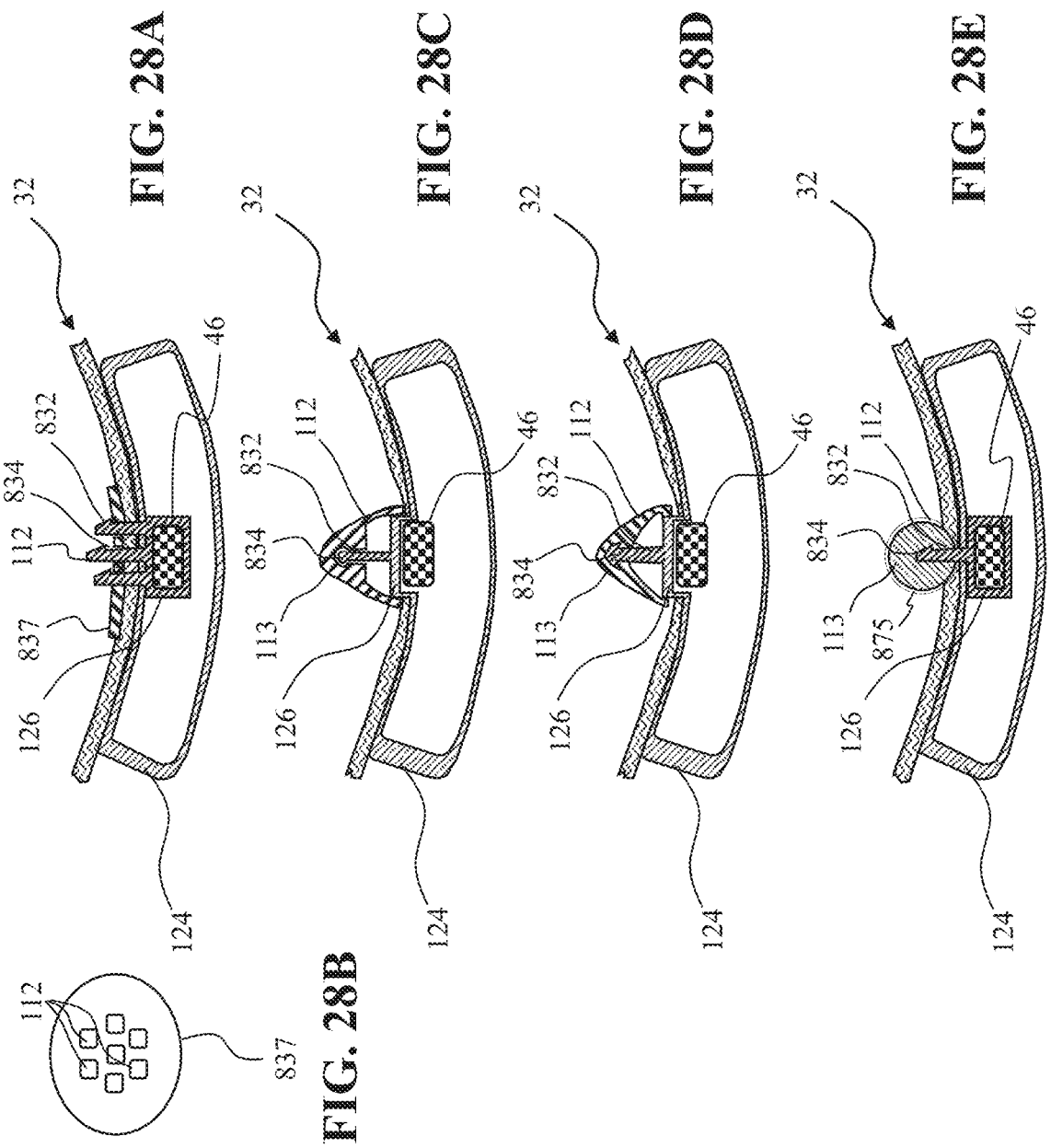

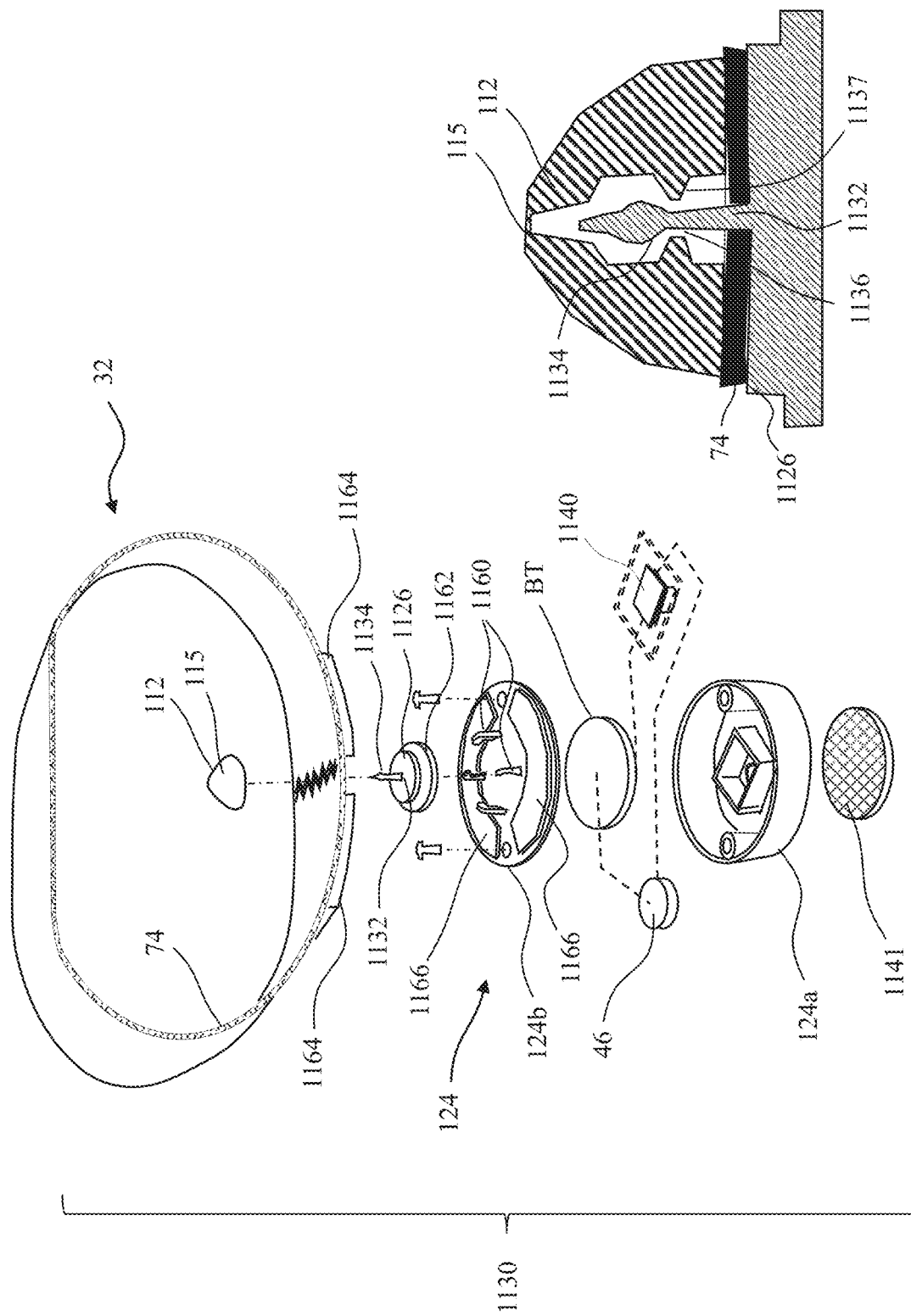

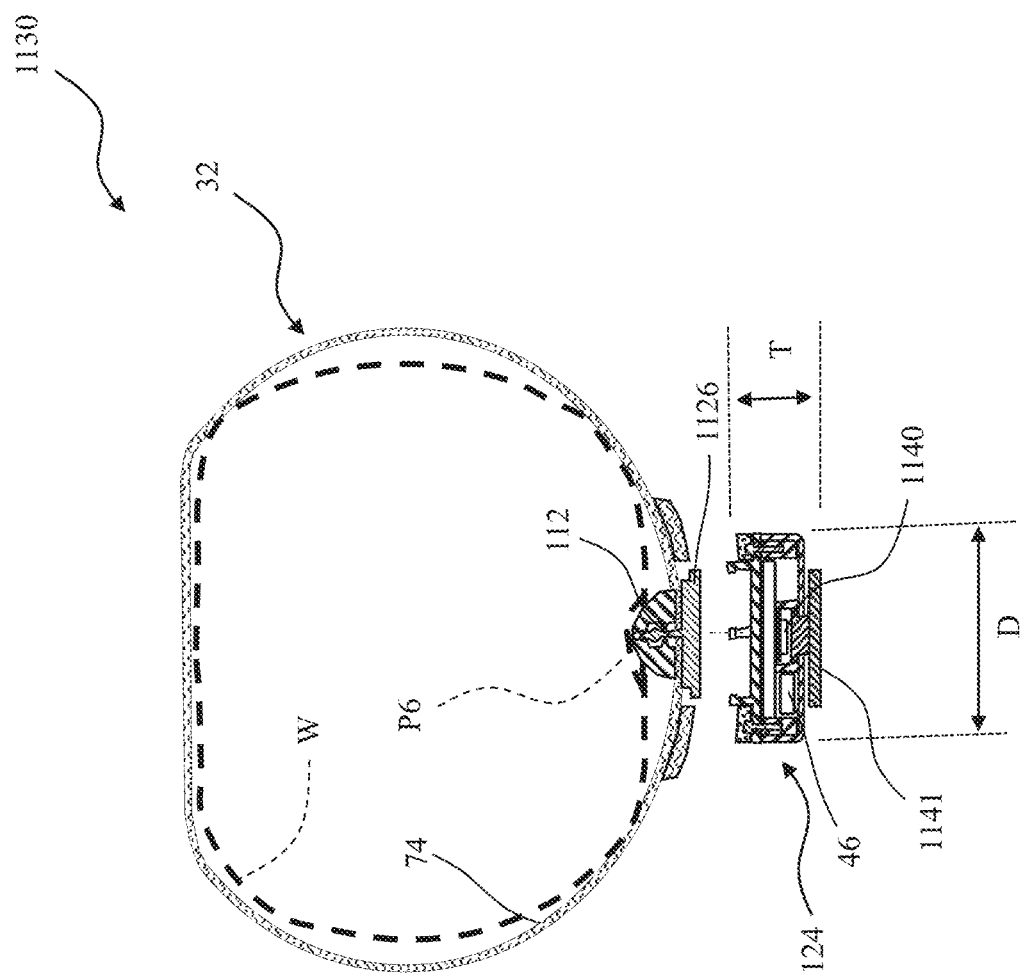

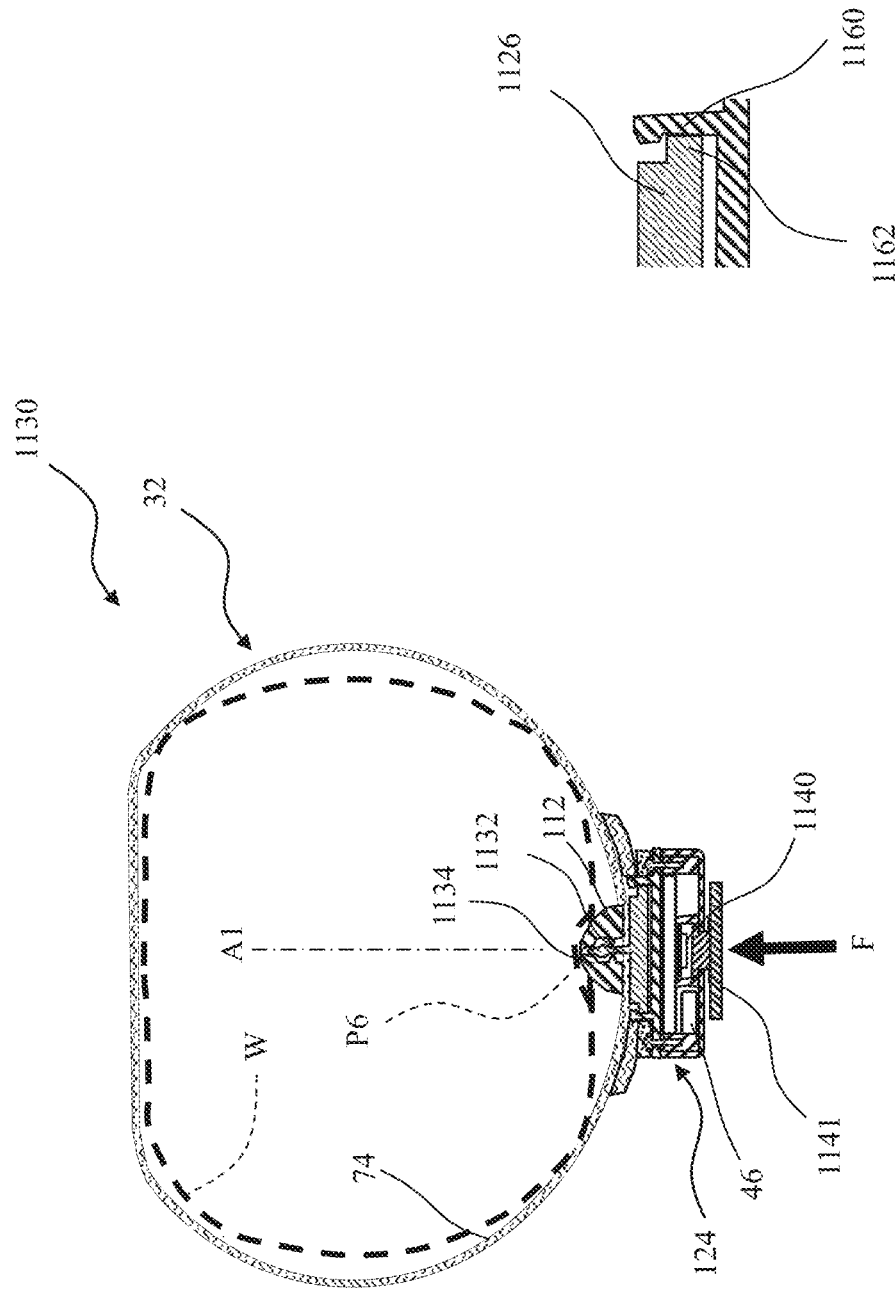

US 11,969,557 B1

WEARABLE DEVICES FOR PROVIDING PRESSURE THERAPY TO A USER

CROSS-REFERENCE TO RELATED APPLICATIONS

This application is a continuation of U.S. patent application Ser. No. 17/941,056, filed on Sep. 9, 2022, which is a divisional of U.S. patent application Ser. No. 16/984,222, filed on Aug. 4, 2020, now U.S. Pat. No. 11,478,606, which claims the benefit of U.S. Provisional Patent Application No. 62/958,383, filed on Jan. 8, 2020, and U.S. Provisional Patent Application No. 63/043,471, filed on Jun. 24, 2020. The disclosures of all of these applications are hereby incorporated herein by reference.

TECHNICAL FIELD

The present disclosure relates to wearable devices for providing therapy to a user and/or for measuring physiological parameters of the user.

BACKGROUND

Wearable devices are well known for measuring physiological parameters of a user, such as heart rate and blood pressure. Sometimes the user's heart rate and/or blood pressure measurements will change during periods of increased mental stress or anxiety. Monitoring physiological parameters are useful in indicating such changes to the user.

There is a need for providing therapy to the user in response to changes in physiological parameters, e.g., to treat stress, anxiety, nausea, etc. There is also a need for alternative wearable devices.

SUMMARY

In some embodiments, a wearable device provides pressure therapy to a user. The wearable device comprises a wearable support to be worn by the user, wherein the wearable support includes an inner flexible layer arranged to contact the user, an outer flexible layer arranged to face away from the user, and a plurality of inflatable bladders. A pump is operatively coupled to the plurality of inflatable bladders to inflate the plurality of inflatable bladders. The pump is located in an inflator housing mounted to the wearable support. A controller is coupled to the pump to control operation of the pump to inflate the plurality of inflatable bladders. A display unit includes a user interface and a display, wherein the display unit is coupled to the wearable support and is spaced from the inflator housing such that, when the wearable support is worn by the user, the user interface and display are located adjacent a top of the wearable support and the inflator housing and pump are located adjacent a bottom of the wearable support.

In some embodiments, a wearable device provides haptic therapy to a user. The wearable device comprises a wrist band to be worn by the user and one or more haptic generators arranged on the wrist band to be in proximity to an acupressure point of the user when the wrist band is worn by the user.

In some embodiments, a wearable device provides therapy to a user. The wearable device comprises a wearable support to be worn by the user. One or more haptic output devices are carried by the wearable support. A controller is operable in a training mode and a therapy mode. The controller is configured to condition the user in the training mode to elicit a desired physiological response from the user by activating the one or more haptic output devices in a predetermined pattern in the training mode. The controller is configured to provide therapy to the user in the therapy mode after conditioning the user in the training mode by activating the one or more haptic output devices in the same predetermined pattern in the therapy mode in response to input from a therapy trigger.

In some embodiments, a method provides therapy to a user using a wearable device comprising a wearable support worn by the user, one or more haptic output devices carried by the wearable support, and a therapy trigger. The method comprises initiating operation of the wearable device in a training mode to condition the user in the training mode to elicit a desired physiological response from the user. The one or more haptic output devices are activated in a predetermined pattern in the training mode. The method also comprises initiating operation of the wearable device in the therapy mode after conditioning the user in the training mode. The one or more haptic output devices are activated in the same predetermined pattern in the therapy mode in response to input from the therapy trigger.

In some embodiments, a wearable device comprises a wearable support to be worn by the user and one or more haptic output devices arranged on the wearable support to be in proximity to an acupressure point of the user when the wearable support is worn by the user. A controller is operatively coupled to the one or more haptic output devices to control the one or more haptic output devices.

In some embodiments, a method comprises placing one or more haptic output devices of a wearable support in proximity to an acupressure point of a user when the wearable support is worn by the user. The method further comprises controlling the one or more haptic output devices with a controller to provide therapy to the user.

In some embodiments, a wearable device measures blood pressure of a user. The wearable device comprises a wrist band to be worn by the user. The wrist band includes an inflatable bladder. An inflator is operatively coupled to the inflatable bladder to inflate the inflatable bladder. A blood pressure measurement unit is operatively coupled to the wrist band to measure the blood pressure of the user. A band tensioner is operatively coupled to the wrist band to tighten the wrist band on the user. A controller is operatively coupled to the inflator, the blood pressure measurement unit, and the band tensioner to coordinate operation of the inflator, the blood pressure measurement unit, and the band tensioner to take one or more blood pressure measurements.

In some embodiments, a method measures blood pressure of a user using a wearable device comprising a wrist band including an inflatable bladder, an inflator operatively coupled to the inflatable bladder to inflate the inflatable bladder, a blood pressure measurement unit operatively coupled to the wrist band, and a band tensioner operatively coupled to the wrist band. The method comprises tensioning the wrist band with the band tensioner to a preset tension. The inflatable bladder is inflated to a pressure above systolic pressure for the user while the wrist band is under tension. The method also comprises capturing one or more pressure measurements while releasing pressure from the inflatable bladder.

In some embodiments, a wearable device measures blood pressure of a user and employs one or more haptic generators to indicate to the user that a blood pressure measurement is to be taken. The wearable device comprises a wrist band configured to be worn by the user. The wrist band includes an inflatable bladder. The one or more haptic generators, which are different than the inflatable bladder, are carried by the wrist band. An inflator is operatively coupled to the inflatable bladder to inflate the inflatable bladder. A blood pressure measurement unit is operatively coupled to the wrist band to measure the blood pressure of the user. A controller is operatively coupled to the one or more haptic generators, the inflator, and the blood pressure measurement unit. The controller is configured to activate the one or more haptic generators to indicate to the user that the inflatable bladder is to be inflated and a blood pressure measurement is to be taken.

In some embodiments, a method comprises activating one or more haptic generators to indicate to the user that an inflatable bladder is to be inflated and a blood pressure measurement is to be taken.

In some embodiments, a wearable device measures blood pressure of a user with a first blood pressure measurement unit and a second blood pressure measurement unit. The first blood pressure measurement unit comprises an inflatable bladder, an inflator operatively coupled to the inflatable bladder to inflate the inflatable bladder, a valve coupled to the inflator, and a pressure sensor. The second blood pressure measurement unit comprises one or more optical sensors and one or more light sources. A controller is operatively coupled to the first blood pressure measurement unit and the second blood pressure measurement unit. The controller operates in a normal mode to take one or more blood pressure measurements of the user with the second blood pressure measurement unit. The controller operates in a calibration mode to take one or more blood pressure measurements with the first blood pressure measurement unit to calibrate the second blood pressure measurement unit.

In some embodiments, a method measures blood pressure of a user using a wearable device that carries a first blood pressure measurement unit and a second blood pressure measurement unit. The method comprises capturing one or more blood pressure measurements of the user in a normal mode with the second blood pressure measurement unit and capturing one or more blood pressure measurements of the user in a calibration mode with the first blood pressure measurement unit to calibrate the second blood pressure measurement unit.

In some embodiments, a wearable device provides therapy to a user. The wearable device comprises a wrist band to be worn by the user. A projection protrudes from the wrist band to engage an acupressure point of the user when the wrist band is worn by the user. One or more haptic output devices are arranged on the wrist band to provide haptic therapy to the acupressure point of the user when the wrist band is worn by the user, the one or more haptic output devices arranged to produce vibrations through the projection to be felt by the user during the haptic therapy. A controller is operatively coupled to the one or more haptic output devices to control the one or more haptic output devices.

In some embodiments, a method provides therapy to a user using a wearable device including a wrist band worn by the user, one or more haptic output devices carried by the wrist band, and a projection extending from the wrist band. The method comprises placing the projection adjacent to acupressure point Pericardium 6 (P6), placing the one or more haptic output devices in proximity to the acupressure point P6 of the user when the wearable support is worn by the user, and controlling the one or more haptic output devices to provide haptic therapy to the user.

In some embodiments, a wearable device provides therapy to a user. The wearable device comprises a wrist band to be worn by the user. A projection protrudes from the wrist band to engage acupressure point Pericardium 6 of the user when the wrist band is worn by the user. A first haptic output device is arranged on the wrist band to provide haptic therapy to the acupressure point Pericardium 6 of the user when the wrist band is worn by the user. The first haptic output device is arranged to produce vibrations through the projection to be felt by the user during the haptic therapy. A first controller is operatively coupled to the first haptic output device to control the first haptic output device. A second haptic output device is arranged on the wrist band to provide haptic therapy to the acupressure point San Jiao 5 (also referred to as triple warmer 5) of the user when the wrist band is worn by the user. The second haptic output device is arranged to produce vibrations to be felt by the user during the haptic therapy. A second controller is operatively coupled to the second haptic output device to control the second haptic output device.

In some embodiments, a method provides therapy to a user using a wearable device including a wrist band worn by the user, a first haptic output device carried by the wrist band, a second haptic output device carried by the wrist band, and first and second projections extending from the wrist band. The method comprises placing the first projection adjacent to acupressure point Pericardium 6 and placing the second projection adjacent to acupressure point San Jiao 5. The method also comprises placing the first haptic output device in proximity to the acupressure point Pericardium 6 of the user when the wearable support is worn by the user and placing the second haptic output device in proximity to the acupressure point San Jiao 5 of the user when the wearable support is worn by the user. The first and second haptic output devices are controlled to provide haptic therapy to the user.

BRIEF DESCRIPTION OF THE DRAWINGS

FIG. 1 is a perspective view of a wearable device comprising a wrist band and display unit.

FIG. 2 is a view of a display.

FIG. 7 is a graph of a waveform for providing therapy to a user.

FIG. 8 is a graph of another waveform for providing therapy to a user.

FIGS. 8A and 8B are examples of repeating waveforms.

FIG. 24 is a perspective view of a wearable device including a head band and a pair of ear pieces.

FIG. 25 is a graph of brain waves.

FIG. 28A is a cross-sectional view of an alternative connection for a projection and a housing to connect the projection and the housing to a wearable support.

FIG. 28B is a top view of an array of projections.

FIG. 28C is a cross-sectional view of an alternative connection for a projection and a housing to connect the projection and the housing to a wearable support.

FIG. 28D is a cross-sectional view of an alternative connection for a projection and a housing to connect the projection and the housing to a wearable support.

FIG. 28E is a cross-sectional view of an alternative connection for a projection and a housing to connect the projection and the housing to a wearable support.

FIG. 38 is an exploded, perspective view of a wearable device including a wrist band and a haptic generator for being placed against an acupressure point of a user during therapy, wherein the haptic generator is located in a housing that can be releasably coupled to the wrist band.

FIG. 38A is a cross-sectional view of a projection, base, and post of the wearable device of FIG. 38.

FIG. 39A is a cross-sectional view of the wearable device of FIG. 38 showing the housing separated from the wrist band.

FIG. 39B is a cross-sectional view of the wearable device of FIG. 38 showing the housing coupled to the wrist band.

FIG. 39C is a cross-sectional view illustrating connection of snap elements to facilitate coupling of the housing to the wrist band.

DETAILED DESCRIPTION

Figure 3:
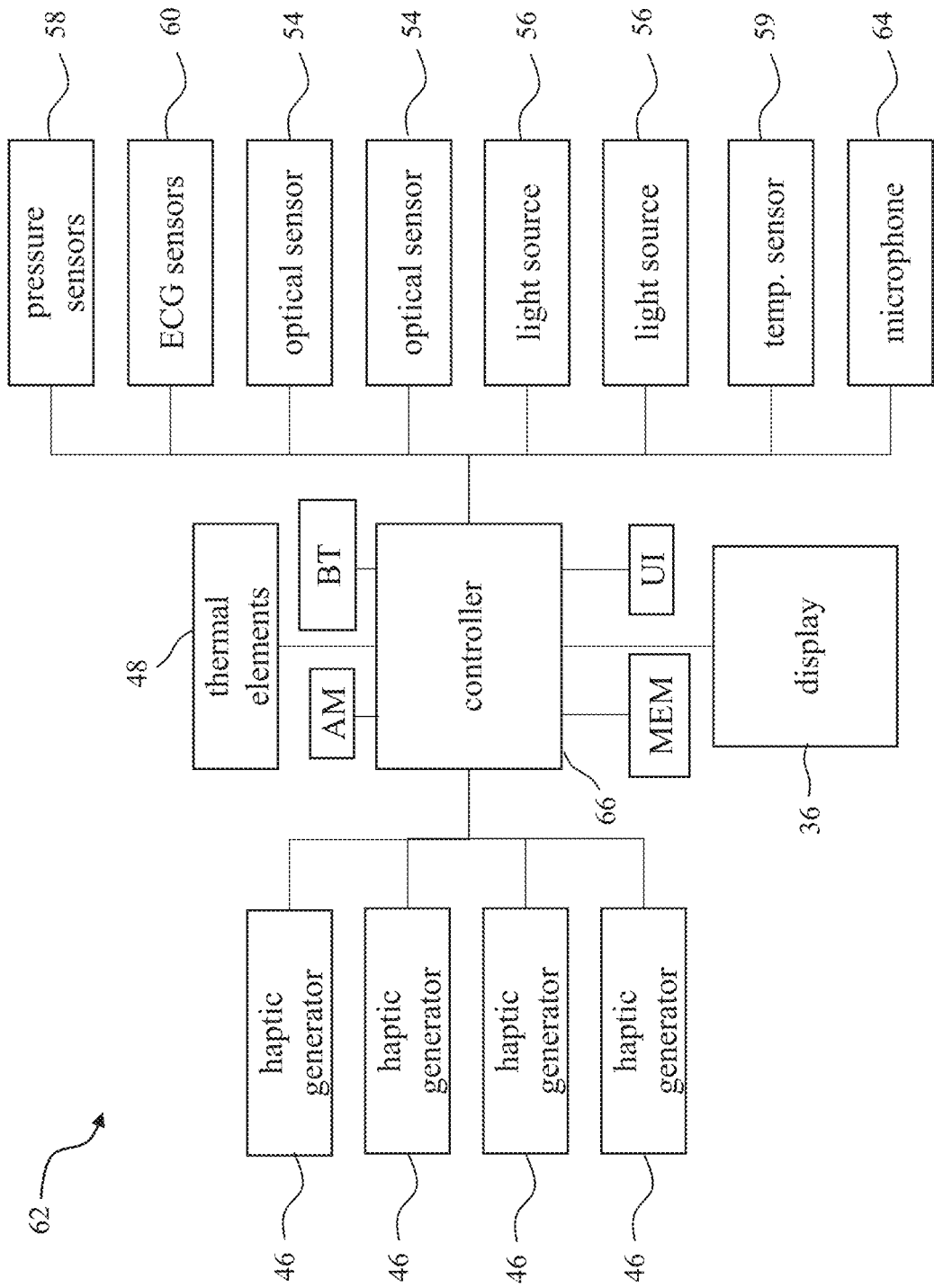
FIG. 3 is a block diagram of a control system for the wearable device of FIG. 1.

Referring to FIG. 1, a wearable device 30 is shown for providing therapy to a user and for measuring/monitoring one or more physiological parameters of the user. The therapy that can be provided by the wearable device 30 includes haptic therapy and/or heat therapy. Haptic therapy may include vibration therapy and/or pressure therapy, as described further below. The physiological parameters that can be measured and monitored include heart rate, skin temperature, blood pressure, electroencephalographic (EEG) readings, electrocardiogram (ECG) readings, blood oxygen, combinations thereof, and the like.

The wearable device 30 comprises a wearable support 32 configured to be worn by the user. In the version shown in FIG. 1, the wearable support 32 is a wrist band to be worn on a user's wrist W, but the wearable support 32 may be other forms of wearable supports that enable the wearable device 30 to be worn by the user, such as a head band, an arm band, a leg band, an ear piece, a garment (e.g., shirt, shorts, pants, dresses, undergarments, socks, shoes), or the like. The wrist band shown in FIG. 1 may be formed of inelastic, elastic, and/or semi-elastic materials, or combinations thereof. Examples of suitable materials include, but are not limited to, vinyl, silicone, non-woven fabric, woven fabric, Tyvek® plastic, Neoprene, leather, faux leather, and the like.

In some versions, a display unit 34 is coupled to the wearable support 32. The display unit 34 may include a housing that carries a display 36 (see also FIG. 2) and/or a user interface UI for interacting with the user. The display 36 may be a liquid crystal display (LCD), a light emitting diode (LED) display, organic light emitting diode (OLED) display, or other type of display. The user interface UI may include a touch screen (e.g., capacitive touch screen, etc.), sensors (e.g., touch sensors, gesture sensors, etc.), buttons, or other forms of user input devices. In FIG. 1, the user interface UI includes a capacitive touch screen 38, a capacitive sensor 40 for detecting a user's finger touch for input, and a push button 42. The display unit 34 may be a watch unit, such as an Apple Watch, Samsung Watch, or other form of smart watch unit.

The wearable support 32 is coupled to the display unit 34 via one or more connectors 44. The display unit 34 may carry one or more batteries BT (see FIG. 3) for providing power to the display 36 and/or other electronic components of the wearable device 30. Batteries BT may also be provided on the wearable support 32. In some versions, the connectors 44 provide electrical contact between the batteries BT of the display unit 34 and the electronic components carried by the wearable support 32. Examples of suitable connectors and methods for connecting the display unit 34 to the wearable support 32 are shown in U.S. Pat. No. 10,058,148 to Wittenberg et al., entitled "Attachment Mechanism Architectures For A Watch Band," which is hereby incorporated herein by reference and U.S. Pat. No. 10,448,711 to Kallman et al., entitled "Accessory Contacts," which is hereby incorporated herein by reference. In some versions, the wearable support 32 is worn by the user without any display unit, or more than one display unit 34 may be coupled to the wearable support 32.

A haptic therapy system is coupled to the wearable support 32. The haptic therapy system includes one or more haptic output devices carried by the wearable support. The haptic output devices may comprise haptic generators 46 carried by the wearable support 32. The haptic generators 46 shown in FIG. 1 are haptic actuators in the form of vibration motors that generate vibrations that can be felt/sensed by the user. Such vibration motors may be electric DC vibration motors that have an eccentric mass that is rotated to generate such vibrations in response to supplied electrical current. The haptic generators 46 may also be piezoelectric actuators that vibrate when supplied with electrical current or may include shape memory materials that change shape when heated and provide associated haptic output to the user. In some versions, the piezoelectric actuators may be configured to generate ultrasonic output that can be felt/sensed by the user. Other forms of haptic output devices, described further below, may also be used. Combinations of vibration motors, piezoelectric actuators, other haptic generators, and/or other haptic output devices may be used. In some versions, the haptic generators 46 are vibration motors that rotate in a range of rotations per minute (RPM) or that operate at a predetermined frequency. For instance, some of the haptic generators 46 may operate in a range of from 100 to 10,000 RPM, from 1,000 to 5,000 RPM, from 1,500 to 4,500 RPM, or the like. Some of the haptic generators 46 may operate at a frequency of from 5 to 100 Hz, from 10 to 80 Hz, from 30 to 80 Hz, from 40 to 70 Hz, or the like. Some of the haptic generators 46 may operate above 10,000 RPM or above 100 Hz, such as from 100 Hz to 200 Hz. In some cases, the haptic actuators described below that are used near a user's head may operate at lower frequencies than those that are used on a user's wrist, for example.

In the version shown in FIG. 1, there are four haptic generators 46 embedded into the wearable support 32, beneath an interface surface 50 of the wearable support 32. In other versions, the haptic generators 46 may be disposed on the interface surface 50 for direct contact with the user. A single haptic generator 46, or multiple haptic generators 46 could be employed. Suitable haptic generators 46 include, for example, 3.0V DC micro coin vibration motors 1030 from BestTong, available at www.Amazon.com. Other suitable haptic generators 46 and controls for the haptic generators 46 include those available from Boreas Technologies Inc. located in Bromont, Quebec (e.g., PowerHap actuators, part no. 1204H018V060 and associated piezoelectric drivers available in the BOS1901-Kit). The haptic generators 46 are intended to provide haptic therapy (also referred to as vibration therapy) to the user and/or to provide the user with alerts, notifications, and the like, as described further below.

A temperature therapy system is coupled to the wearable support 32. The temperature therapy system comprises one or more thermal elements 48 carried by the wearable support 32. The thermal elements 48 may include heating elements and/or cooling elements. The thermal elements 48 may be small coils, ribbons, or strips of wire that generate heat in response to supplied electrical current, and/or may be a fluid cooling circuit, thermoelectric elements (e.g., coolers that operate on the Peltier effect), or the like that cool a surface. Other forms of thermal elements may also be used. In the version shown in FIG. 1, there are four thermal elements 48 embedded into the wearable support 32, beneath the interface surface 50 of the wearable support 32. In other versions, the thermal elements 48 may be disposed on the interface surface 50 for direct contact with the user. A single thermal element 48 or multiple thermal elements 48 could be employed. The thermal elements 48 are intended to provide thermal therapy to the user by warming or cooling the user's skin surface via the wearable support 32.

A measuring system 52 is coupled to the wearable support 32. The measuring system 52 comprises one or more measuring devices for measuring one or more physiological parameters of the user. In the version shown, the measuring devices include one or more optical sensors 54 (e.g., photodiodes or photodetectors) and one or more light sources 56 for measuring heart rate and/or blood pressure using photoplethysmography (PPG). The light sources 56 emit light onto a tissue of the user (e.g., user's wrist W, behind ear, etc.) and the optical sensors 54 measure the reflected light from the tissue. The reflected light is proportional to blood volume variations. The light sources 56 may include one or more infrared light emitting diodes (IR-LED) and/or one or more green light emitting diodes (G-LED). Blood volume changes can be measured (calculated) based on the amount of the reflected light using conventional PPG measuring techniques. The optical sensors 54 and the light sources 56 may be mounted in a sensor housing 57. Suitable sensors and light sources for measuring heart rate or other physiological parameters are disclosed in U.S. Patent Application Publication No. 2016/0058375 to Rothkopf, entitled "Wearable Electronic Device," which is hereby incorporated herein by reference.

Other methods of measuring heart rate and/or blood pressure are also contemplated. In some versions, blood pressure is measured using a combination of one or more pressure sensors 58, one or more electrocardiogram (ECG) sensors 60, and the one or more optical sensors 54. See, for example, the method of measuring blood pressure described in U.S. Pat. No. 8,086,301 to Cho et al., entitled, "Method And Apparatus For Cufflessly And Non-Invasively Measuring Wrist Blood Pressure In Association With Communication Device," hereby incorporated by reference herein. Also see, for example, U.S. Pat. No. 8,585,605 to Sola I Caros et al., entitled "Method And Apparatus For A Continuous Non-Invasive And Non-Obstructive Monitoring Of Blood Pressure," hereby incorporated herein by reference. In some of these methods, ECG signals are generated by an opposing finger of the user making contact with one of the ECG sensors 60. See, for example, the ECG sensor 60 on an outer surface of the wearable support 32 for receiving the opposing finger of the user (on the hand which does not include the wearable device 30). The pressure sensors 58 and the other ECG sensors 60 may be mounted in the sensor housing 57.

Referring to FIG. 3, a control system 62 is shown for the wearable device 30. The control system 62 includes a controller 66 that is operatively coupled to the display unit 34 (and the display 36 and user interface UI thereof), the haptic generators 46, the thermal elements 48, the optical sensors 54, the light sources 56, the pressure sensors 58, the ECG sensors 60, and any other electronic components described herein that transmit signals to and/or receive signals from the controller 66. The controller 66 may include one or more microprocessors, microcontrollers, field programmable gate arrays, systems on a chip, volatile or nonvolatile memory, discrete circuitry, and/or other hardware, software, or firmware that is capable of carrying out the functions described herein. As previously described, when the connectors 44 engage the display unit 34, power and data connections are made between the display unit 34 and the wearable support 32. In some versions, the controller 66 is part of the display unit 34. In some versions, the controller 66 is part of the wearable support 32. In some versions, the controller 66 may comprise a controller on the wearable support 32 and a controller on the display unit 34. Other locations for the controller 66 are also contemplated. The user interface UI is operatively coupled to the display 36 to change images on the display 36 and to also control the other electronic components described herein.

Figure 4:
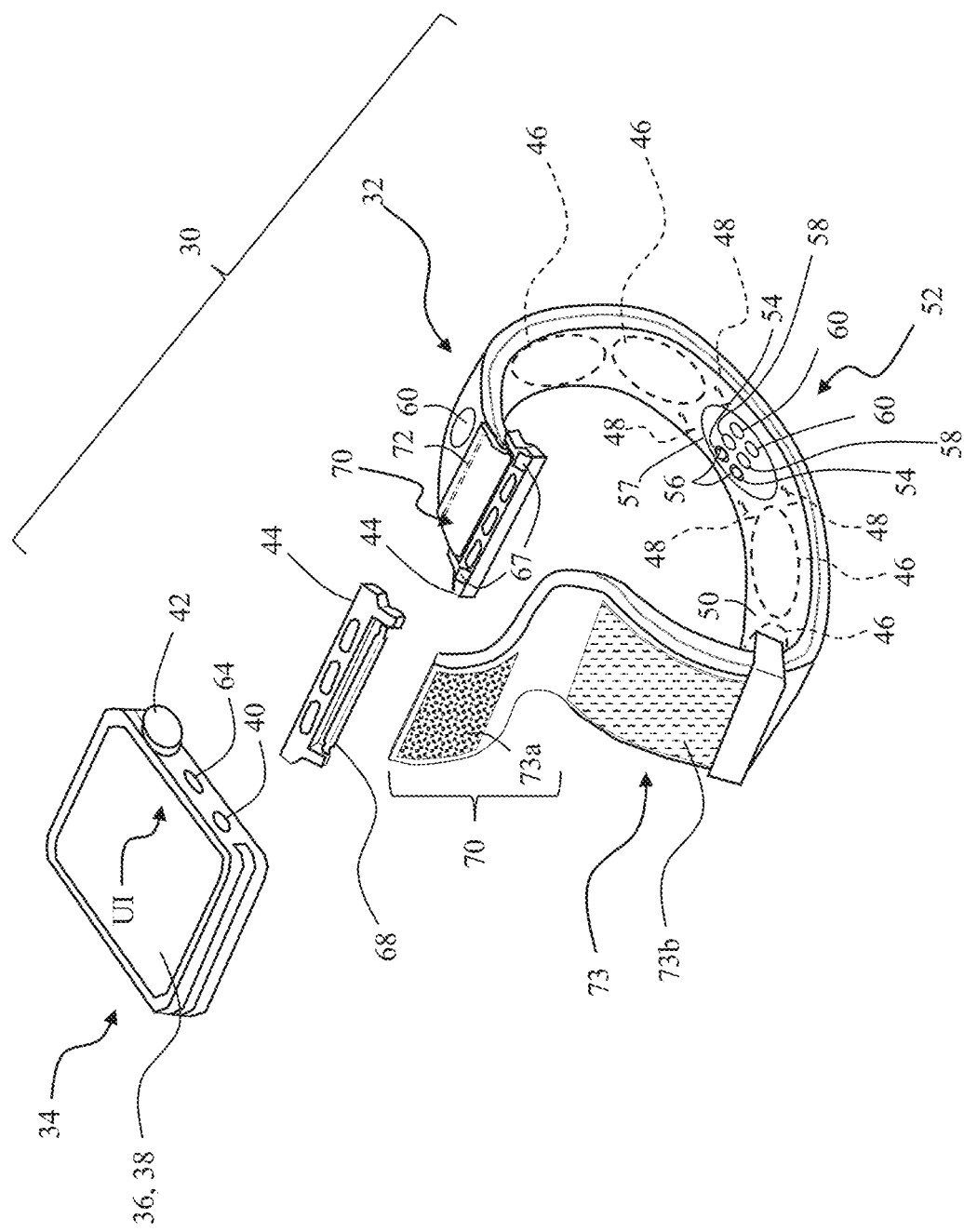
FIG. 4 is a partially exploded view of the wearable device of FIG. 1 illustrating connectors for connecting the wrist band to the display unit.

FIG. 4 shows one of the connectors 44 exploded from the wearable support 32 and the display unit 34. As previously mentioned, the connectors 44 may provide power and data connections between the display unit 34 and the electronic components carried by the wearable support 32. This may be accomplished, for example, by contacts 67 located on the connectors 44 that establish connections (power, data, etc.) between the display unit 34 and the electronic components carried by the wearable support. The wearable support 32 may also comprises an identification device ID (see FIG. 5) that identifies the particular wearable support 32 that is connected to the display unit 34. The identification device ID may comprise a radio frequency identification (RFID) tag, non-volatile memory, other electronic storage device, or the like, that is configured to transmit/output a unique identifier associated with the wearable support 32 to the controller 66 when the wearable support 32 is connected to or in proximity to the display unit 34. The unique identifier may indicate a type of wearable support, a part no., a model no., or the like to the controller 66. The controller 66 may be in communication with a database or look-up table stored in the memory MEM, or otherwise accessible by the controller 66, that associates the unique identifier with the wearable support 32 and/or the controller 66 may compute an algorithm to determine the identification of the wearable support 32 based on the unique identifier.

Each connector 44 includes a roller 68 around which a portion 70 of the wearable support 32 passes. On one end, the portion 70 is wrapped around the roller 68 and then fixed (see stitches 72), or otherwise permanently fastened to the remainder of the wearable support 32. On the opposing end, the portion 70 is wrapped around the roller 68 and a releasable fastening system 73 is employed to releasably attach the portion 70 to the remainder of the wearable support 32. This facilitates tightening and loosening of the wearable support 32, depending on how much of the portion 70 is pulled around the roller 68. The releasable fastening system may include hook and loop type fasteners (see, for example, hooks 73*a* and loops 73*b*), snaps, buttons, latches/catches, adjusters, or the like. The wearable support 32 may also be permanently attached to the display unit 34 at both ends or may comprise more than one releasable fastening system.

Figure 5:
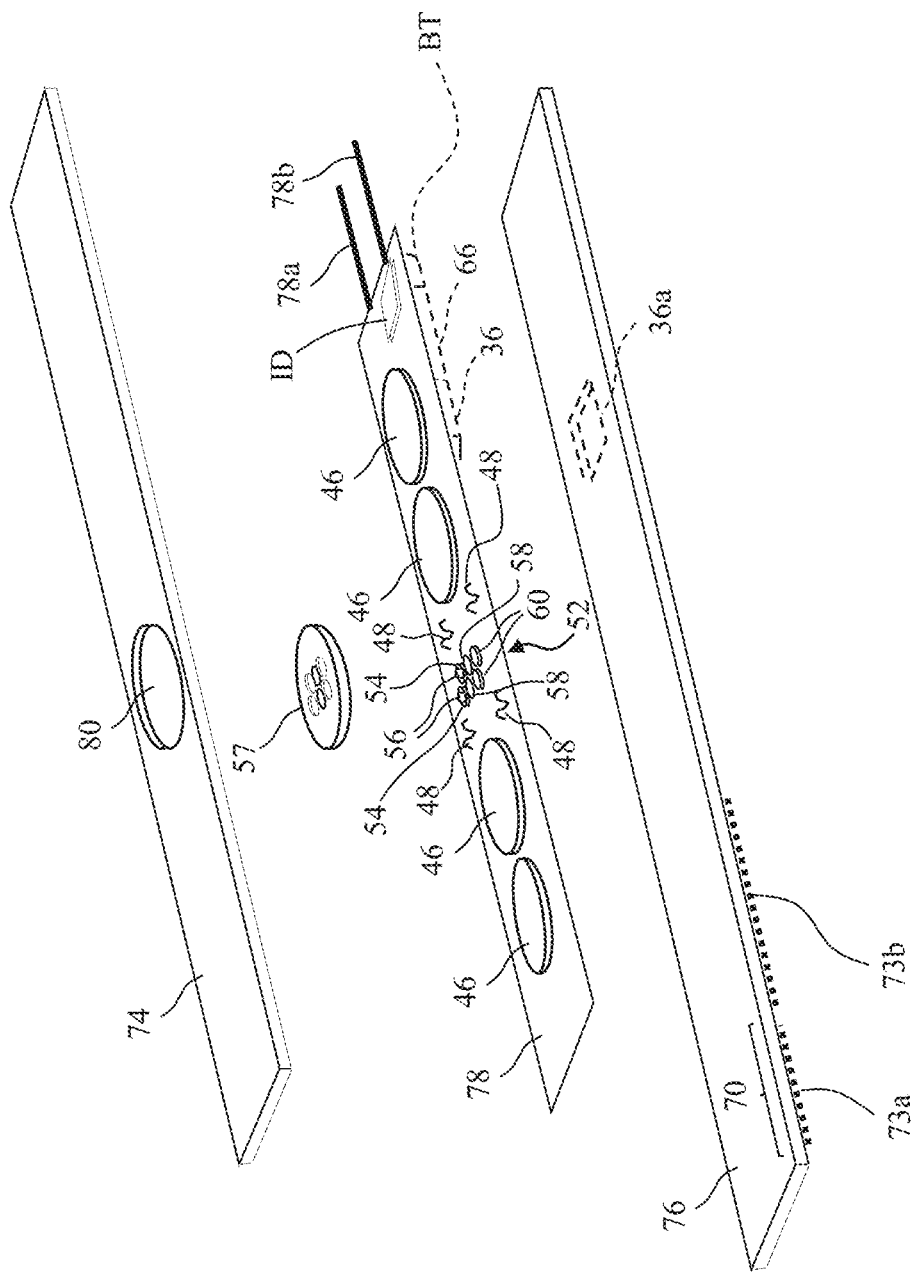
FIG. 5 is an exploded perspective view of the wrist band of FIG. 1.
Figure 6:
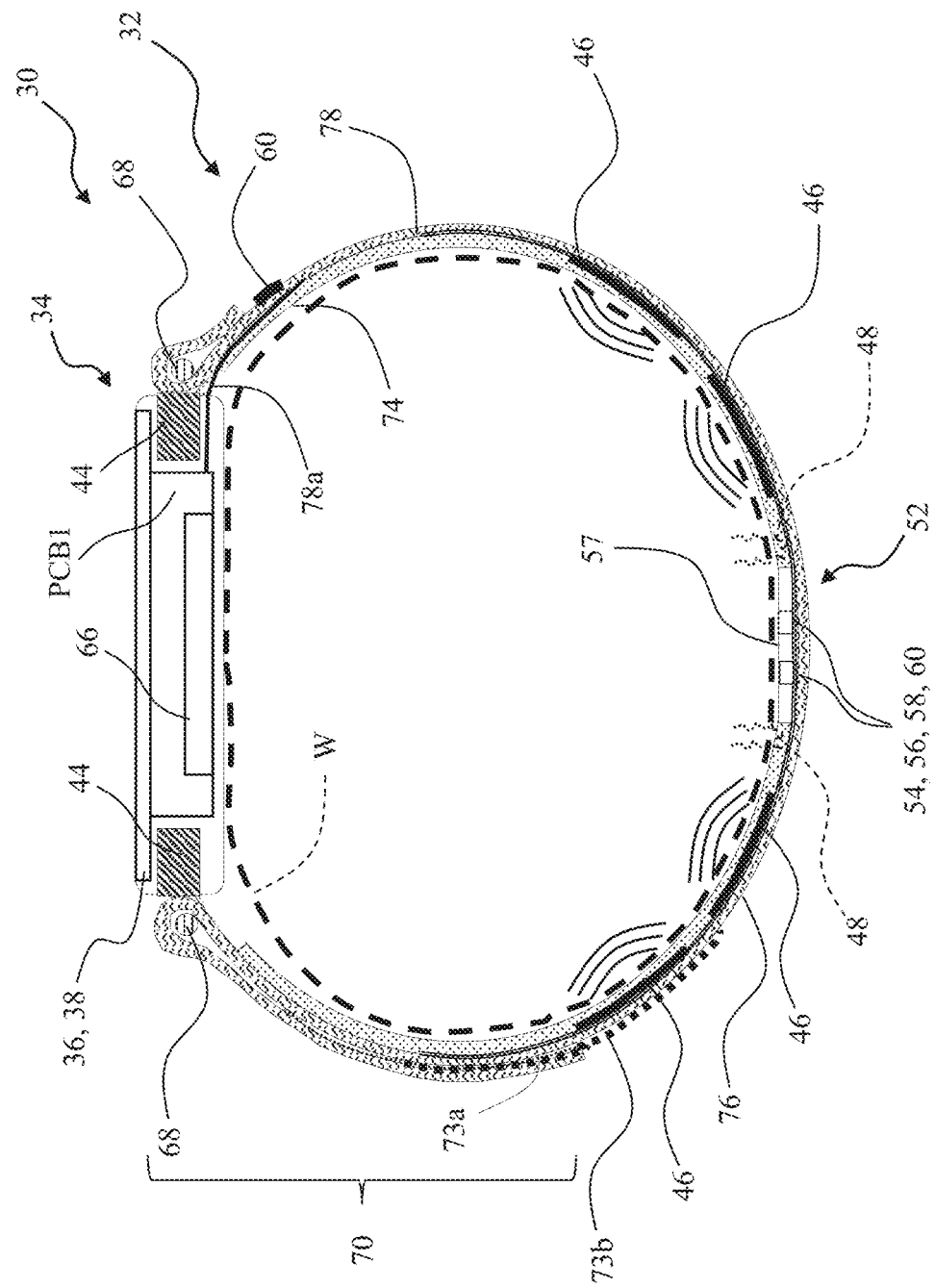
FIG. 6 is a cross-sectional view of the wearable device of FIG. 1.

Referring to FIG. 5, the wearable support 32 includes a first flexible layer 74, a second flexible layer 76, and a flex circuit 78 disposed between the first flexible layer 74 and the second flexible layer 76. The wearable support 32 may include one or more layers, that are any suitable combination of flexible, inflexible, semi-flexible, elastic, semi-elastic, and/or inelastic. The one or more haptic generators 46, thermal elements 48, sensors 54, 58, 60, lights sources 56, and identification device ID are disposed on the flex circuit 78 between the first flexible layer 74 and the second flexible layer 76. The flex circuit 78 comprises power and/or data cables 78*a*, 78*b* that connect the flex circuit 78 and the electronic components carried on the flex circuit 78 to the display unit 34 through any suitable connection technique to provide communication (power, data, etc.) between the flex circuit 78 and the display unit 34 (e.g., between the flex circuit 78 and the controller 66). The flex circuit 78 acts as a flexible circuit board that provides suitable electrical power and data connections to the components it carries, e.g., to the haptic generators 46, the thermal elements 48, the sensors 54, 58, 60, the light sources 56, the identification device ID, and the like. FIG. 6 shows one of the cables 78*a* extending from the flex circuit 78 to a printed circuit board PCB1 in the display unit 34. In the version shown, the controller 66 is mounted to the printed circuit board PCB1, along with the one or more batteries BT. The haptic generators 46, the thermal elements 48, the sensors 54, 58, 60, the light sources 56, and the identification device ID may be attached to the flex circuit 78 so that they are able to transmit/receive signals to/from the controller 66 via the cables 78a, 78b, wireless communication, or through any other suitable connections.

In some versions, the controller 66 and/or the one or more batteries BT may also be mounted to the flex circuit 78 (see phantom lines in FIG. 5). In this case, the cables 78a, 78b may connect to the user interface UI and the display 36 located on the display unit 34. An additional, or alternative, display 36 (see phantom lines in FIG. 5) could also be attached to the flex circuit 78 and located on the wearable support 32 for viewing through the second flexible layer 76 (see phantom opening 36a).

The flex circuit 78 may be attached and fixed to the first flexible layer 74 and/or the second flexible layer 76 via adhesive, stitching, ultrasonic welding, radiofrequency (RF) welding, tape, or the like, or may be loosely placed between the flexible layers 74, 76. In this case, the flexible layers 74, 76 may be attached about their outer peripheries using one or more of the attachment methods described, or using any suitable attachment method. The sensor housing 57 is mounted to the first flexible layer 74 in an opening 80 through the first flexible layer 74. The sensor housing 57 may be attached and fixed to the first flexible layer 74 using one or more of the attachment methods described, or any suitable attachment method. The first flexible layer 74, the second flexible layer 76, and the flex circuit 78 may be formed of plastic. The first flexible layer 74, the second flexible layer 76, and/or the flex circuit 78 may be formed of inelastic, elastic, or semi-elastic materials, or combinations thereof. FIG. 6 shows a cross-sectional view of the wearable device 30 generating haptic feedback and heat to a wrist of the user.

The wearable device 30 may operate in multiple modes in which haptic therapy and/or heat therapy are provided and/or in which one or more physiological parameters are measured/monitored. In some versions, the wearable device 30 is used to treat the user's anxiety or to reduce the user's stress. This may include conditioning the user in a training mode to elicit a desired physiological response from the user, such as a lowered heart rate, a lowered skin temperature, lowered blood pressure, lowered EEG signals, lowered ECG signals, a raised blood oxygen level, combinations thereof, or the like. For example, the controller 66 may be programmed to activate the one or more haptic generators 46 in a predetermined pattern in the training mode during times of low stress and/or low anxiety. The thermal elements 48 may also be activated to raise the patient's skin temperature to a predetermined temperature in the training mode. Training sessions may be initiated during periods of rest, during periods of relaxation (e.g., during massage therapy, energy therapy, or other therapeutic treatment methods), and/or during other periods in which the user has low stress/anxiety. The controller 66 may be programmed to initiate training sessions at the same time each day and/or for the same duration (e.g., in the middle of the night during restful sleep).

A training session may be initiated/stopped by the user or by a therapist via the user interface (e.g., via a start/stop training mode icon on the touchscreen or button). The training session may additionally, or alternatively, be initiated/stopped automatically in response to one or more physiological parameters of the user reaching, falling below, or exceeding certain thresholds. For example, the training session may be initiated automatically upon the controller 66 detecting the user's heart rate reaching or falling below a threshold (e.g., reaching or falling below 75 beats per minute, 70 beats per minute, etc.) and/or the training session may be automatically stopped upon the controller 66 detecting one or more physiological parameters of the user reaching, fall below, or exceeding certain thresholds (may be the same or different thresholds than those that initiate the training session). In some cases, the thresholds may be discrete values or ranges of values. The thresholds may be user-specific and/or set by the therapist based on typical values of the user. The wearable device 30 may also learn the thresholds in a learning mode that occurs before the training mode. In the learning mode, the wearable device 30 may monitor the user for a predetermined duration, e.g., one day, one week, etc. and may then define the thresholds based on averages (e.g., average heart rate, average blood pressure, etc.), based on low values, based on high values, based on predetermined offsets from the low values or the high values, based on look-up tables for similar users or groups of users, and the like.

The training mode may be carried out over several training sessions, such as two, three, four, five, or more training sessions. These training sessions may last a few seconds, one minute, two minutes, five minutes, or longer. Once training is complete, e.g., by measuring the total number, length, etc. of the training sessions and comparing to a training threshold, then the therapy mode is enabled for activation. The user or therapist may also manually enable the therapy mode once the user or therapist is satisfied that suitable training of the user has been completed. For example, training may require a predetermined number and duration of training sessions, e.g., training could require at least three training sessions and a total duration of training of at least three hours. Other suitable numbers of sessions and/or total durations to complete training are also contemplated.

FIGS. 7 and 8 illustrate digital/analog waveforms W1, W2 output by the one or more haptic generators 48 that can be repeated over and over to be learned by the user during the periods of relaxation in the training mode. The same pattern may be repeated by one haptic generator 46, or by two or more haptic generators 46 for the entire duration of the training session. Portions of the pattern may be generated by one haptic generator 46, while other portions are generated by the other haptic generators 46. These repeating patterns may be simple or complex, and generated by one or more of the haptic generators 46. Examples of simple waveforms W3, W4 being repeated are shown in FIGS. 8A and 8B. In some versions, only a single haptic generator 46 is provided. In some versions, the repeating pattern is simply the haptic generator 46 being active for a first duration, at a predefined power level, and then being inactive for a second duration (the same or different than the first duration), and this pattern being repeated over and over until the training session is complete.

The controller 66 is configured to store the predetermined pattern in the memory MEM for retrieval during the training mode and later, during the therapy mode. The predetermined pattern may comprise a repeated pattern of activation and deactivation of the one or more haptic generators 46. The repeated patterns of activation and deactivation of the one or more haptic generators 46 may mimic a breathing pattern of the user. For example, some relaxation techniques prescribe inhaling for five seconds and exhaling for five seconds to relax the user. The repeated pattern of activation and deactivation of the one or more haptic generators 46 may emulate such breathing patterns, e.g., by being active for five seconds and then inactive for five seconds. Other activation/deactivation patterns are also contemplated. In some cases, haptic output (e.g., vibrations) generated by the haptic generators 46 are consciously sensed by the user, i.e., the user can consciously feel vibrations caused by the haptic generators 46 on their skin. In some cases, the haptic output may be subtle and unable to be easily felt by the user, but nonetheless generate vibrations that can be sensed by one or more mechanoreceptors of the user.

Figure 9:
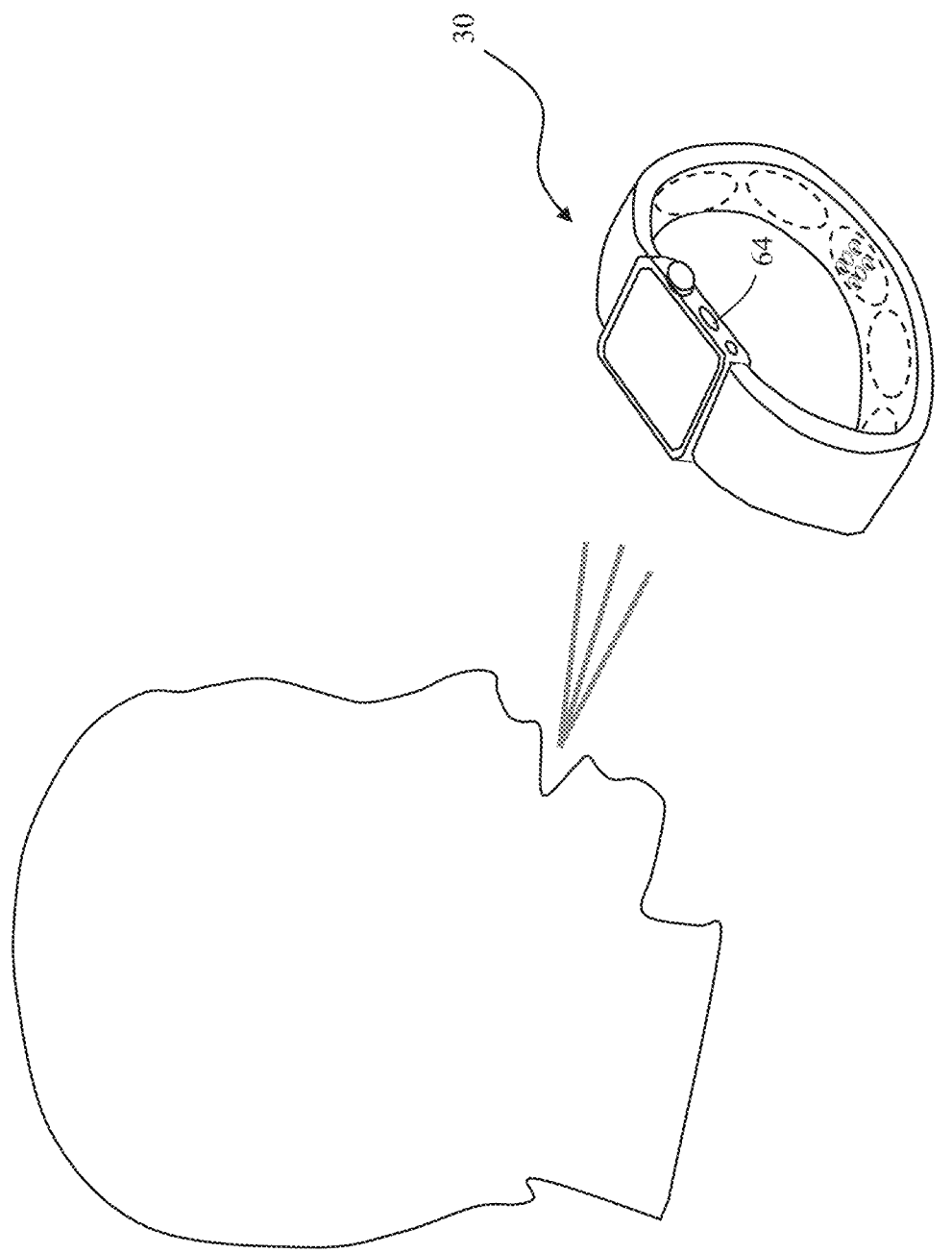
FIG. 9 is an illustration of a user speaking into a wearable device to create the waveform of FIG. 8.
Figure 10:
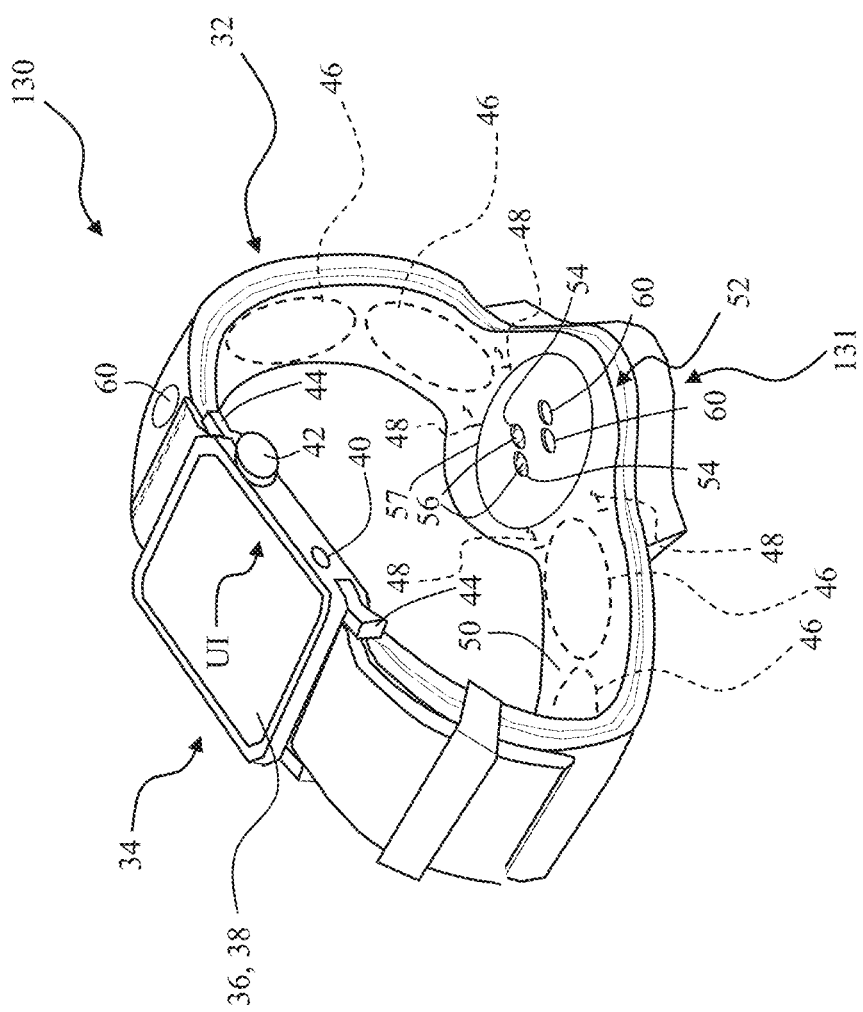
FIG. 10 is a perspective view of a wearable device comprising inflatable bladders.
Figure 11:
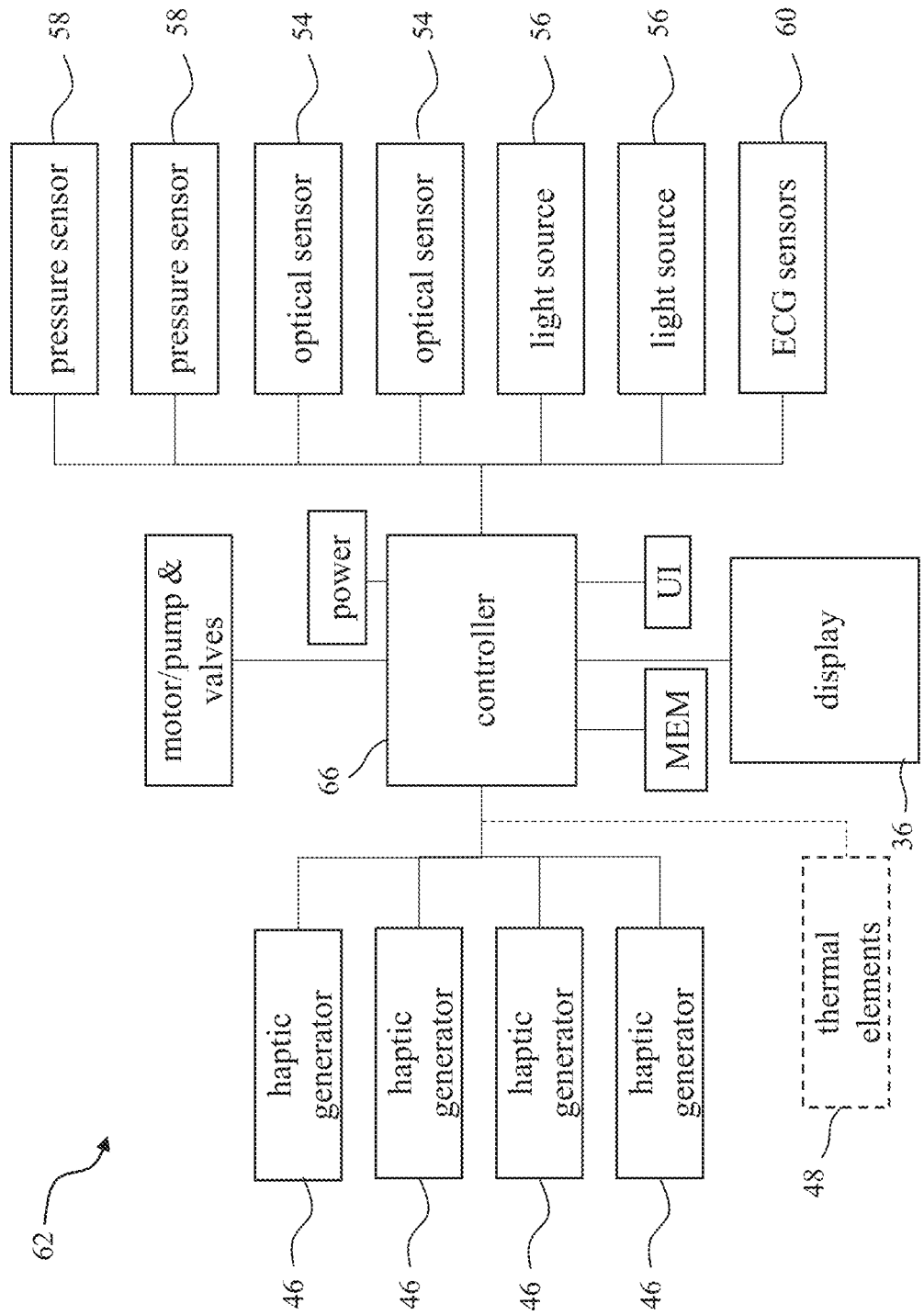
FIG. 11 is a block diagram of a control system for the wearable device of FIG. 10.
Figure 12:
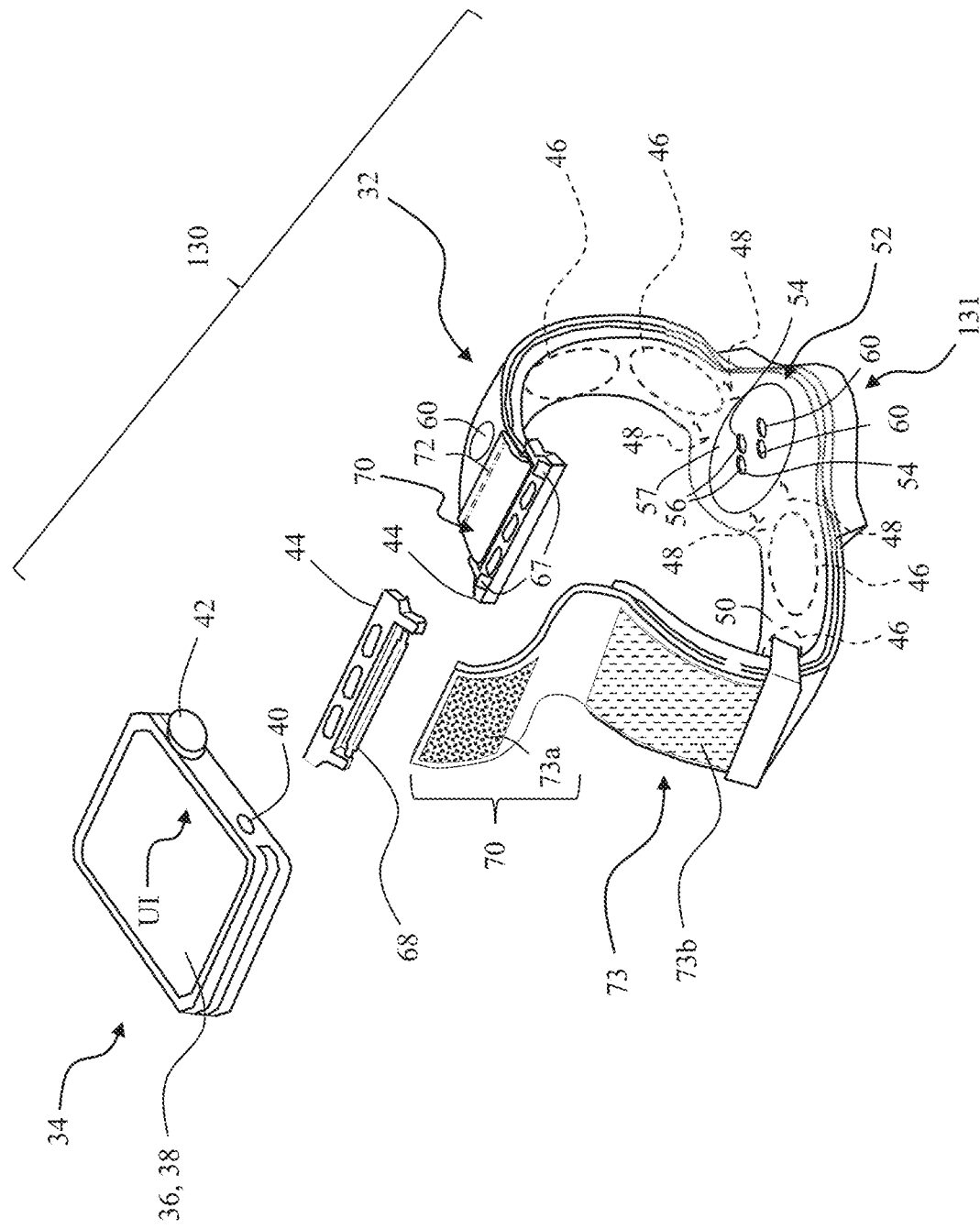
FIG. 12 is a partially exploded view of the wearable device of FIG. 10 illustrating connectors for connecting a wrist band to a display unit.

In some versions, the waveforms may be created by the user, therapist, or by another. This can be done by recording the user, therapist, or other person with a microphone 64 on the wearable device 30. The controller 66 records an audio track of the user from voice signals output by the user, therapist, or other person, and received by the microphone 64, and then transforms the audio track into the output for the one or more haptic generators 46. FIG. 9 illustrates the user creating a waveform via the microphone 64. The waveform may also be a song selected by the user or therapist with the associated audio file (e.g., .mp3, .wav, etc.) being saved in the memory MEM of the control system 62 for playback through the one or more haptic generators 46 during the training mode. One suitable software program for creating and playing such audio files is Audacity® 2.3.2 available through www.AudacityTeam.org. Suitable haptic generators 46 and controls therefor that can be used with this software program to generate desired waveforms include those available from Boreas Technologies Inc. described above. In some versions, the same waveform may be employed for multiple users, or a unique waveform may be employed for each user. In some versions, the user may be able to select one from a plurality of possible waveforms via the user interface UI.

Once the therapy mode has been enabled, e.g., the training mode is complete, then the controller 66 is configured to provide therapy to the user in the therapy mode by activating the one or more haptic generators 46 in the same predetermined pattern used in the training mode in response to input from a therapy trigger. The thermal elements 48 may also be activated to bring the user's skin temperature to the same predetermined temperature that was used in the training mode. The therapy mode is intended to bring the user back into a relaxed state should the user experience a physiological state caused by stress and/or anxiety. The therapy mode employs the same predetermined pattern of haptic output and/or skin temperature so that one or more physiological parameters of the user change (lower or rise) to those levels that were present during training, e.g., when relaxed. In other words, since the training mode occurs during periods of relaxation, the intent of the therapy mode is to elicit a response from the user that brings them closer to the same relaxation they experienced during the training sessions.

A therapy session may be initiated/stopped by the user or by a therapist via the user interface (e.g., via a start/stop therapy mode icon on the touchscreen or button). In this case, the therapy trigger comprises a user input device (e.g., touchscreen, sensor, button, etc.) that transmits user input to the controller 66 via the user interface UI. In some cases, the training mode start/stop icon or button automatically changes to the therapy mode start/stop icon or button once training is complete—and the therapy mode start/stop icon or button then becomes the therapy trigger. One or more therapy triggers may activate a therapy session. Referring briefly back to FIG. 2, one of the therapy triggers is shown by an icon IC on the touchscreen 38 of the display unit 34. When the icon IC is touched by the user, an input signal is sent to the controller 66 indicating that a therapy session is to be activated. Thereafter, therapy begins as set forth, for example, in one or more of the several embodiments described herein. For instance, the repeating waveform may be output by the one or more haptic generators 46 for a predetermined duration, or until the user stops the therapy session via the user interface UI. During therapy, the user's skin temperature may also be raised to a predetermined therapy temperature.

A therapy session may additionally, or alternatively, be initiated/stopped automatically in response to one or more physiological parameters of the user reaching, falling below, or exceeding certain thresholds. In this case, the therapy trigger comprises one or more sensors selected from the optical sensors 54, the pressure sensors 58, temperature sensors 59, the ECG sensors 60, EEG sensors, blood oxygen sensors, or other suitable sensors. The one or more sensors that are monitored to trigger the therapy session may measure heart rate, blood pressure, skin temperature, ECG signals, EEG signals, blood oxygen, combinations thereof, and the like. A therapy session may be triggered automatically in response to any one or more of the user's heart rate, skin temperature, blood pressure, EEG signals, and ECG signals reaching or exceeding a threshold, the user's blood oxygen levels reaching or falling below a threshold, combinations thereof, or the like. In some versions, a therapy session may be triggered in response to one or more physiological parameters changing quickly (e.g., a 10% increase/decrease in 1 second, a 20% increase/decrease in 5 seconds, etc.). Rapid rates of change for some physiological parameters may be an indicator of acute stress or anxiety that can be treated by the therapy methods described herein. In some cases, the thresholds may be discrete values or ranges of values. For example, the therapy session may be initiated automatically upon the controller 66 detecting the user's heart rate reaching or exceeding a threshold (e.g., reaching or exceeding 100 beats per minute, reaching or exceeding 90 beats per minute, reaching or exceeding 75 beats per minute, reaching or exceeding 70 beats per minute, etc.) and/or the therapy session may be automatically stopped upon the controller 66 detecting one or more physiological parameters of the user reaching, falling below, or exceeding certain thresholds (may be the same or different thresholds than those that initiate the therapy session). For example, the therapy session may be stopped automatically upon the controller 66 detecting the user's heart rate reaching or falling below a threshold (e.g., reaching or falling below 100 beats per minute, 90 beats per minute, 75 beats per minute, 70 beats per minute, etc.).

The thresholds may be user-specific and/or set by the therapist based on typical values of the user. The wearable device 30 may also learn the thresholds in a learning mode that occurs before the training mode. In the learning mode, the wearable device 30 may monitor the user for a predetermined duration, e.g., one day, one week, etc. and may then define the thresholds based on averages (e.g., average heart rate, average blood pressure, etc.), based on low values, based on high values, based on predetermined offsets from the low values or the high values, based on look-up tables for similar users or groups of users, and the like. The therapy sessions may last a few seconds, one minute, two minutes, five minutes, or longer, depending on the user's or therapist's input, how long it takes for the user's physiological parameters to reach, fall below, or exceed the thresholds, etc. Automatic triggering of a therapy session based on one or more thresholds may also take into account movement of the user. Such movement can be detected by an accelerometer AM built into the wearable support 32 and/or the display unit 34. The accelerometer can detect movements of the user typically associated with walking, running, biking, or other exercising, and can prevent the wearable device 30 from otherwise triggering a therapy session during such events. For instance, if the wearable device 30 is set to trigger a therapy session any time the user's heart rate exceeds 90 beats per minute, the controller 66 can be programmed to monitor movements of the user and if the user's heart rate is found to exceed 90 beats per minute, but the controller 66 determines that the user is moving in a manner consistent with exercise (high acceleration values over long duration, etc.), then the controller 66 may inhibit initiation of a therapy session until the user's heart rate falls back below the threshold and the accelerometer indicates that the user is relatively sedentary.

In some versions, the wearable device 30 is programmed to provide haptic therapy and/or thermal therapy without any required training of the user, i.e., without a training mode. For example, the haptic generators 46 may simply be triggered to operate in a predetermined pattern in response to the therapy trigger being activated, i.e., via manual input or through measurements by the one or more sensors. Automatic triggering of therapy may be useful to cause the user to pause a moment when certain physiological parameters are rising or falling so that they become mindful of the situation. For example, therapy may be triggered automatically in response to any one or more of the user's heart rate, skin temperature, blood pressure, EEG signals, and ECG signals reaching or exceeding a threshold, the user's blood oxygen level reaching or falling below a threshold, combinations thereof, or the like. In some cases, such therapy may simply be automated responses to changing physiological parameters that bring the user back into a present state of mind (e.g., mindfulness) and thereafter, the user may be able to employ manual relaxation techniques (e.g., breathing techniques) to calm their body and control the levels of the physiological parameters being measured. In some cases, the haptic generators 46 may be operated with waveforms having initially high amplitudes to achieve large vibrations to get the user's attention quickly.

In some versions, the wearable device 30 is programmed to automatically enable operation of the haptic generators 46 when the wearable support 32 is attached to the display unit 34, e.g., by virtue of the identification device ID being read by the controller 66 (e.g., via a RFID reader on the display unit 34 or via the controller 66 on the display unit 34 reading the unique identifier from non-volatile memory on the wearable support 32). In some cases, the controller 66 may be programmed to automatically display/enable a user input device that can be actuated by the user to initiate a therapy session. Referring back to FIG. 2, the controller 66 may be programmed to display the icon IC automatically in response to the wearable support 32 being connected to the display unit 34 by virtue of the electronic connections being made through one or more of the connectors 44 and the display unit 34 determining the identification of the wearable support 32, i.e., that the wearable support 32 is one capable of providing such therapy.

Figure 13:
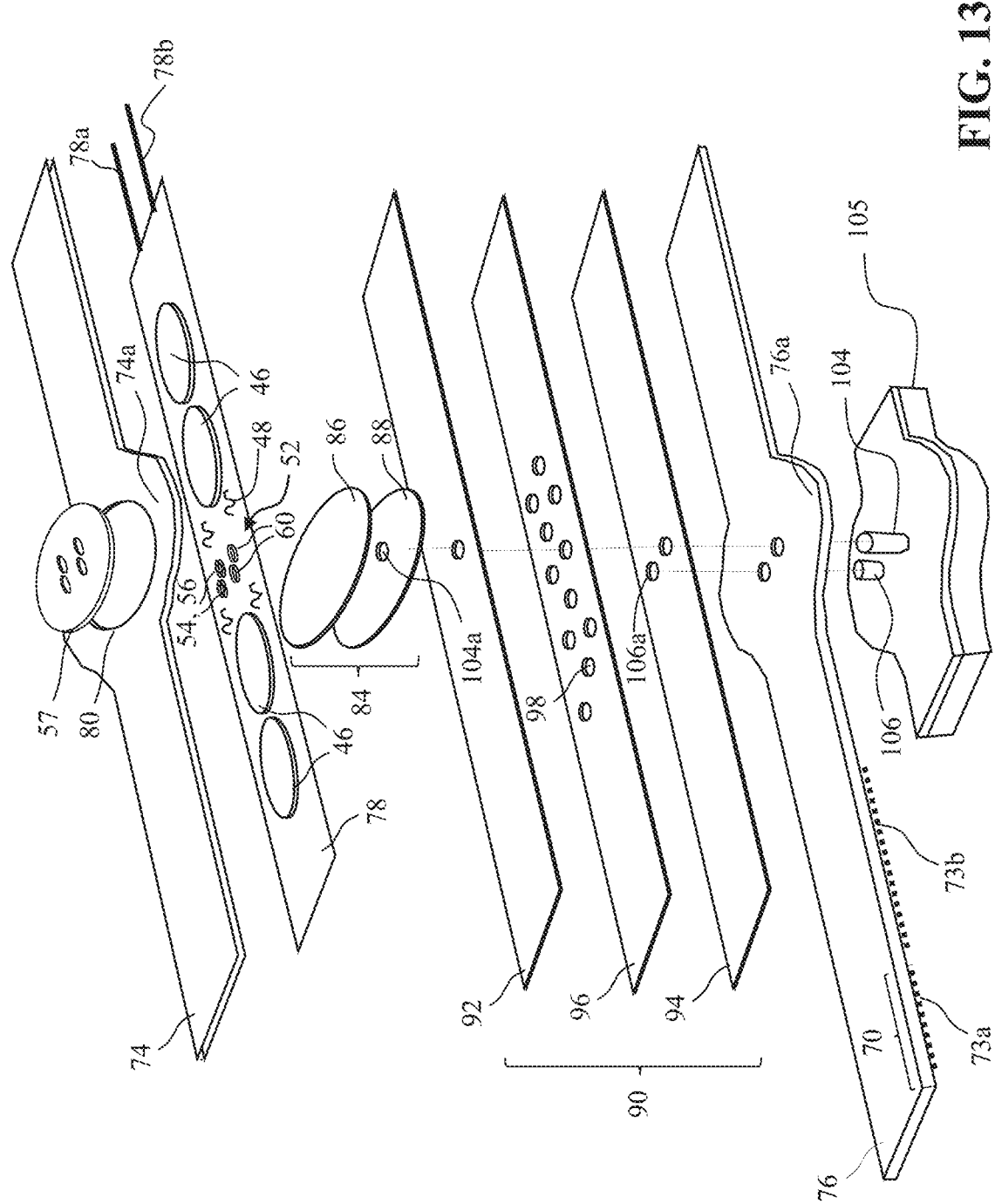
FIG. 13 is an exploded perspective view of the wrist band of FIG. 10.

Referring to FIGS. 10-15 another wearable device 130 is shown. This version is similar to the wearable device 30 previously described, but the one or more haptic output devices additionally, or alternatively, comprises a pressure-applying system 131 including a pressure-applying body. In the version shown in FIGS. 10-15, the pressure-applying body comprises a first inflatable bladder 84. As best shown in FIG. 13, the first inflatable bladder 84 is formed by first and second bladder layers 86, 88 that are sealed together to form an inflatable region using ultrasonic welding, RF welding, adhesive, combinations thereof, and/or any other suitable method. The first and second bladder layers 86, 88 may be sealed together about their outer peripheries to form the inflatable region. The first and second bladder layers 86, 88 are flexible and may be formed of inelastic, elastic, and/or semi-elastic materials. Such materials may include, for example, Kevlar, Viton, Neoprene, silicone, nitrile, nylon, polyurethanes, polyester, polyethylene, polyvinylchloride, or any other suitable materials. The first inflatable bladder 84 may have a predefined shape and size when inflated, or may stretch when inflated, or portions of the first inflatable bladder may stretch, while others are substantially inelastic. In some versions, the second bladder layer 88 is substantially inelastic, while the first inflatable bladder layer 86 is substantially elastic or semi-elastic. In some versions, both the bladder layers 86, 88 are substantially inelastic so that the first inflatable bladder 84 forms a predefined shape and size when fully inflated (e.g., to a predefined inflation pressure). In some versions, the first inflatable bladder 84, when fully inflated, is inflated to an interior volume of less than thirty cubic centimeters. In some versions, the first inflatable bladder 84, when fully inflated, is inflated to an interior volume of less than twenty cubic centimeters. In some versions, the first inflatable bladder 84, when fully inflated, is inflated to an interior volume of less than ten cubic centimeters. In some versions, when fully inflated, the first inflatable bladder 84 has an interior volume of less than three cubic centimeters.

The first inflatable bladder 84 may be disposed between the first flexible layer 74 and the second flexible layer 76. The first inflatable bladder 84 may be located beneath the flex circuit 78 and aligned with the sensor housing 57 such that the sensor housing 57 (and associated sensors 54/light sources 56) moves with inflation/deflation of the first inflatable bladder 84. The first inflatable bladder 84 may be attached to the first flexible layer 74, the second flexible layer 76, and/or the flex circuit 78 via adhesive, stitching, ultrasonic welding, radiofrequency (RF) welding, tape, or the like, or may be loosely placed between the flexible layers 74, 76. Each of the flexible layers 74, 76 has an outwardly extending section 74a, 76a, as shown in FIG. 13, to accommodate the first inflatable bladder 84. The flexible layers 74, 76 may be attached about their outer peripheries, including the outer peripheries of the outwardly extending sections 74a, 76a, using one or more of the attachment methods described, or using any suitable attachment method.

A second pressure-applying body may also be used. In the version shown in FIGS. 10-15, the second pressure-applying body includes a second inflatable bladder 90. The second inflatable bladder 90 is formed by third and fourth bladder layers 92, 94. The second inflatable bladder 90 may be disposed between the first and second flexible layers 74, 76, and between the first inflatable bladder 84 and the second flexible layer 76. An intermediate bladder layer 96 having one or more through holes 98 may be placed between the third and fourth bladder layers 92, 94. The third and fourth bladder layers 92, 94 are sealed together about their outer peripheries to form an inflatable region using ultrasonic welding, RF welding, adhesive, combinations thereof, and/or any other suitable method. The intermediate bladder layer 96 may be sealed to the third bladder layer 92 and/or the fourth bladder layer 94, or may be loosely placed between the third and fourth bladder layers 92, 94. Given the length of the bladder layers 92, 94, 96, interior welds connecting the bladder layers 92, 94, 96, spaced inboard from their outer peripheries, may be provided to prevent ballooning of the second inflatable bladder 90. The third and fourth bladder layers 92, 94, and the intermediate bladder layer 96 are flexible and may be formed of inelastic, elastic, and/or semi-elastic materials. Such materials may include, for example, Kevlar, Viton, Neoprene, silicone, nitrile, nylon, polyurethanes, polyester, polyethylene, polyvinylchloride, or any other suitable materials. The second inflatable bladder 90 may have a predefined shape and size when inflated, or may stretch when inflated, or portions of the second inflatable bladder 90 may stretch, while others are substantially inelastic. In some versions, the fourth bladder layer 94 is substantially inelastic, while the third inflatable bladder layer 92 is substantially elastic or semi-elastic. In some versions, both the third and fourth bladder layers 92, 94 are substantially inelastic so that the second inflatable bladder 90 forms a predefined shape and size when fully inflated (e.g., to a predefined inflation pressure).

In some versions, the second inflatable bladder 90 is connected at only one end to the first flexible layer 74 and/or the second flexible layer 76 such that inflation of the second inflatable bladder 90 allows free elongation of the second inflatable bladder 90 relative to the first and second flexible layers 74, 76. The second inflatable bladder 90 may substantially surround, but not fully surround, the user's wrist W (as shown), but in some versions the second inflatable bladder 90 may fully surround the user's wrist W. In some versions, the second inflatable bladder 90 has a length (in elongated direction of wrist band) sized to surround at least 50%, at least 60%, at least 70%, at least 80%, or at least 90% of the user's wrist (based on distance around the wrist). The first inflatable bladder 84 may have a length sized to be less than 5 centimeters, less than 4 centimeters, less than 3 centimeters, less than 2 centimeters, or the like. In some versions, the first inflatable bladder 84, when fully inflated, is inflated to an interior volume of less than sixty cubic centimeters. In some versions, the first inflatable bladder 84, when fully inflated, is inflated to an interior volume of less than thirty cubic centimeters. In some versions, the second inflatable bladder 90, when fully inflated, is inflated to an interior volume of less than twenty cubic centimeters. In some versions, when fully inflated, the second inflatable bladder 90 has an interior volume of less than ten cubic centimeters. In some versions, when fully inflated, the second inflatable bladder 90 has an interior volume of less than three cubic centimeters.

In some versions, the first flexible layer 74 is substantially elastic or semi-elastic to allow stretching during inflation of the first inflatable bladder 84 and/or the second inflatable bladder 90, while the second flexible layer 76 is substantially inelastic or at least less elastic than the first flexible layer 74, to inhibit stretching during inflation of the first inflatable bladder 84 and/or the second inflatable bladder 90. As a result, inflation of the first inflatable bladder 84 and/or the second inflatable bladder 90 would act to increase pressure against the user's wrist. For example, the first flexible layer 74 may be formed of silicone, Neoprene, or rubber, and the second flexible layer 76 may be formed of leather, metal, inelastic or semi-elastic plastic material, or other suitable, substantially inelastic or semi-elastic materials. Substantially inelastic or semi-elastic materials used for the second flexible layer 76, for example, may have an Elongation at Break (ratio of changed length vs. initial length after breakage) of 20% or less, while elastic materials used for the first flexible layer 74 may have an Elongation at Break of 30% or more. ASTM D638 and ISO 527 test methods may be used to determine the Elongation at Break of a material.

In the version shown, the first inflatable bladder 84 is situated above the second inflatable bladder 90 and is sized to extend along only a portion of the second inflatable bladder 90. The first inflatable bladder 84 is sized so that pressure on the wrist of the user is localized to one side of the user's wrist, while the second inflatable bladder 90 is sized to substantially surround the user's wrist, as compared to the first inflatable bladder 84. In some versions, the first inflatable bladder 84 is arranged to be in proximity to an acupressure point of the user when the wearable support 32 is worn by the user. In some versions, the first inflatable bladder 84 is arranged to be in proximity to acupressure point Pericardium 6 (P6)(also known as Nei Guan) of the user when the wearable support 32 is worn by the user. Location of the acupressure point P6 in a typical/average user is best shown in FIG. 15D. In the embodiment shown in FIGS. 10-15, the first inflatable bladder 84 has an oblong shape, e.g., a length dimension greater than a width dimension, wherein the length dimension is directed to be in a direction of the user's arm so that the first inflatable bladder 84 is more likely to be adjacent to the acupressure point P6 when the wrist band is worn by the user. In other words, gross location of the wrist band about the user's wrist W is likely to properly locate the first inflatable bladder 84 adjacent to the acupressure point P6. In some versions, the inflatable bladder 84 may be offset from a centerline of the wrist band to reach the acupressure point P6. In some versions, such as when the wearable device is a leg band, the first inflatable bladder 84 may be located to apply pressure to acupressure point ST36 (also known as Stomach 36 or Zu San Li) to release gastrointestinal discomfort. The first inflatable bladder 84 and/or the second inflatable bladder 90 may also be configured to apply pressure to other acupressure points.

The controller 66 may be programmed to actuate (inflate) the first inflatable bladder 84 to provide therapy to the user by placing pressure on the acupressure point P6 in response to the therapy trigger. In some versions, like that shown in FIGS. 10-15, the first inflatable bladder 84 is separately inflatable from the second inflatable bladder 90. Accordingly, during therapy, the first inflatable bladder 84 may be inflated, while the second inflatable bladder 90 remains uninflated. In some versions, during therapy, both the first inflatable bladder 84 and the second inflatable bladder 90 are inflated to predetermined pressures (same pressure or different pressures). In some versions, the controller 66 is operable to actuate the first inflatable bladder 84 and/or the second inflatable bladder 90 in response to activation of the therapy trigger during a therapy session in which the first inflatable bladder 84 and/or the second inflatable bladder 90 are inflated/deflated in a repeated pattern and/or to predetermined therapy pressures. In some versions, the wearable device 130 provides therapy to the user without requiring any training mode. This may be useful, for example, to apply pressure to the acupressure point P6 to treat nausea (e.g., experienced during pregnancy, sea sickness, etc.) or to treat anxiety. For example, if the user is experiencing symptoms of nausea, or expects nausea to occur at known times during the day (e.g., morning sickness), or if the user is planning to take a trip and experiences motion sickness (car, boat, plane, etc.), the user can manually trigger therapy to inflate the first inflatable bladder 84 (and possibly the second inflatable bladder 90) to apply pressure onto the acupressure point P6 (and/or other acupressure points) to treat or reduce the occurrence of nausea. Inflation of the first inflatable bladder 84, for example, could be triggered by the user tapping the icon IC on the touch screen 38 shown in FIG. 2. The first inflatable bladder 84 could then remain inflated, and the controller 66 could regulate its pressure to maintain a constant pressure, or to follow an inflation/deflation pattern, until the user stopped the therapy, such as by again tapping the icon IC.

Figure 14:
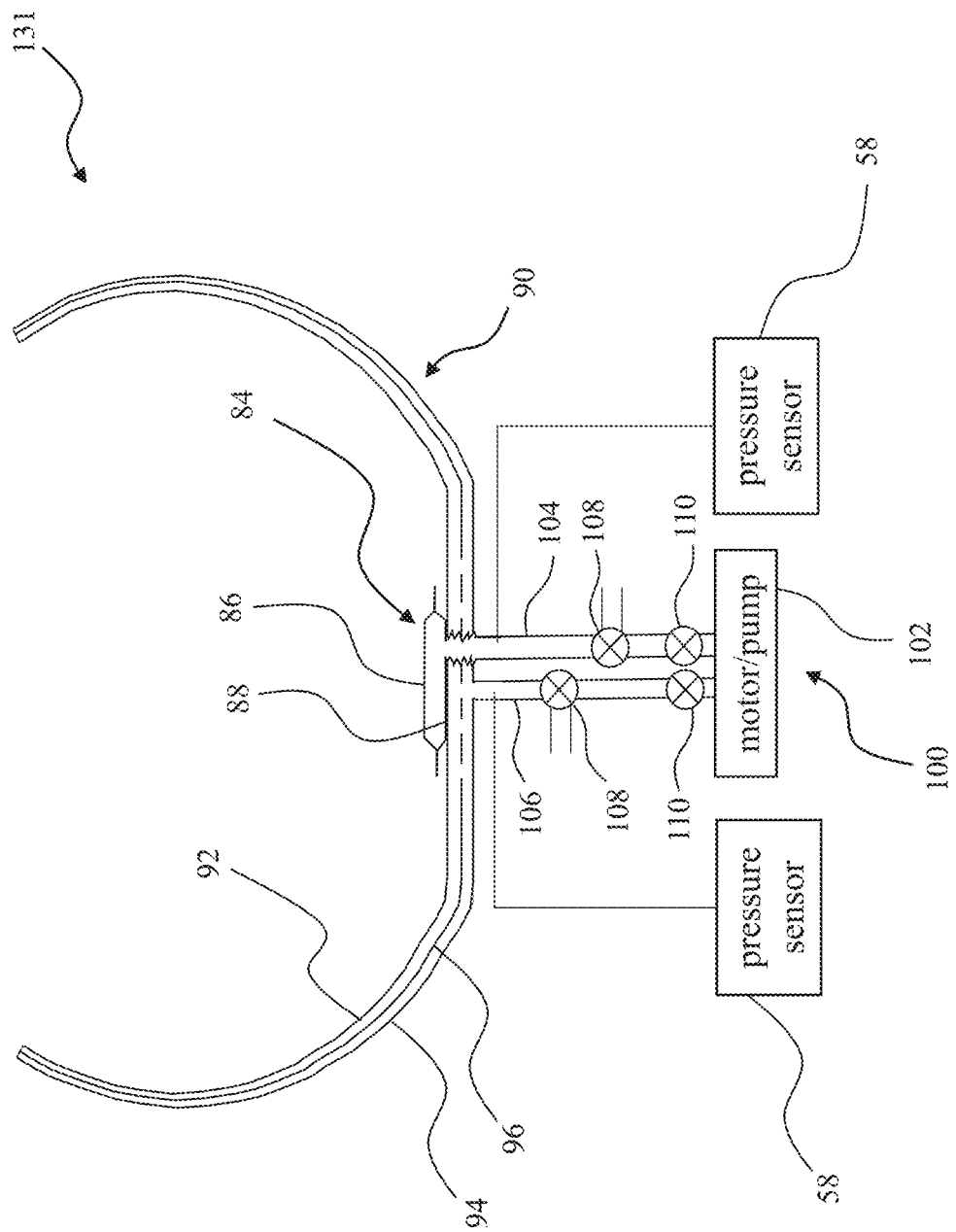
FIG. 14 is a fluid circuit for the wearable device of FIG. 10.

Referring to FIG. 14, an inflator 100 is operatively coupled to the first inflatable bladder 84 and/or to the second inflatable bladder 90 to inflate and/or deflate the inflatable bladders 84, 90. The inflator 100 may comprise a motor and air pump 102 to move air into and/or out of the inflatable bladders 84, 90. The inflator 100 is shown disposed in a inflator housing 105 that is attached and fixed to the second flexible layer 76 using an attachment method as previously described, or any suitable attachment method (see FIG. 15A). The inflator 100 may be attached to the inflator housing 105. The inflator housing 105 may be more rigid than the flexible layers 74, 76, and may be generally rigid or semi-rigid. The inflator housing 105 may be formed of plastic, metal, combinations thereof, or any other suitable material. The inflator housing 105 may comprise a base and a lid fixed to the base to enclose the inflator 100 inside the inflator housing 105.

A first conduit 104 fluidly connects the inflator 100 to the first inflatable bladder 84 and a second conduit 106 fluidly connects the inflator 100 to the second inflatable bladder 90. The conduits 104, 106 pass through the inflator housing 105 into the inflatable bladders 84, 90. The first conduit 104, as shown in FIG. 13, extends from the inflator housing 105 through an opening in the second flexible layer 76, through the third, fourth, and intermediate bladder layers 92, 94, 96 (and sealed thereto to reduce air leakage), and connects about an opening 104a to the second bladder layer 88 via an attachment method as previously described, or any suitable attachment method, to be able to direct air into and out of the inflatable region of the first inflatable bladder 84. The second conduit 106 extends from the inflator housing 105 through another opening in the second flexible layer 76 and connects to the fourth bladder layer 94 via an attachment method as previously described, or any suitable attachment method, to be able to direct air into and out of the inflatable region of the second inflatable bladder 90.

The conduits 104, 106 may be capable of stretching, may have accordion-shaped sections for elongation, or the like. The conduits 104, 106 may be formed of any suitable material for holding air pressure and/or conveying air from the motor and air pump 102 to the inflatable bladders 84, 90. Such materials may include, for example, Kevlar, Viton, Neoprene, silicone, nitrile, nylon, polyurethanes, polyester, polyethylene, polyvinylchloride, or any other suitable materials.

As shown in FIG. 14, one or more valves are connected to the first conduit 104 and to the controller 66 to control inflation/deflation of the first inflatable bladder 84. For example, one valve 108 (e.g., a three-way solenoid valve) is connected to the first conduit 104 and the controller 66 so that the controller 66 is able to operate the valve 108 in a first state which opens fluid communication between the inflator 100 and the first inflatable bladder 84 (when valve 110 is open) and a second state which opens fluid communication between the first inflatable bladder 84 and atmosphere to deflate the first inflatable bladder 84. The valve 110 may be connected to the first conduit 104 and the controller 66 so that the controller 66 can open/close fluid communication between inflator 100 and the first conduit 104, which may be useful when separately inflating the second inflatable bladder 90 (e.g., valve 110 can be closed). A similar set of valves are also connected to the second conduit 106 and the controller 66 to control inflation/deflation of the second inflatable bladder 90. Pressure sensors 58 are connected to the controller 66 and placed in fluid communication with the first inflatable bladder 84 and the second inflatable bladder 90 to measure pressures in the bladders 84, 90.

These pressure sensors 58 may be used in conjunction with operation of the first inflatable bladder 84 and/or the second inflatable bladder 90 to measure the user's blood pressure using oscillometric blood pressure measuring techniques. In some versions, only the second inflatable bladder 90 is inflated during a blood pressure measurement cycle. For example, the second inflatable bladder 90 may act as an inflatable cuff substantially surrounding the wrist W of the user with sufficient pressure to prevent blood flow in a local artery (e.g., about 20 mm Hg above systolic pressure). The pressure is then gradually released using the solenoid valve 108 (e.g., digitally controlled by the controller 66) until blood begins to flow through the artery. More specifically, as the second inflatable bladder 90 is deflated below the user's systolic pressure, the reducing pressure exerted on the artery allows blood to flow through it and sets up a vibration in the arterial wall that can be detected by the controller 66 using the pressure sensor 58 in communication with the second inflatable bladder 90. The pressure measured by the pressure sensor 58 at this point determines the systolic pressure (pressure readings from one or multiple pressure sensors can be averaged, or only a single pressure reading from one pressure sensor may be used). Heart rate (pulse rate) is also sensed at this time. A measurement taken when the blood flow is no longer restricted determines the diastolic pressure. More specifically, when the pressure in the second inflatable bladder 90 falls below the user's diastolic pressure, blood flows smoothly through the artery in the usual pulses, without any vibration in the arterial wall. This complete measurement cycle is controlled automatically by the controller 66. In some versions, the signal from the pressure sensor 58 may be conditioned with an instrumentation amplifier before data conversion by an analog-to-digital converter (ADC). The systolic pressure, diastolic pressure, and heart rate are then calculated in the digital domain using an algorithm appropriate for the type of sensor utilized. The resulting systolic, diastolic, and heart rate measurements may be displayed on the display 36, time-stamped, and stored in the memory MEM (e.g., non-volatile memory).

Figure 15A:
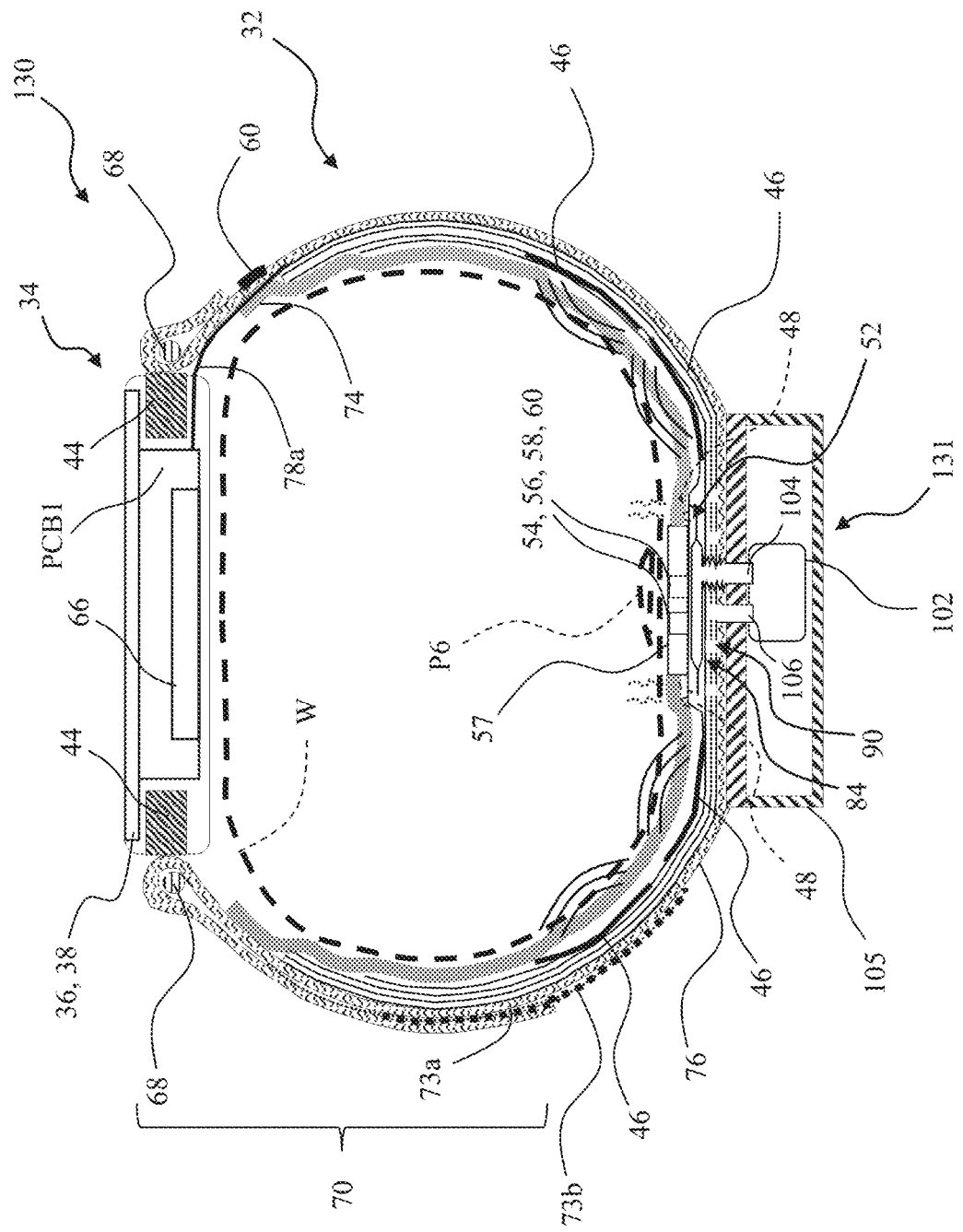
FIG. 15A is a cross-sectional view of the wearable device of FIG. 10 in an uninflated state.
Figure 15B:
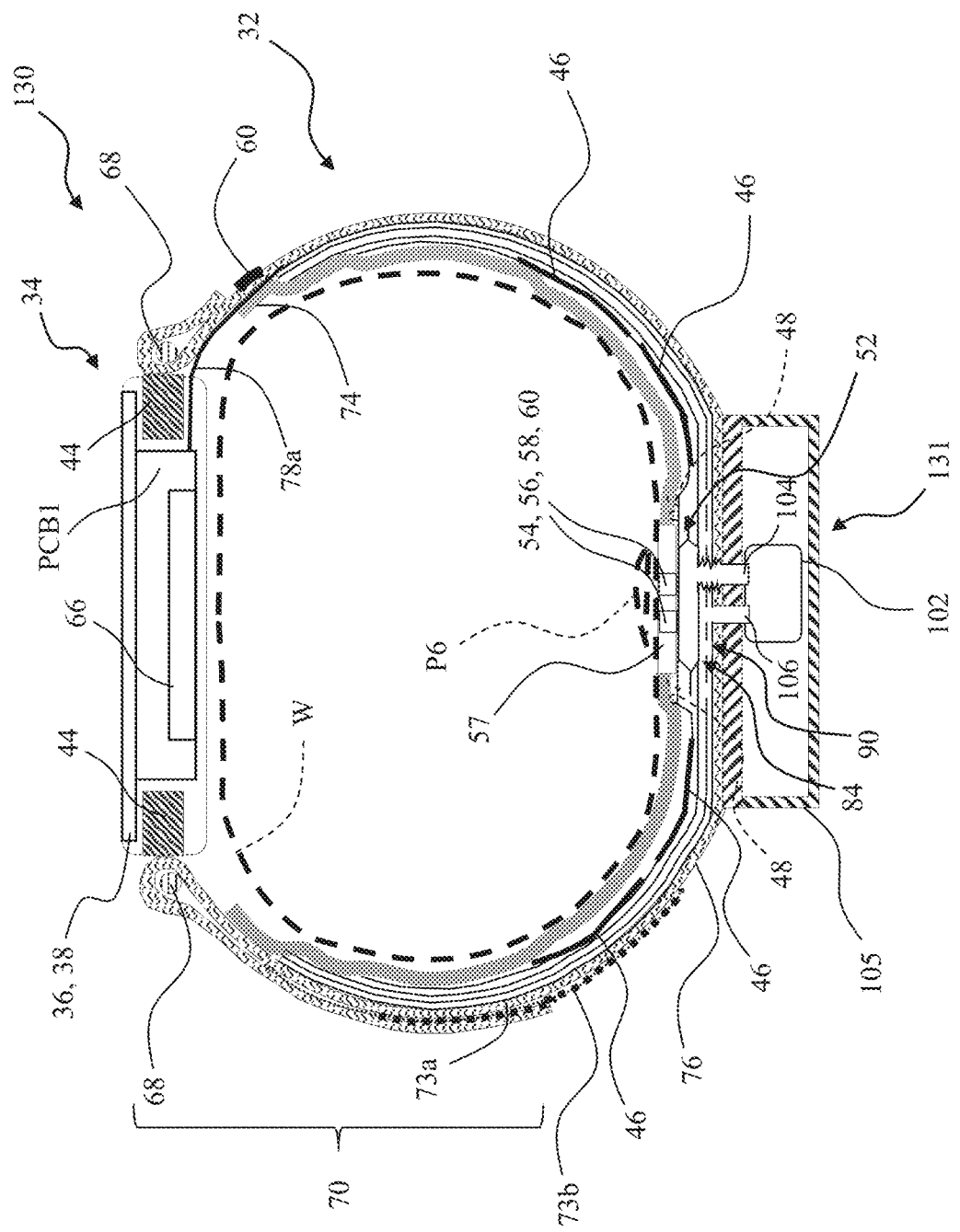
FIG. 15B is a cross-sectional view of the wearable device of FIG. 10 wherein a first inflatable bladder is in a fully inflated state and a second inflatable bladder is in a partially inflated state.
Figure 15C:
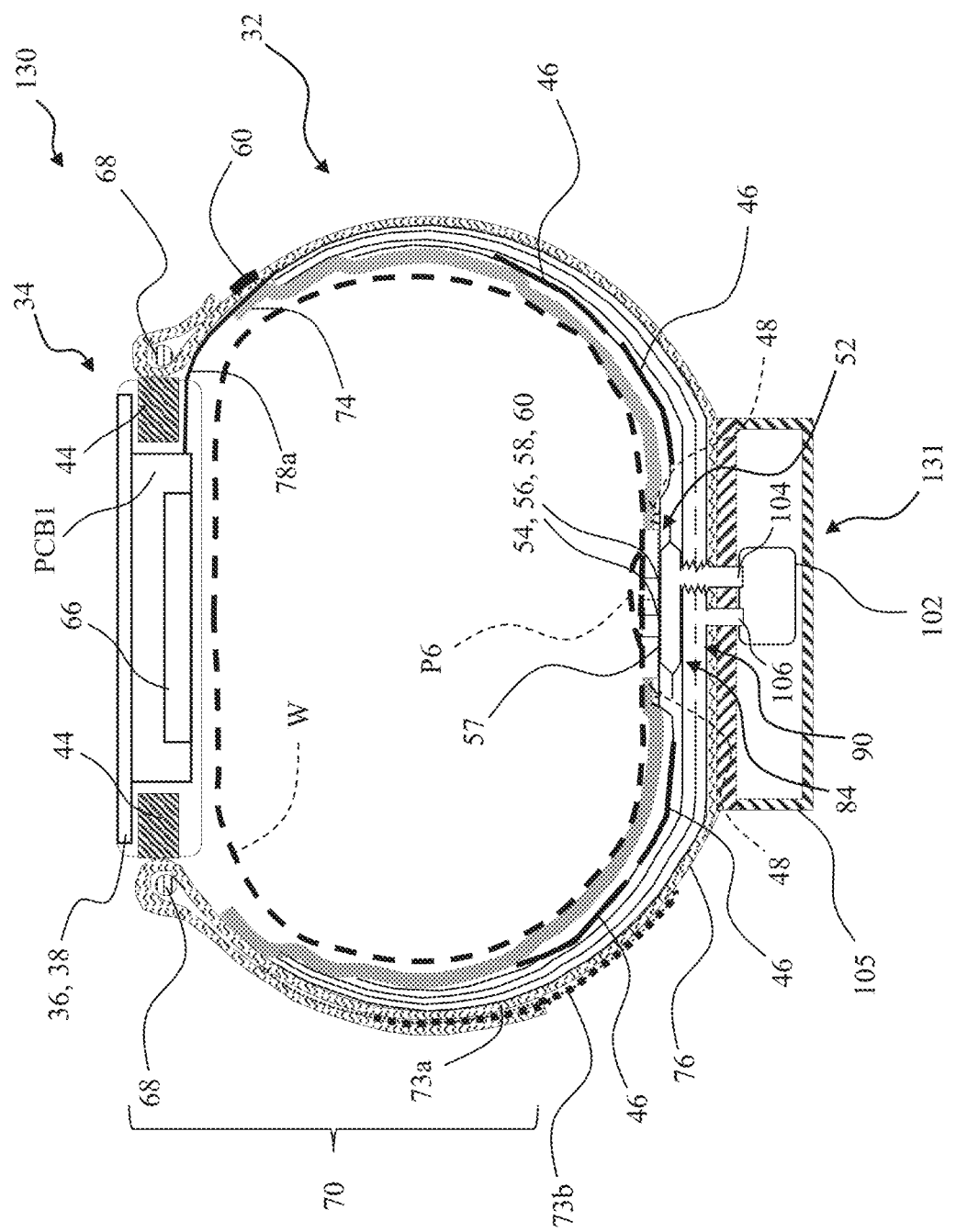
FIG. 15C is a cross-sectional view of the wearable device of FIG. 10 wherein the first inflatable bladder is in the fully inflated state and the second inflatable bladder in a fully inflated state.
Figure 15D:
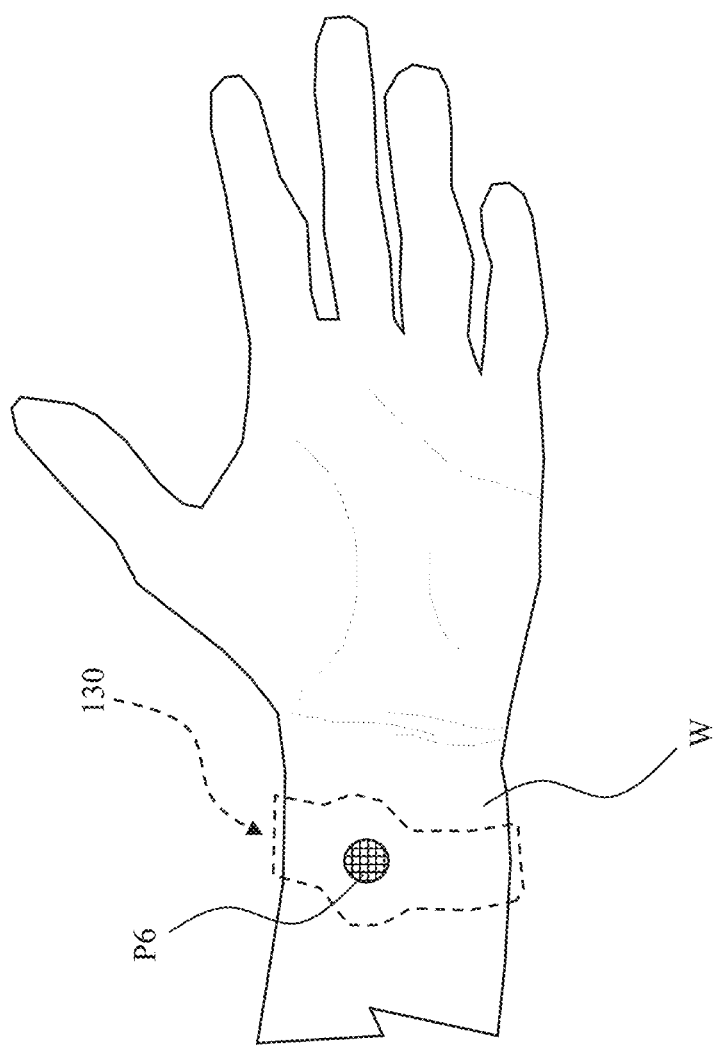
FIG. 15D is an illustration of a user's wrist and the acupressure point P6.

Inflation of the inflatable bladders 84, 90 is shown in the progression of FIGS. 15A-15C. In FIG. 15A, the inflatable bladders 84, 90 are shown uninflated and haptic feedback (haptic output) is being provided to the user through the haptic generators 46 to alert the user that one or more of the inflatable bladders 84, 90 is about to be inflated. Since inflation of the inflatable bladders 84, 90 will apply pressure on the user's wrist W, it may be helpful to first alert the user of such an event. This may be useful, for example, when the user's blood pressure is being measured periodically throughout the day, such as according to a preset schedule stored in the memory MEM and executed by the controller 66 to monitor and record several blood pressure readings of the user pursuant to the schedule. Such readings may be stored for later retrieval by the user, physician, etc. and/or may be automatically transmitted via a communication link (e.g., WiFi, Bluetooth, cellular) from the wearable device 30 to a network (e.g., the Internet, cloud, etc.). Accordingly, the controller 66 may be programmed to activate the one or more haptic generators 46 prior to inflating either or both of the bladders 84, 90. Other indications that inflation is about to occur may additionally, or alternatively, be provided, e.g., audible, visual, etc. For instance, the display 36 may provide a visual indication (symbol, text, countdown timer, etc.) that inflation is going to occur, and/or the display unit 34 may comprise one or more speakers that audibly alert the user that inflation is about to occur. FIG. 15B shows the first inflatable bladder 84 being fully inflated and acting against the acupressure point P6 of the user. FIG. 15C shows both the first inflatable bladder 84 and the second inflatable bladder 90 being fully inflated and compressing the user's wrist W.

In some versions, the second inflatable bladder 90, the inflator 100, and the valve 108 and pressure sensor 58 associated with the second inflatable bladder 90 define a first blood pressure measurement unit operatively coupled to the wrist band to measure the blood pressure of the user. The optical sensors 54, light sources 56, pressure sensors 58, and ECG sensors 60 define a second blood pressure measurement unit operatively coupled to the wrist band to measure the blood pressure of the user. Measuring blood pressure using optical methods may be subject to drift and require calibration, e.g., via oscillometric methods. Accordingly, by providing two blood pressure measurement units on the same wearable device (one optically-based and one oscillometrically-based), calibration can be made easy. In these versions, the controller 66 is operatively coupled to the first blood pressure measurement unit and the second blood pressure measurement unit. The controller 66 operates in a normal mode to take one or more blood pressure measurements of the user with the second blood pressure measurement unit, e.g., the optically-based blood pressure measurement unit—which may be less intrusive to the user since it does not require inflating any inflatable bladders. The controller 66 operates in a calibration mode to take one or more blood pressure measurements with the first blood pressure measurement unit to calibrate the second blood pressure measurement unit. Such calibration may include providing an adjustment factor to the readings from the second blood pressure measurement unit. For example, blood pressure measurements may be made by the controller 66 at substantially the same time using both the first and second blood pressure measurement units with the measurements taken with the second blood pressure measurement unit being adjusted to be the same as the measurements taken with the first blood pressure measurement unit (e.g., by adjusting the systolic/diastolic pressures up/down as needed). This adjustment factor may then be used for all future measurements taken with the second blood pressure measurement unit until the next calibration event.

Figure 16:
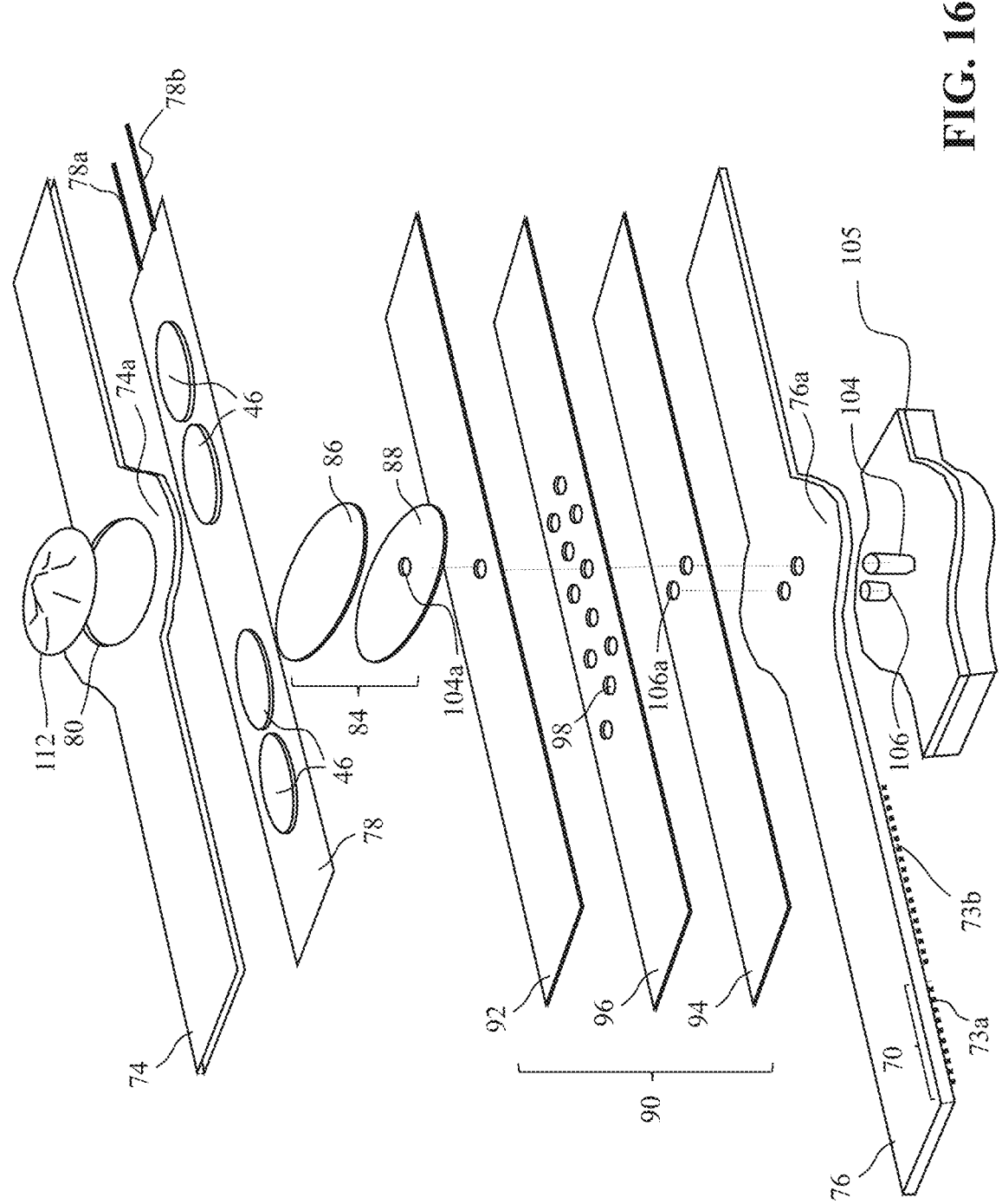
FIG. 16 is an exploded perspective view of a wrist band including a projection for placing against an acupressure point of a user.
Figure 17:
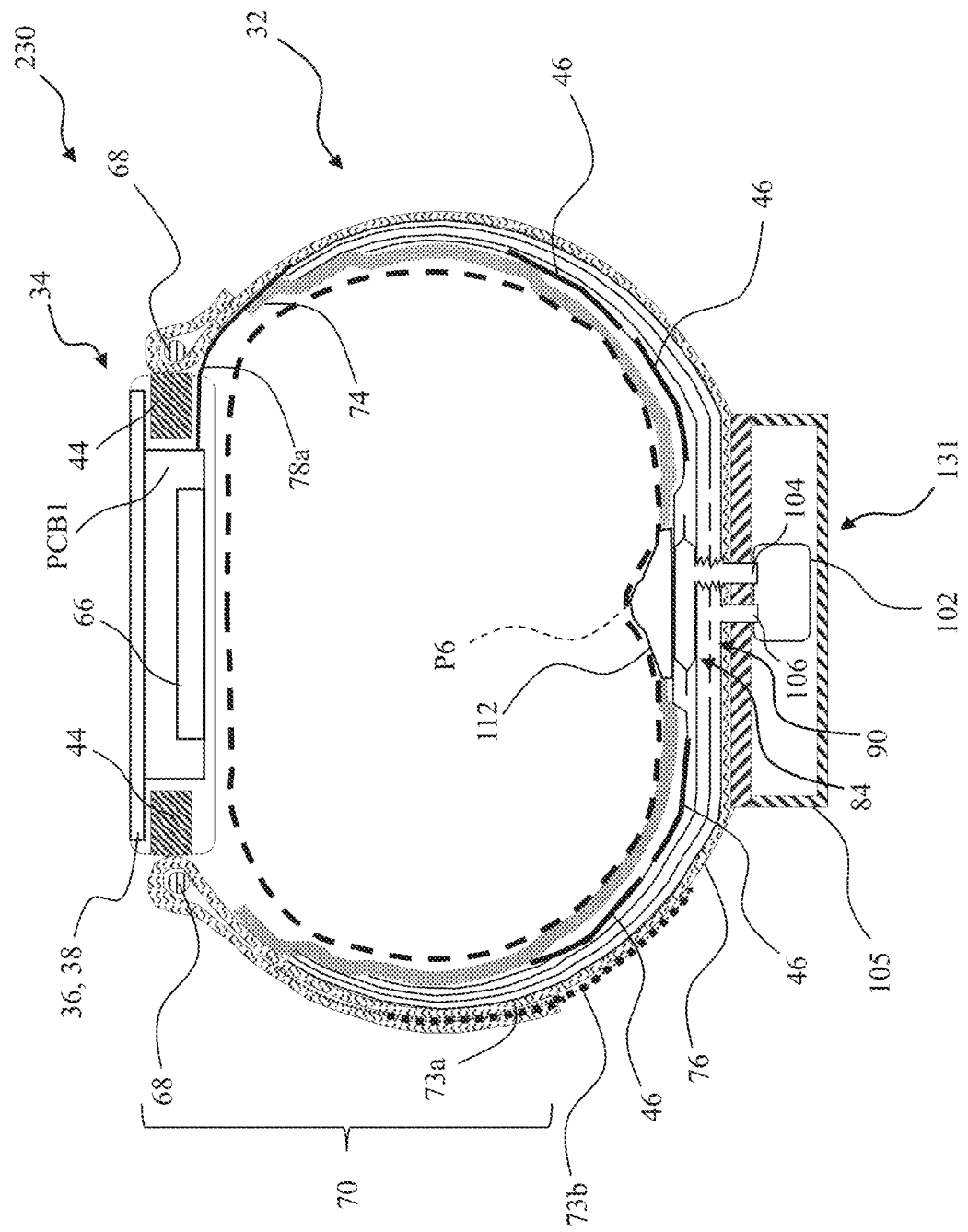
FIG. 17 is a cross-sectional view of a wearable device illustrating the wrist band of FIG. 16 with the projection being pressed into the acupressure point of the user during therapy.

FIGS. 16 and 17 illustrate another wearable device 230 that is similar to the wearable device 130 and includes the first inflatable bladder 84 and the second inflatable bladder 90, but further includes a projection 112 that is attached to the first flexible layer 74 to move with inflation/deflation of the first inflatable bladder 84 to localize pressure on the acupressure point P6 of the user. In this version, the sensor housing 57 has been replaced by the projection 112, which is attached to the first flexible layer 74 in the opening 80 using an attachment method as described herein, or any suitable attachment method. In some versions, the sensors/light sources 54, 56, 58, 60 may be placed inside the projection 112 to take measurements as previously described. The projection 112 may be formed of plastic (e.g., foam or the like) and have a rounded head to apply pressure on the acupressure point P6 of the user. The head may also be referred to as a massage head. The head may be semi-spherical in shape (e.g., ball-shaped) or frustoconical in shape. Other shapes/materials for the head of the projection 112 are possible.

Figure 18:
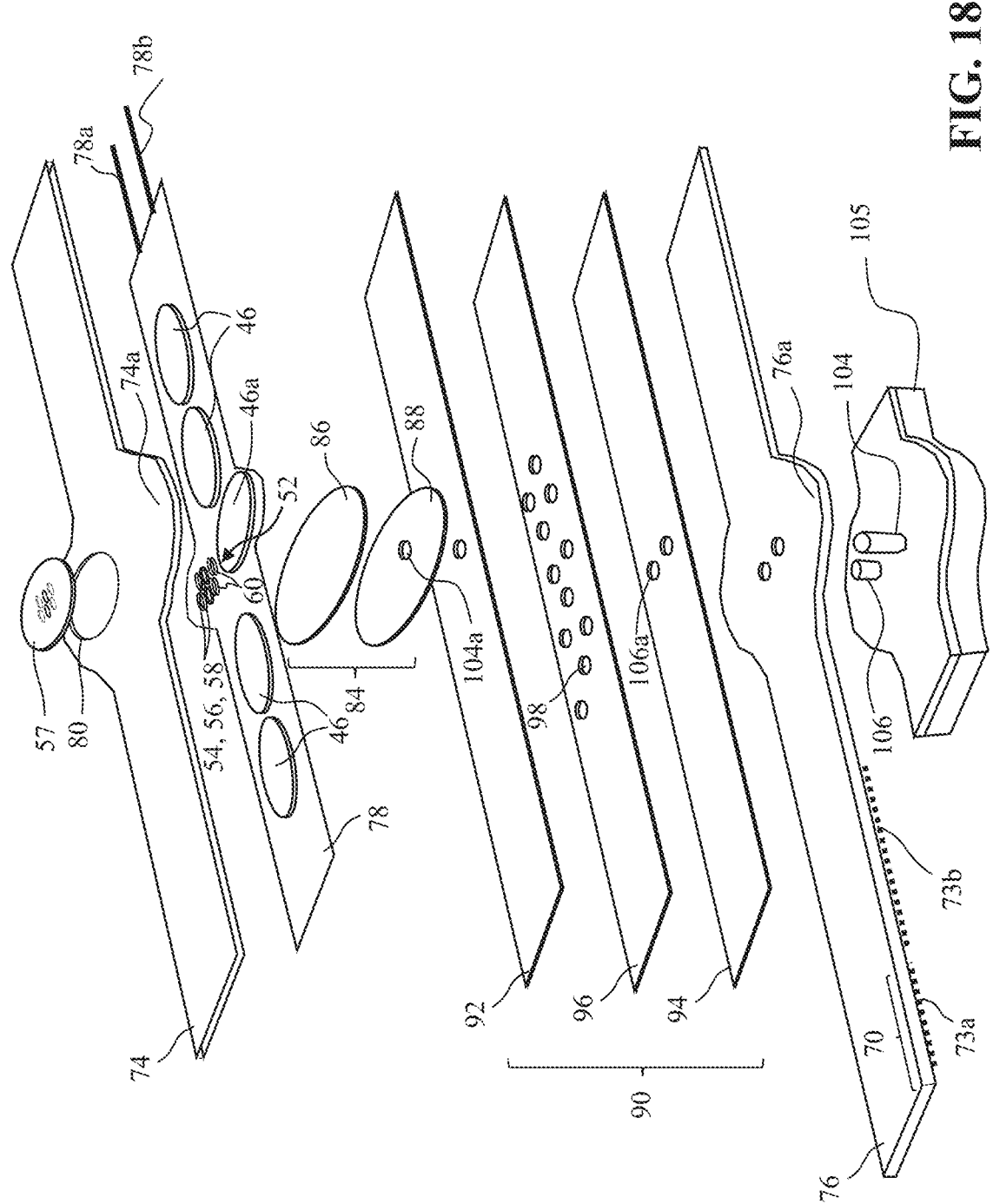
FIG. 18 is an exploded perspective view of a wrist band including a haptic generator for placing against an acupressure point of a user.
Figure 19:
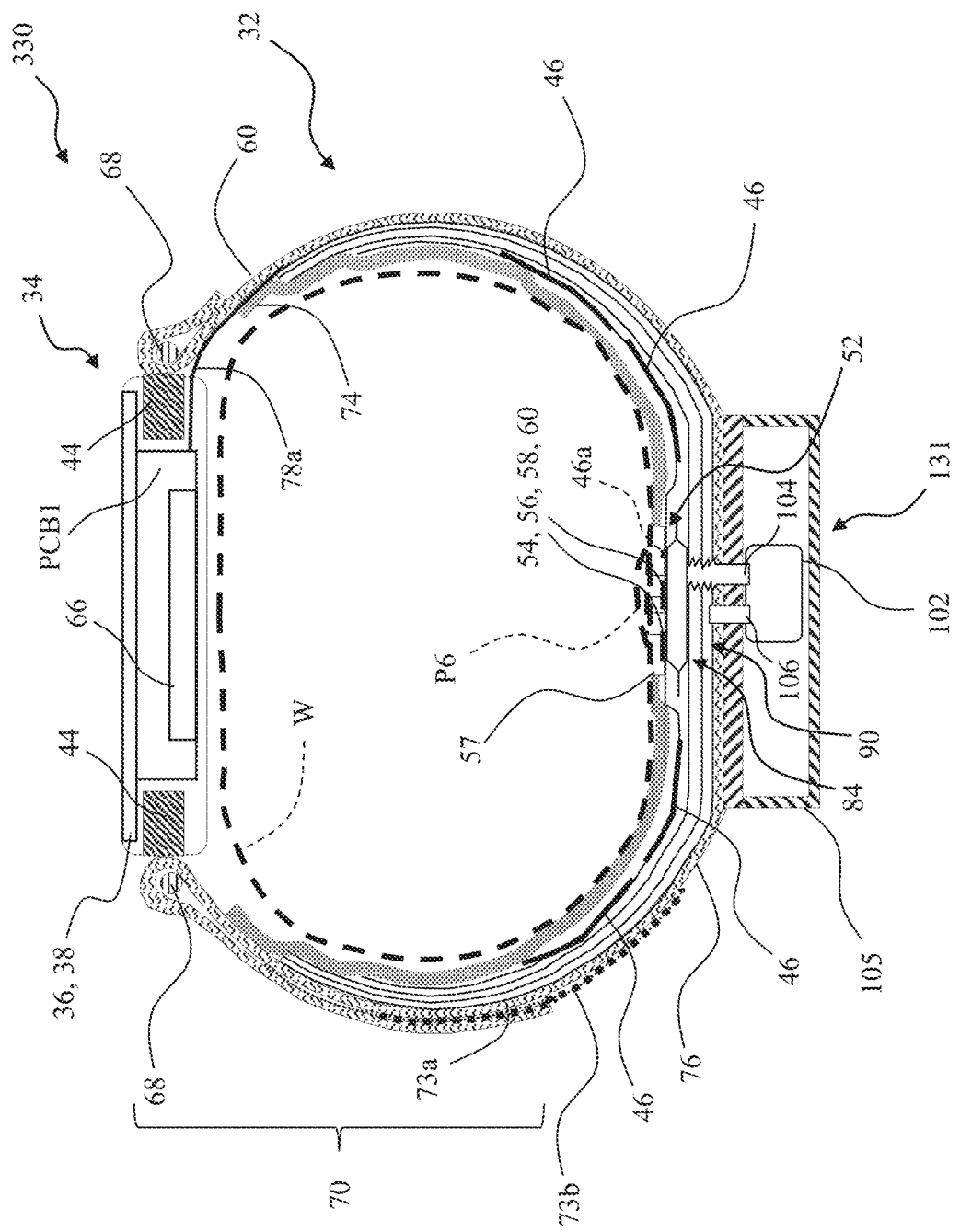
FIG. 19 is a cross-sectional view of a wearable device illustrating the wrist band of FIG. 18 with the haptic generator being placed against the acupressure point of the user during therapy.

FIGS. 18 and 19 illustrate another wearable device 330 that is similar to the wearable device 130 and includes the first inflatable bladder 84 and the second inflatable bladder 90, but further includes a haptic generator 46a that is mounted to the flex circuit 78 to move with inflation/deflation of the first inflatable bladder 84 to provide haptic therapy on the acupressure point P6 of the user (e.g., via vibrations of a predetermined magnitude, frequency, and/or duration, and/or as previously described herein). In this version, the sensor housing 57 has been located adjacent to the haptic generator 46a and the haptic generator 46a that is intended to align with the acupressure point P6. This version may be useful, for example, to provide therapy to the user in the form of both inflating the first and/or second inflatable bladders 84, 90, and activating the one or more haptic generators 46, including the haptic generator 46a in proximity to the acupressure point P6 of the user. Additional haptic generators 46 may be arranged on the wearable support 32 to be in proximity to the acupressure point P6 (or other acupressure point) of the user when the wearable support 32 is worn by the user.

Figure 20A:
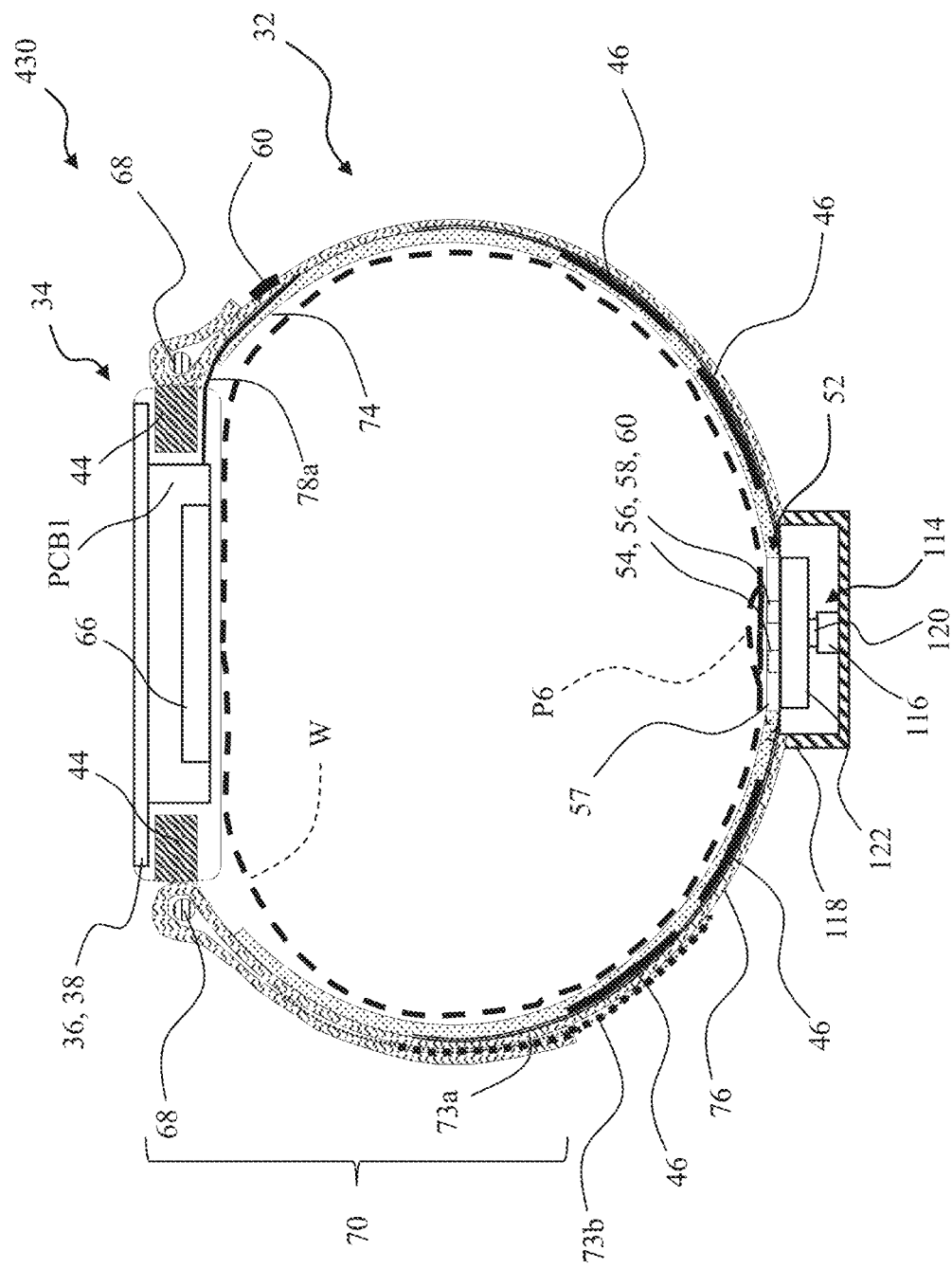
FIG. 20A is a cross-sectional view of a wearable device illustrating a sensor housing being placed against an acupressure point of the user during therapy.
Figure 20B:
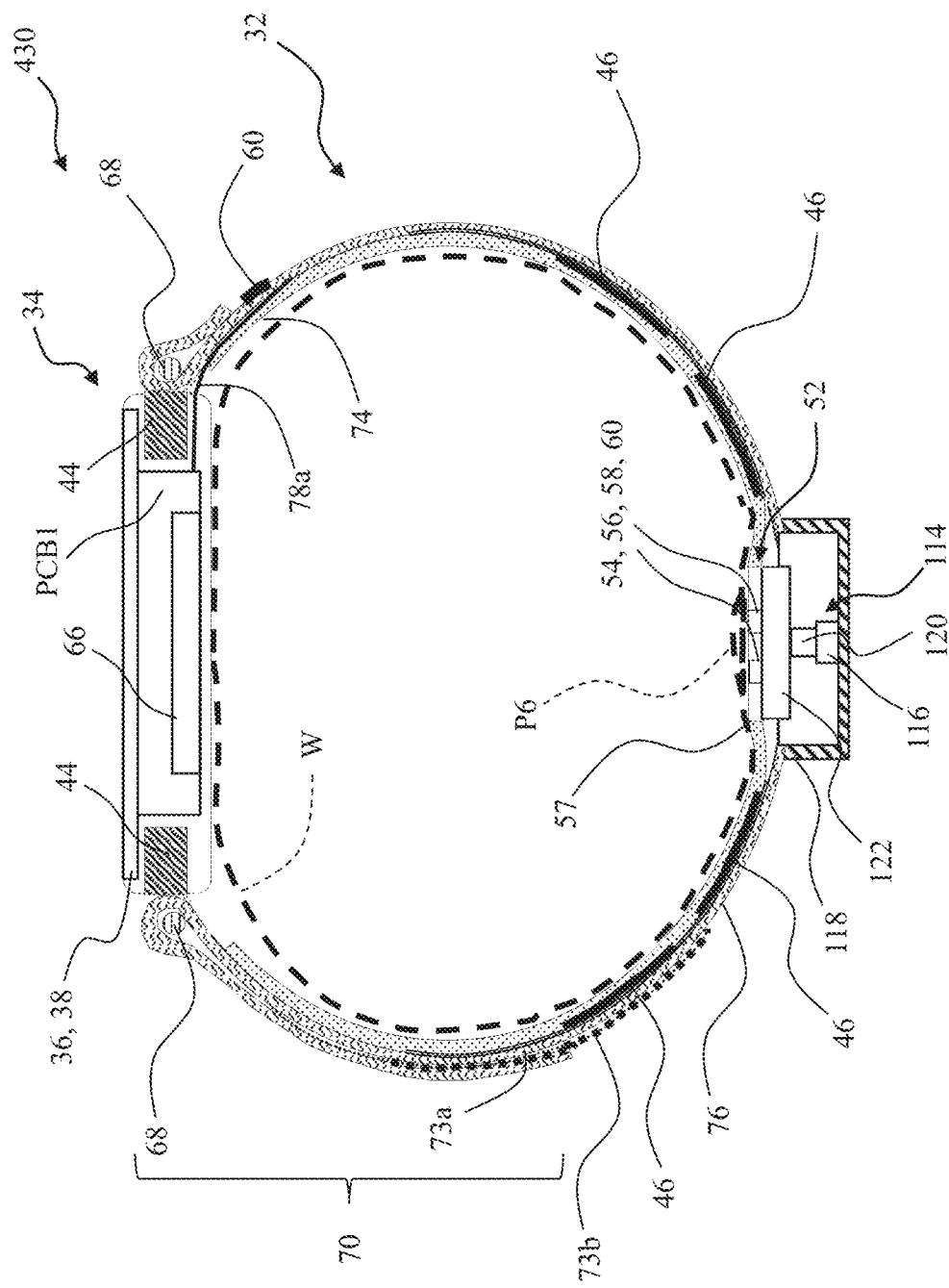
FIG. 20B is a cross-sectional view of the wearable device illustrating actuation of a linear actuator to apply pressure to the acupressure point.

FIGS. 20A and 20B illustrate another wearable device 430 that employs a linear actuator 114 to apply pressure to the acupressure point P6 of the user. The linear actuator 114 is connected to the controller 66 to be activated by the controller 66. The linear actuator 114 has a base 116 mounted to a rigid housing 118. The housing 118 is attached and fixed to the second flexible layer 76 using an attachment method as previously described, or any suitable attachment method. A linearly-movable rod 120 is extendable/retractable from the base 116. A pressure-applying body 122 is fixed to one end of the rod 120 to move with the rod 120. During actuation of the linear actuator 114, the pressure-applying body 122 is moved toward the acupressure point P6 to provide therapy to the user. The pressure-applying body 122 is shown beneath the sensor housing 57 to move the sensor housing 57 to apply such pressure, but the pressure-applying body 122 may be in direct contact with the user's wrist in some versions, or located underneath flexible material of the wearable support 32 to protrude into the flexible material (e.g., beneath a flexible layer). In some versions, the pressure-applying body 122 may have a shape similar to the projection shown in FIG. 17, or may have a semi-spherical shape, or other shape. In some versions, the rod 120 may act as the pressure-applying body and may be located beneath the sensor housing 57 to move the sensor housing 57 to apply such pressure, but the rod 120 may be in direct contact with the user's wrist in some versions, or located underneath flexible material of the wearable support 32 to protrude into the flexible material (e.g., beneath a flexible layer) to provide therapy.

Figure 20C:
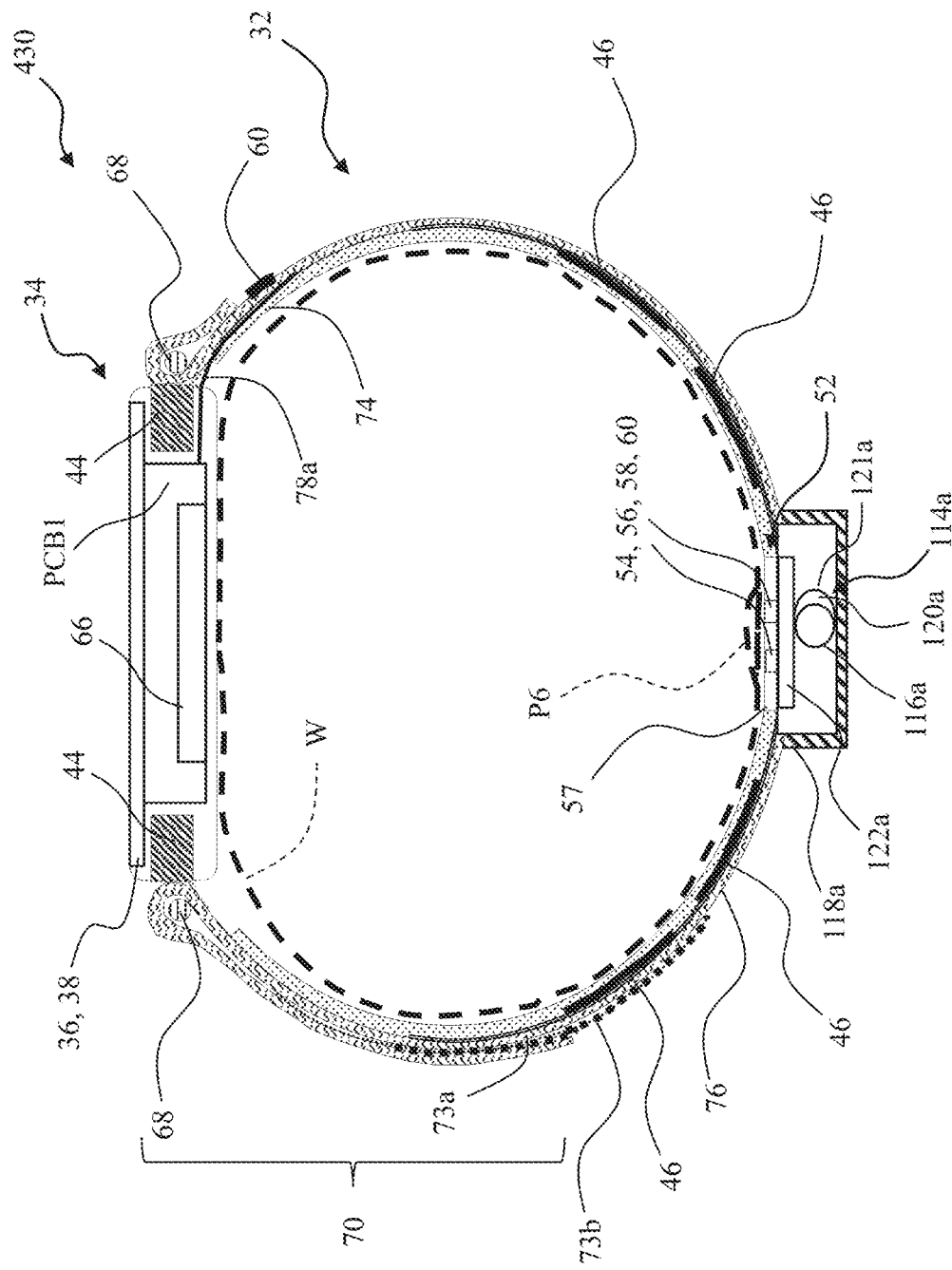
FIG. 20C is a cross-sectional view of a wearable device illustrating a sensor housing being placed against an acupressure point of the user during therapy.
Figure 20D:
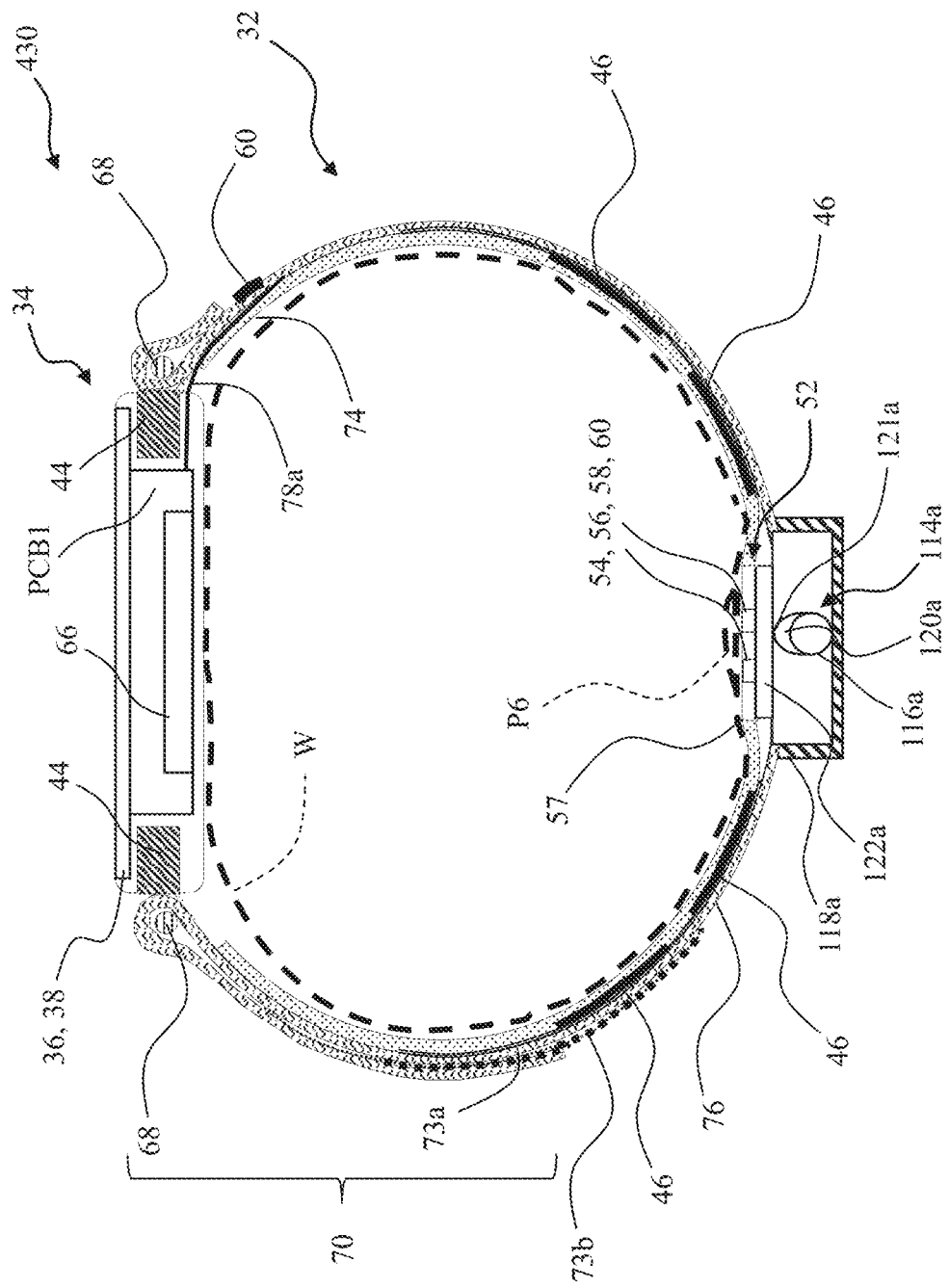
FIG. 20D is a cross-sectional view of the wearable device illustrating actuation of a rotary actuator to apply pressure to the acupressure point.

FIGS. 20C and 20D illustrate a variation of the wearable device 430 that employs a rotary actuator 114a to apply pressure to the acupressure point P6 of the user. The rotary actuator 114a is connected to the controller 66 to be activated by the controller 66. The rotary actuator 114a is mounted to a rigid housing 118a. The housing 118a is attached and fixed to the second flexible layer 76 using an attachment method as previously described, or any suitable attachment method. The rotary actuator 114a comprises a motor 116a (e.g., a 3V, reversible DC motor) that is mounted to the housing 118a and a rotationally-movable cam 120a connected to a drive shaft of the motor 116a to rotate relative to the housing 118a. A pressure-applying body 122a is attached and fixed to the sensor housing 57 to move with actuation of the cam 120a. During actuation of the rotary actuator 114a, as shown in FIG. 20D, the cam 120a has a cammed portion 121a that rotates toward the acupressure point P6 to move the pressure-applying body 122a and the sensor housing 57 to apply such pressure, but the pressure-applying body 122a may be in direct contact with the user's wrist in some versions, or located underneath flexible material of the wearable support 32 to protrude into the flexible material (e.g., beneath a flexible layer). In some versions, the cam 120a may act as the pressure-applying body and may be located beneath the sensor housing 57 to move the sensor housing 57 to apply such pressure, but the cam 120a may be in direct contact with the user's wrist in some versions, or located underneath flexible material of the wearable support 32 to protrude into the flexible material (e.g., beneath a flexible layer) to provide therapy.

Figure 21A:
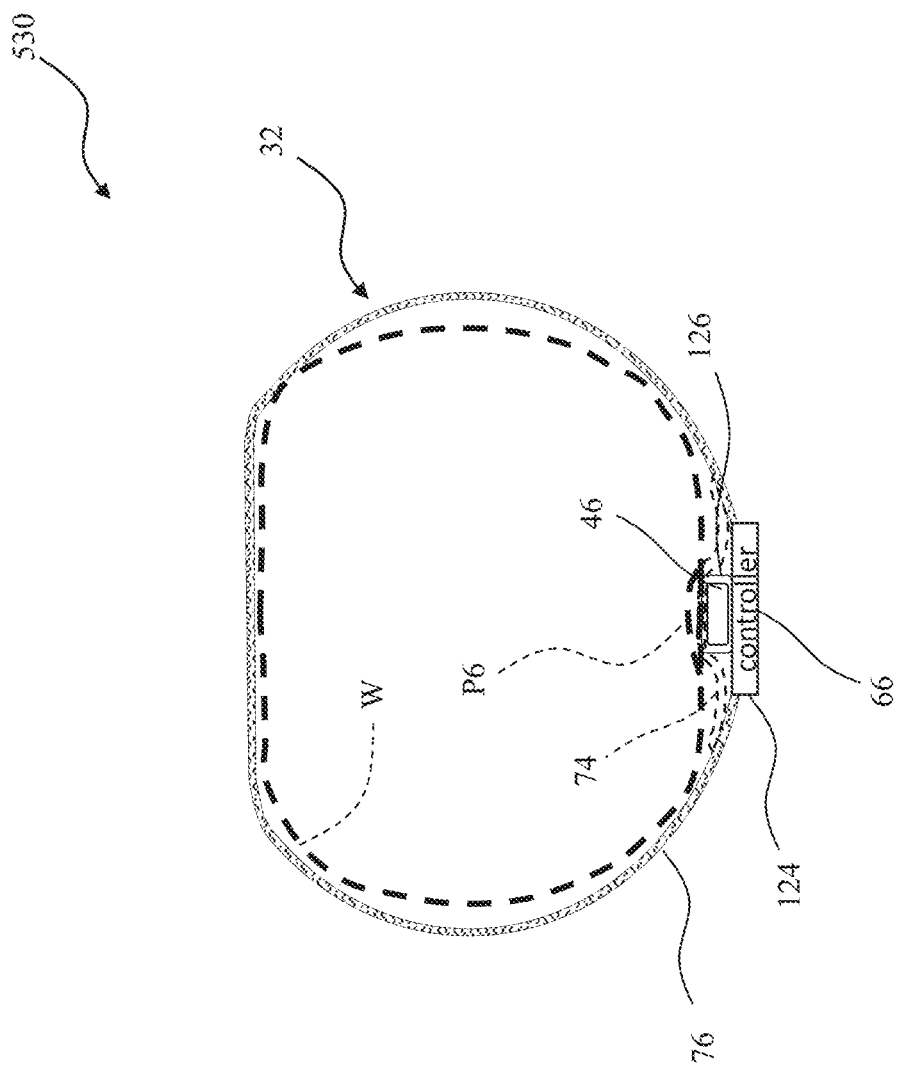
FIG. 21A is a cross-sectional view of a wearable device including a wrist band and a haptic generator being placed against the acupressure point of the user during therapy.

FIG. 21A illustrates another wearable device 530 that comprises the wearable support 32 and a haptic generator 46. In this version, the wearable support 32 includes an elastic wrist band that completely encircles the user's wrist. The haptic generator 46 is connected to the controller 66 to provide therapy to the user, such as providing one or more of the haptic therapies previously described. For instance, the haptic generator 46 may be activated to output a repeating pattern and/or may be activated to generally vibrate against the acupressure point P6 to calm the user. In this version, the controller 66 is located on the wearable support 32 in a housing 124 fixed to the wrist band. The haptic generator 46 is disposed in an enclosure 126 of the housing 124. In some versions, the haptic generator 46 may be attached to the housing 124 and exposed outside of the housing 124 to be in direct contact with the user when the wearable support 32 is worn by the user. In other versions, the haptic generator 46 may be captured between the flexible layers 74, 76 such that vibrations from the haptic generator 46 are able to be felt/sensed by the user. In some versions, a band tensioner 128, described further below can be employed to first tighten the wrist band about the user's wrist W to a predetermined tension (which can be measured by any suitable pressure sensor, strain gauge, or the like connected to the controller 66). Thereafter, the haptic generator 46 can be activated for therapy.

Figure 21B:
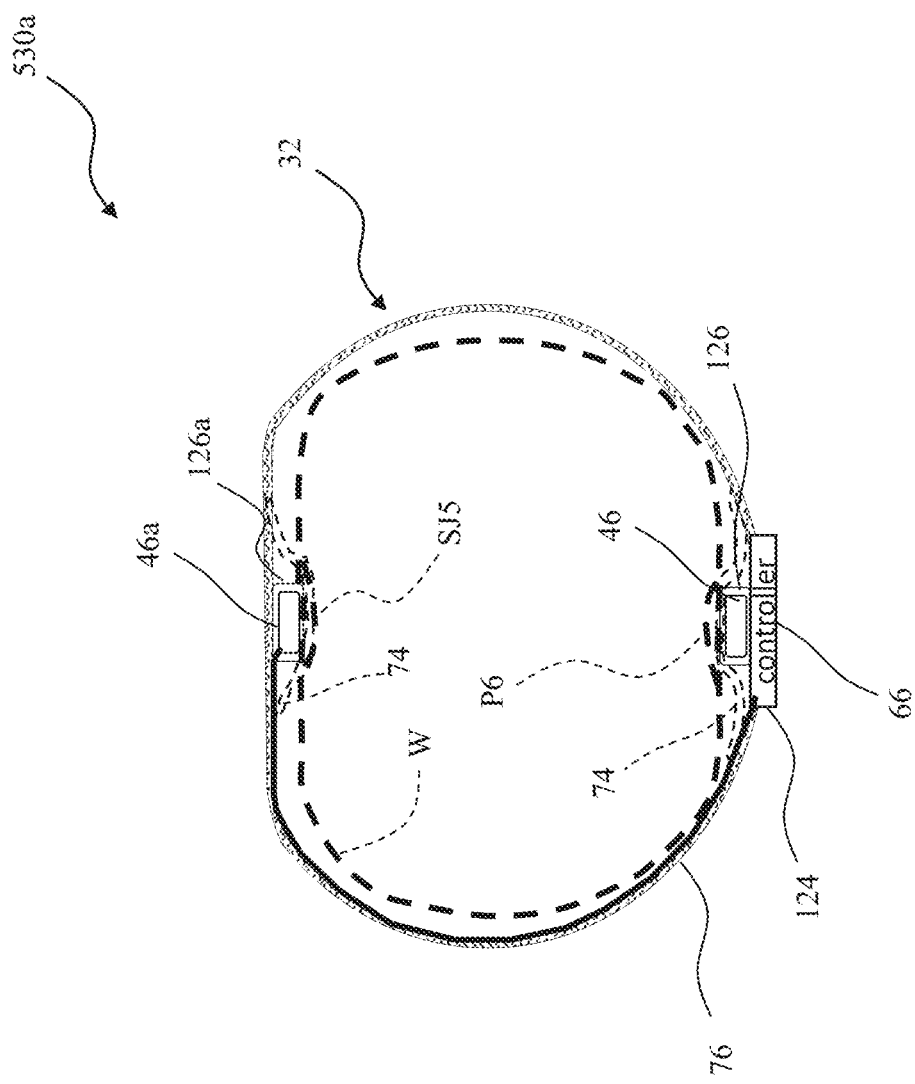
FIG. 21B is a cross-sectional view of a wearable device including a wrist band and haptic generators being placed against two different acupressure points of the user during therapy.
Figure 21C:
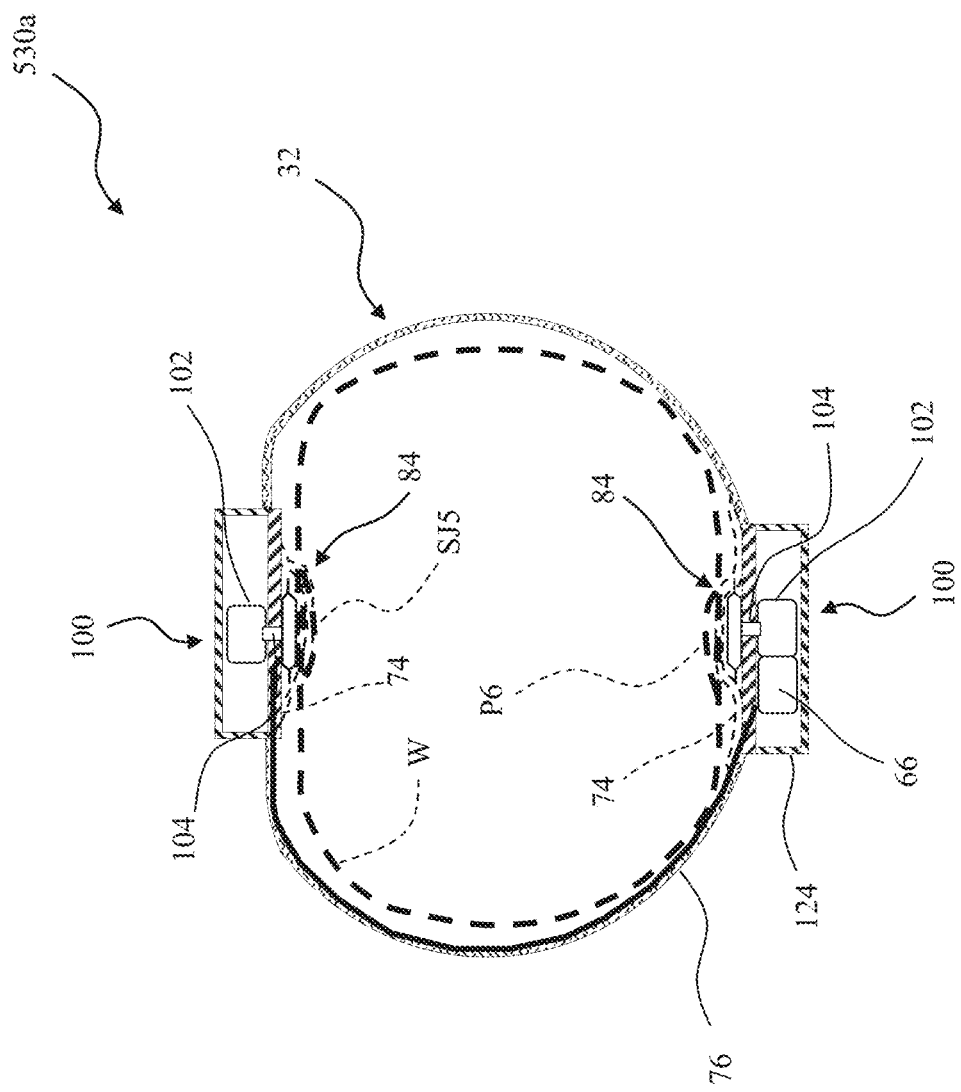
FIG. 21C is a cross-sectional view of a wearable device including a wrist band and inflatable bladders being placed against two different acupressure points of the user during therapy.

FIG. 21B shows another wearable device 530a, similar to the wearable device 530, but in this case a second haptic generator 46a is attached to the flexible layer 76 (and in some versions, captured between the flexible layers 74, 76, opposite the haptic generator 46). The second haptic generator 46a is connected to the controller 66 (see wired connection through flexible layer 76) to provide therapy to the user by providing haptic therapy to another acupressure point SJ5 (also referred to as San Jiao 5 or triple warmer 5) on the opposite side of the user's wrist W from the acupressure point P6. In some forms of therapy, both the haptic generators 46, 46a are activated simultaneously to vibrate against the two acupressure points P6, SJ5. In some versions, the band tensioner 128, described further below, can be employed to first tighten the wrist band about the user's wrist W to a predetermined tension (which can be measured by any suitable pressure sensor, strain gauge, or the like connected to the controller 66). Thereafter, the haptic generators 46, 46a can be activated for therapy. The haptic generators 46, 46a can be activated simultaneously, sequentially, in the same repeating pattern, in different repeating patterns, combinations thereof, and the like. In some versions, as shown in FIG. 21C, the haptic output devices comprise inflatable bladders 84, both similar to the first inflatable bladder 84 described above. In this case, the inflatable bladders 84 can be inflated to apply pressure against the acupressure point P6 and the acupressure point SJ5 to provide pressure therapy to the user. Separate inflators 100 could be used to inflate/deflate the inflatable bladders 84, or a single inflator 100 with a conduit connecting both the inflatable bladders 84 could be used.

Figure 22:
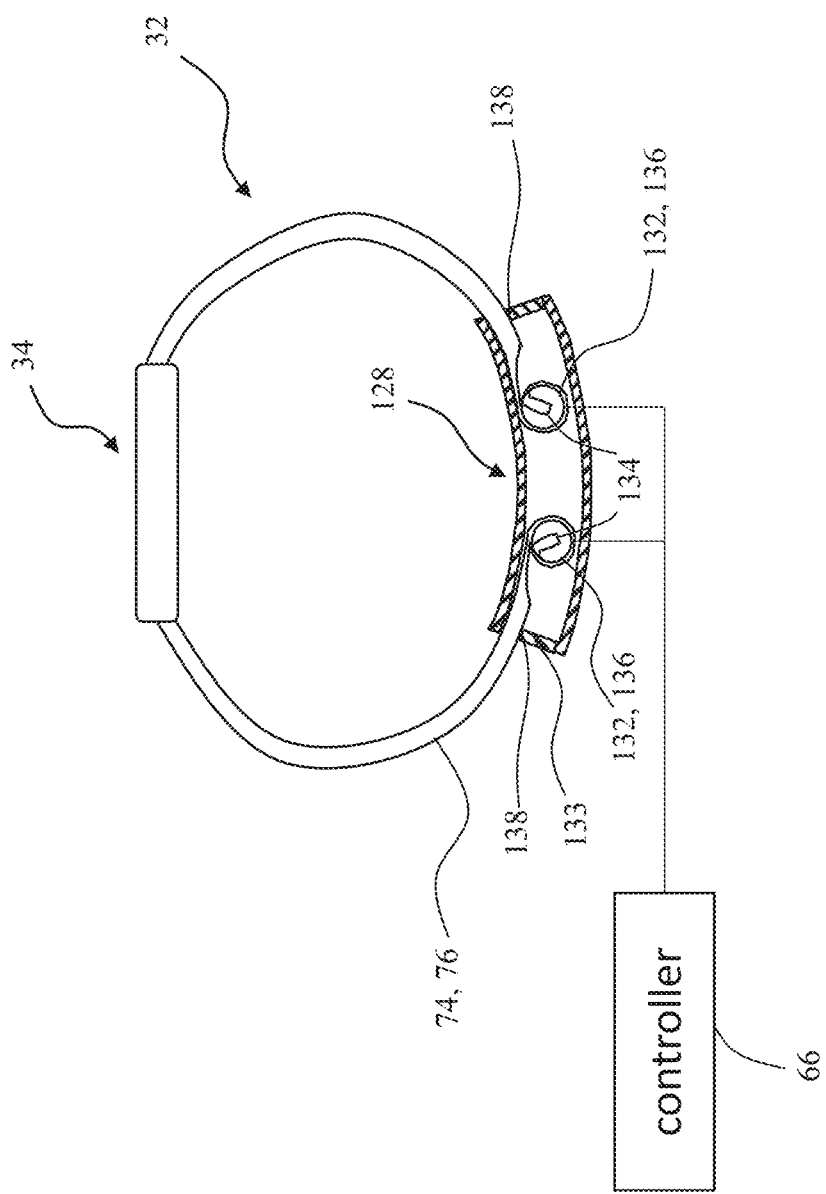
FIG. 22 is a cross-sectional view of a band tensioner for placing a wrist band in tension.

FIG. 22 is a cross-sectional view of the band tensioner 128 that can be used with any of the wearable devices. The band tensioner 128 comprises a rigid tensioner housing 133 and a pair of winders or drums 132 on which opposing ends 134 of the wrist band can be fixed and on which the wrist band can be wound/unwound. As the drums 132 rotate, the wrist band winds or unwinds on the drums 132 and changes length, thereby tightening or loosening the wrist band when placed on the user's wrist. A motor 136 operates each of the drums 132. The motors 136 have motor housings fixed to the tensioner housing 133. The drums 132 are rotatably mounted to the tensioner housing 133 to rotate relative to the tensioner housing 133 to increase or reduce tension in the wrist band. The tensioner housing 133 may be open at each end or have slots 138 to receive the wrist band and guide the wrist band with respect to the drums 132. In some versions, the wrist band, by virtue of the band tensioner 128 acts as a pressure-applying body. In some versions, other mechanisms are employed to tighten or loosen the wrist band, such as gears that have a rack-type engagement with the wrist band, frictional mechanisms that pull/release the wrist band, linear actuators that pull/extend one or both ends of the wrist band relative to a housing, electronic solenoids connected to one or both ends of the wrist band, and the like.

Figure 23:
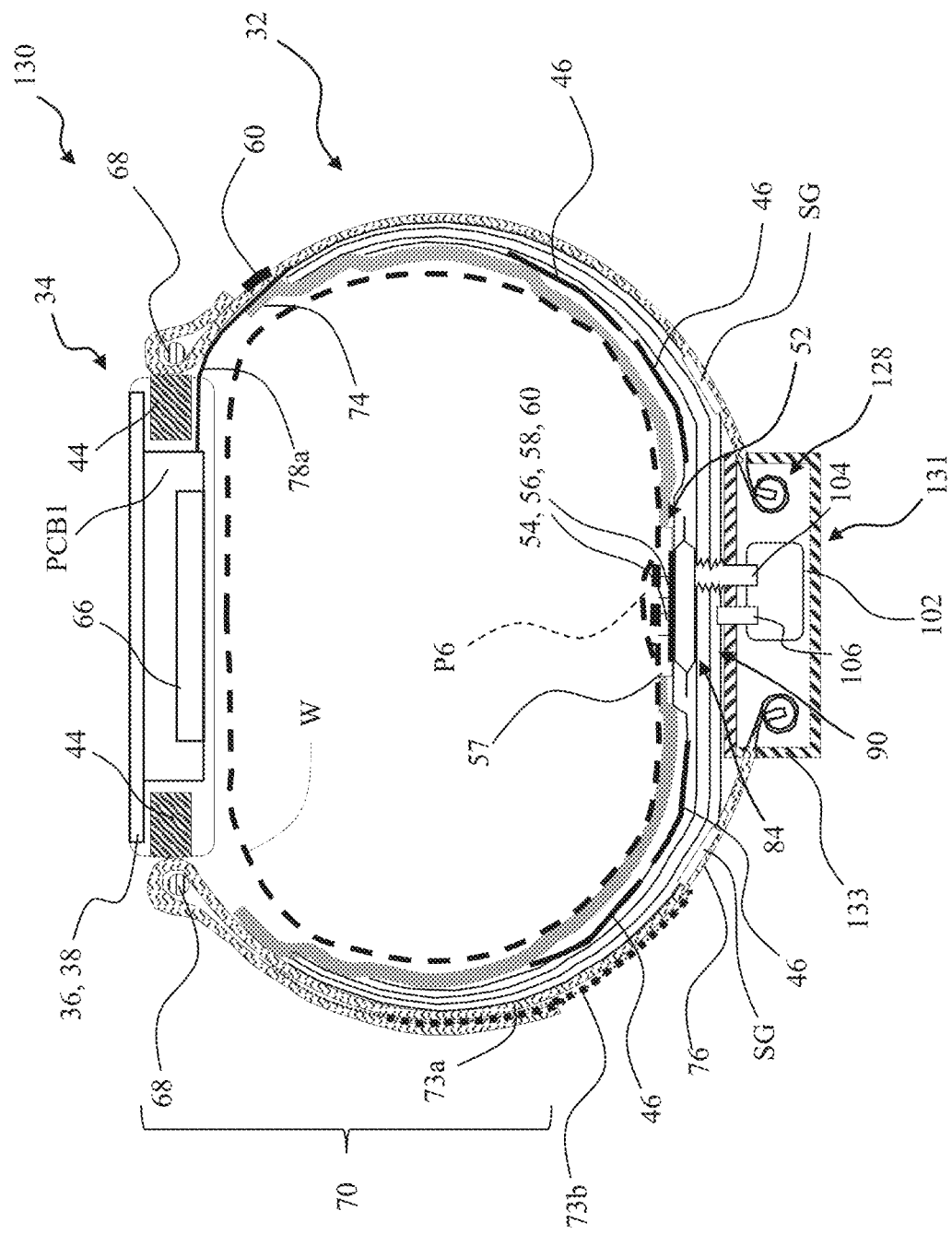
FIG. 23 is a cross-sectional view of a wearable device including a wrist band with inflatable bladders and a band tensioner.

FIG. 23 shows the band tensioner 128 being integrated into the wearable device 130 of FIGS. 10-15 to control tension on the second flexible layer 76. In some versions, the band tensioner 128 may be controlled by the controller 66 in a cooperative manner to provide therapy to the user and/or to take measurements of one or more physiological parameters of the user. One or more of the pressure sensors 58, strain gages SG, or other type of tension sensor connected to the controller 66 (wired or wirelessly), may be used to measure tension of the wrist band on the user's wrist to determine how much to wind/unwind the wrist band via the band tensioner 128. See, for example, the strain gages SG shown in FIG. 23. When taking blood pressure measurements, it may be desirable to first tighten the wrist band on the user's wrist to a first predetermined pressure/tension before inflating the first inflatable bladder 84 and/or the second inflatable bladder 90. Inflation may also occur before tensioning and/or simultaneously therewith. The combination of tensioning the wrist band via the band tensioner 128 and inflation of the first and/or second inflatable bladders 84, 90 can be helpful to ensure pressure capable of shutting off blood flow in the local artery. Tightening and loosening of the wrist band can also provide haptic feedback to the user in the training and therapy modes previously described. Tightening and loosening of the wrist band may also provide haptic therapy in response to elevated/lowered physiological parameters, etc., as previously described. Tightening of the wrist band can also assist in placing the one or more haptic output devices against the user's skin.

FIG. 24 illustrates another wearable device 630 comprising haptic generators 46, thermal elements 48, optical sensors 54, light emitting diodes 56, temperature sensor 59, and EEG sensors 140 (other sensors as previously described may also be present). The EEG sensors 140 are integrated into a wearable support 632 in the form of a headband 642 that is connected to a pair of earpieces 644. The haptic generators 46 are mounted to the earpieces 644 and spaced along the earpieces 644 to be positioned against a side of the user's head adjacent to their ears and acupressure points surrounding the user's ear. The haptic generators 46, thermal elements 48, optical sensors 54, light emitting diodes 56, and other sensors (not shown) can be used as previously described. Additionally, the controller 66 may be integrated into one of the earpieces 644 and a port 146 (USB, USB-C, etc.) may be used to connect the wearable device 630 (may be present on any of the wearable devices) to a computer. A user interface UI including one or more user input devices may also be located on the earpiece 644 to operate the wearable device 630.

Figure 25A:
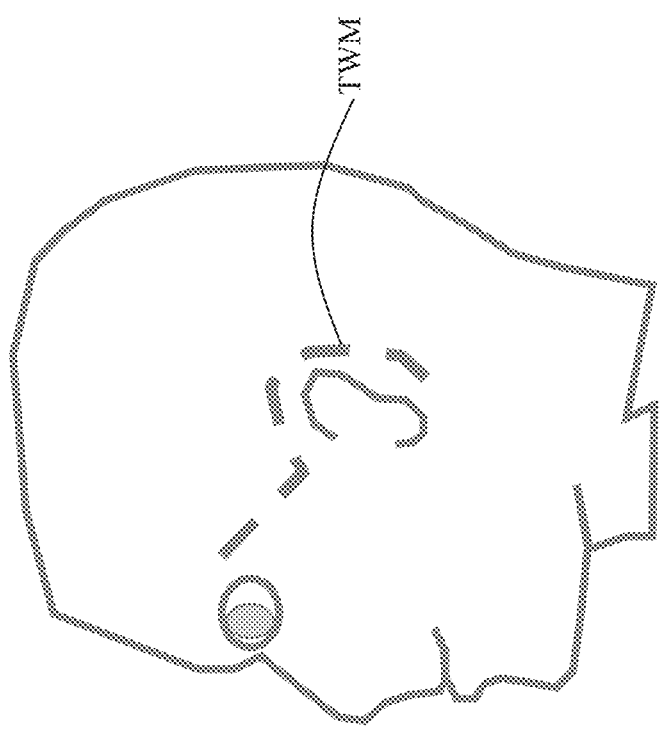
FIG. 25A illustrates a meridian path of the user.
Figure 26:
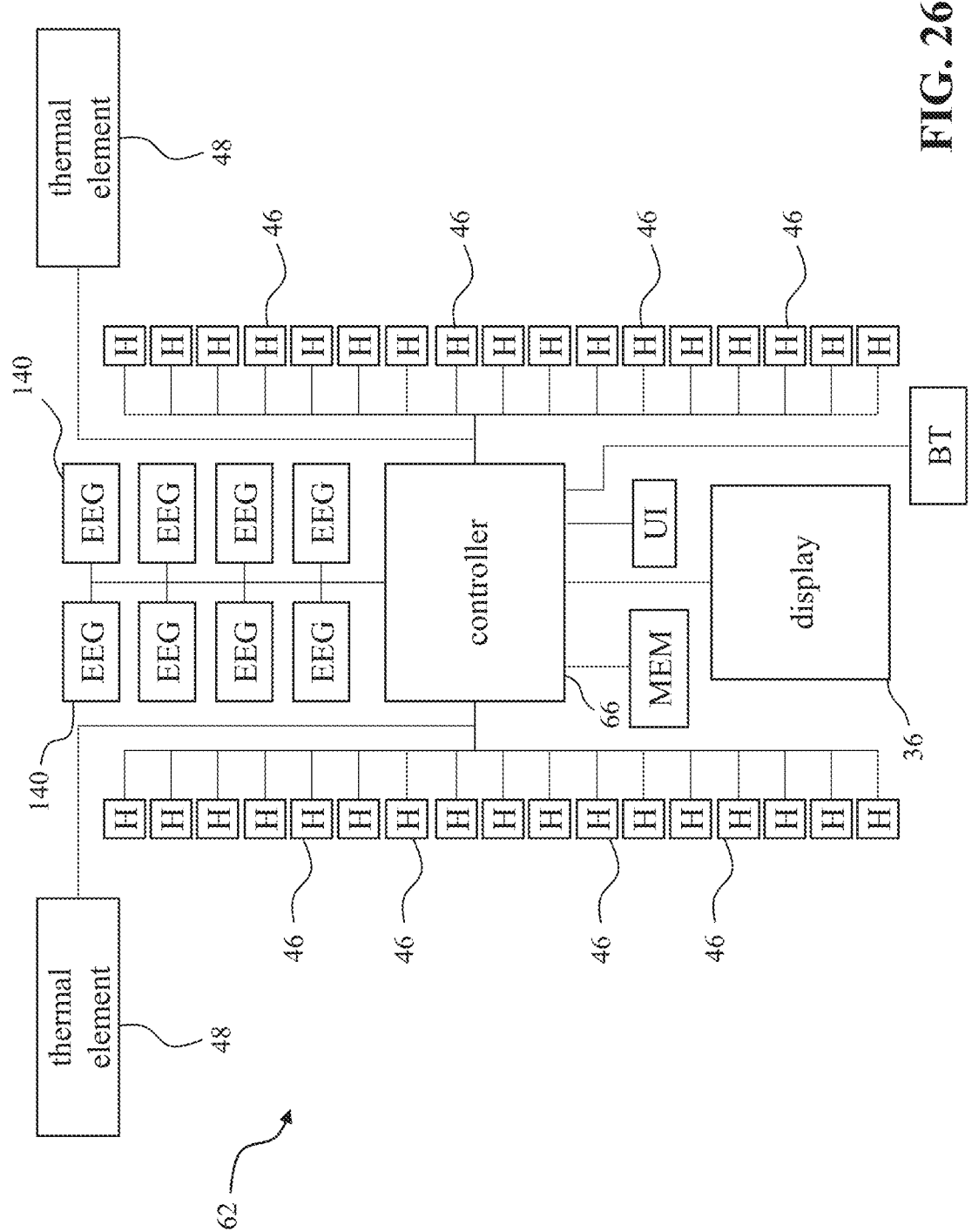
FIG. 26 is a block diagram of a control system for the wearable device of FIG. 24.

In this version, the EEG sensors 140 additionally measure one or more brainwaves (see FIG. 25) of the user and can determine whether the user is in a relaxed state or a state of elevated stress or anxiety. During therapy, the haptic generators 46 can be activated in sequence, e.g., from front to back, to provide therapy to the user. The sequence may include at least one haptic generator 46 being active at all times to generate haptic output, or there may be pauses between activation of the next haptic generator 46 in the sequence. Possible sequences may also include waves of activation, e.g., repeated activation of the haptic generators 46 from front to back, back to front, combinations thereof, and the like. These patterns may be utilized for purposes of training and therapy, as previously described, or for other purposes. The controller 66 may be configured to activate the plurality of haptic generators 46 in a predetermined sequence in which two or more of the plurality of haptic generators 46 are activated at different levels, at different times, or at different levels and different times. Activation of the haptic generators 46 may also replicate a therapist following a meridian of the user by sequentially activating (and deactivating) the haptic generators 46 to mimic a therapist's finger tracing around the user's ear as shown in the illustration of FIG. 25A to follow the user's meridians, such as the triple warmer meridian TWM. Such activation and deactivation may occur one time or a plurality of times over the duration of therapy.

Figure 27:
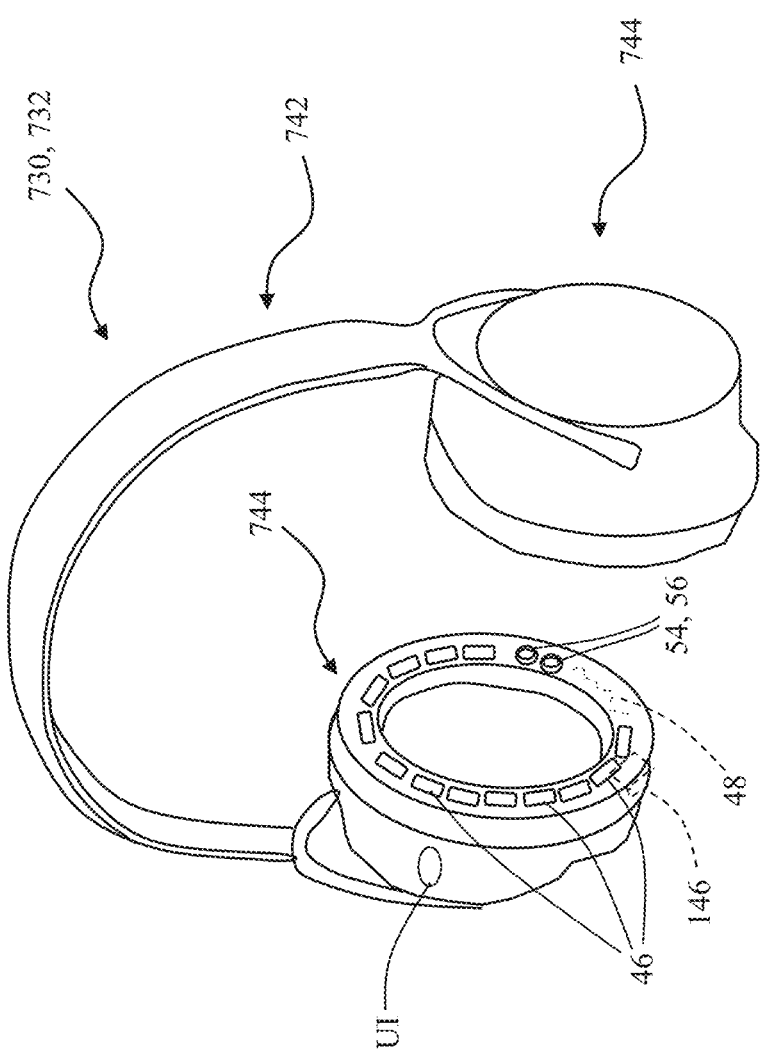
FIG. 27 is a perspective view of a wearable device including a pair of ear pieces.

FIG. 27 illustrates another wearable device 730 comprising haptic generators 46, thermal elements 48, optical sensors 54, and light emitting diodes 56 (other sensors as previously described may also be present). The haptic generators 46 are mounted to earpieces 744 connected by a flexible head band 742 and spaced about the earpieces 744 to be positioned against a side of the user's head adjacent to their ears and acupressure points surrounding the user's ear. The haptic generators 46, thermal elements 48, optical sensors 54, light emitting diodes 56, and other sensors (not shown) can be used as previously described. Additionally, the controller 66 may be integrated into one of the earpieces 744 and a port 146 (USB, USB-C, etc.) may be used to connect the wearable device 630 (may be present on any of the wearable devices) to a computer. A user interface UI including one or more user input devices may also be located on the earpiece 744 to operate the wearable device 730. The wearable device 730 may be headphones for also playing sounds (e.g., with speakers), in addition to providing the other therapeutic functions described herein.

During therapy, the haptic generators 46 can be activated in sequence, e.g., from front to back, to provide therapy to the user. The sequence may include at least one haptic generator 46 being active at all times to generate haptic output, or there may be pauses between activation of the next haptic generator 46 in the sequence. Possible sequences may also include waves of activation, e.g., repeated activation of the haptic generators 46 from front to back, back to front, combinations thereof, and the like. These patterns may be utilized for purposes of training and therapy, as previously described, or for other purposes. The controller 66 may be configured to activate the plurality of haptic generators 46 in a predetermined sequence in which two or more of the plurality of haptic generators 46 are activated at different levels, at different times, or at different levels and different times. Activation of the haptic generators 46 may also replicate a therapist following a meridian of the user by sequentially activating (and deactivating) the haptic generators 46 to mimic a therapist's finger tracing around the user's ear as shown in the illustration of FIG. 25A to follow the user's meridians, such as the triple warmer meridian TWM. Such activation and deactivation may occur one time or a plurality of times over the duration of therapy.

Figure 28:
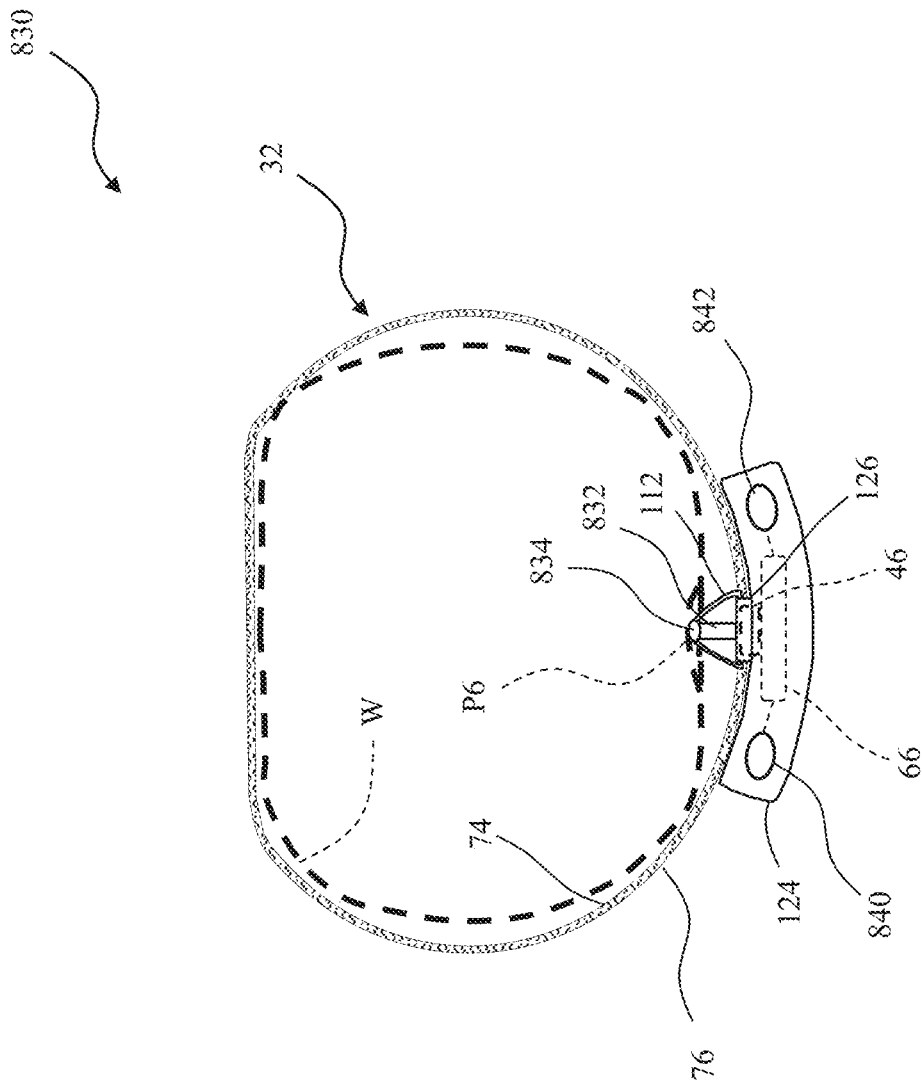
FIG. 28 is a cross-sectional view of a wearable device including a wrist band and a haptic generator being placed against the acupressure point of the user during therapy.
Figure 29:
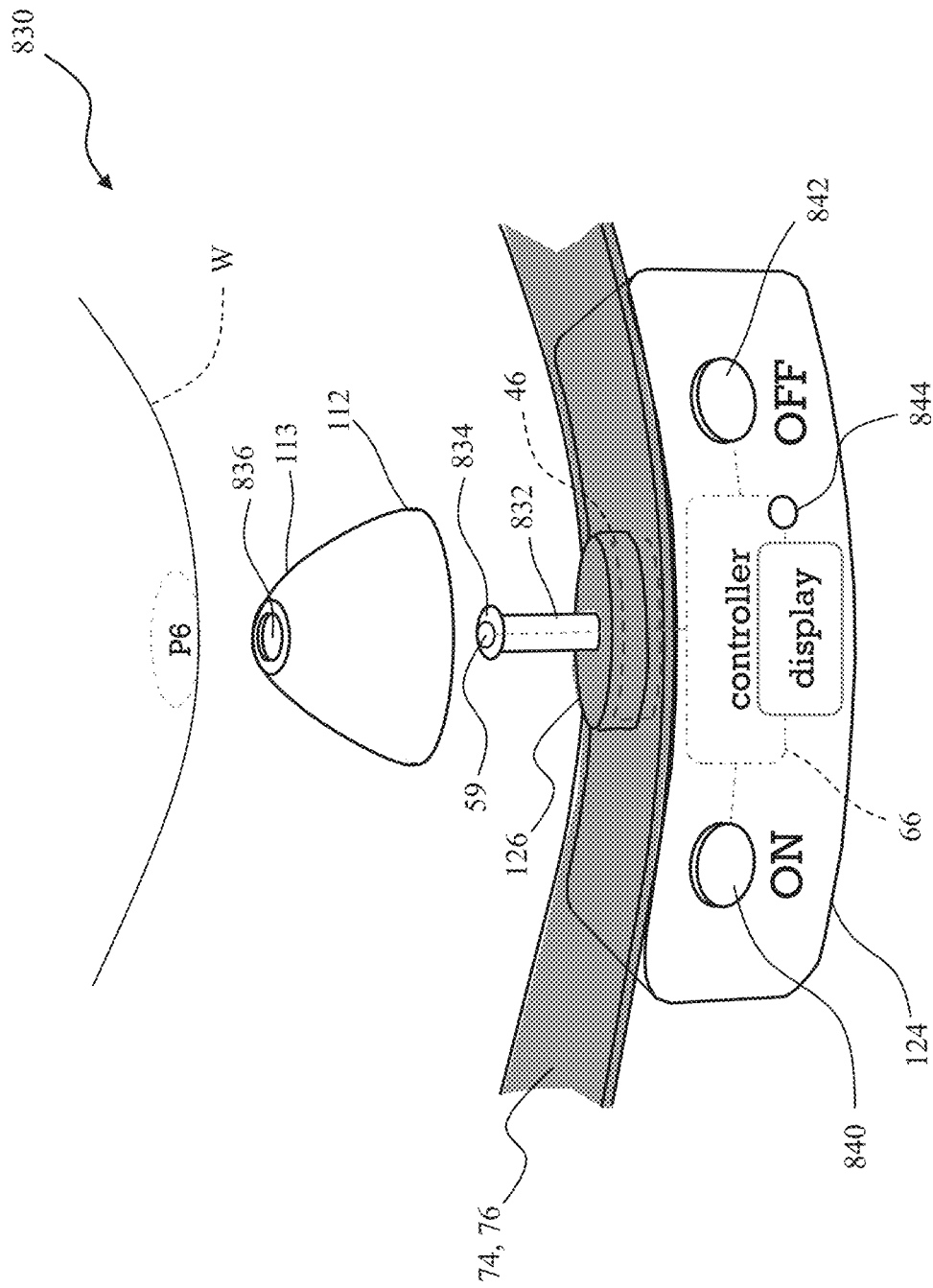
FIG. 29 is a partially exploded view of the wearable device of FIG. 28.
Figure 30:
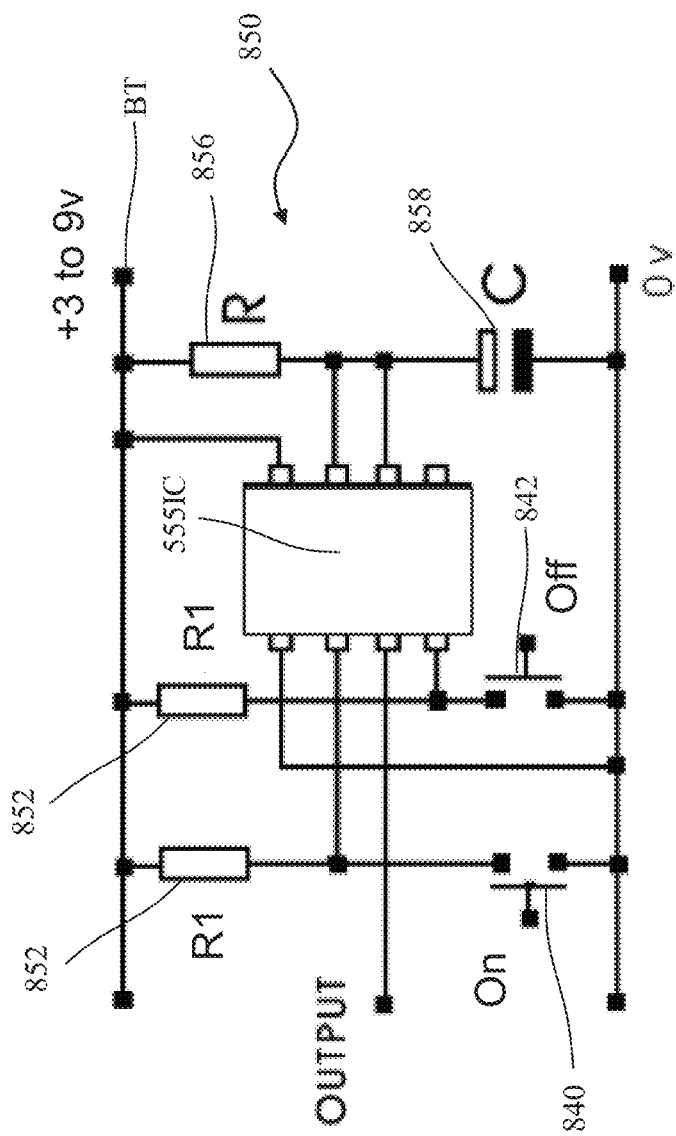
FIG. 30 is an electrical schematic diagram.

FIGS. 28-30 illustrate another wearable device 830 that comprises the wearable support 32 and a haptic generator 46. In this version, the wearable support 32 includes a wrist band that completely encircles the user's wrist that may be elastic, semi-elastic, inelastic, combinations thereof, or the like, and able to stretch or be adjusted to fit to most users. The haptic generator 46 is connected to the controller 66 to provide therapy to the user, such as providing one or more of the haptic therapies previously described. For instance, the haptic generator 46 may be activated to output a repeating pattern and/or may be activated to generally vibrate against the acupressure point P6 to calm the user, provide nausea relief, or the like. In this version, the controller 66 is located on the wearable support 32 in a housing 124 fixed to the wrist band. The haptic generator 46 is disposed in an enclosure 126 of the housing 124 (e.g., in a boss portion of the housing 124 that extends upwardly from a main portion of the housing 124). In some versions, the haptic generator 46 may be attached to the housing 124 and exposed outside of the housing 124 to be in direct contact with the user when the wearable support 32 is worn by the user. The haptic generator 46 and any other electronic components may be sealed in the housing 124 to prevent water intrusion. In other versions, the haptic generator 46 may be captured between the flexible layers 74, 76 such that vibrations from the haptic generator 46 are able to be felt/sensed by the user. In some versions, a band tensioner 128, described above can be employed to first tighten the wrist band about the user's wrist W to a predetermined tension (which can be measured by any suitable pressure sensor, strain gauge, or the like connected to the controller 66). Thereafter, the haptic generator 46 can be activated for therapy.

A projection 112 in the form of a massage head, such as a separate dome-shaped cap, is connected to the housing 124, such as around the enclosure 126. The projection 112 extends from the wrist band to apply pressure on the acupressure point P6 of the user's wrist W when the wrist band is worn by the user and properly positioned so that the projection 112 is applying pressure to the acupressure point P6. The projection 112 may be spherically-shaped, hemispherically shaped, or have any suitable shape for engaging the user's skin. The projection 112 may have a smooth arcuate portion 113 that is located to engage the user's skin. In some versions, multiple projections 112 may be provided to engage the user's skin. See FIGS. 28A and 28B, for example, which shows an array of multiple projections 112 with integrated posts 832 and heads 834 having snap-fit features (e.g., snap-fit protrusions, or may be semi-spherical heads, as shown in FIG. 28C). The snap-fit features engage openings in a separate retainer plate 837 that secures the housing 124 and the projections 112 to the wrist band by virtue of the projections 112 being fixed to the housing 124. The projections 112 are shaped to penetrate through openings in the wrist band to engage and secure the retainer plate 837. The one or more projections 112 may be substantially rigid compared to the wrist band, and be formed of plastic, such as high-density polyethylene (HDPE), polystyrene (PS), polyethylene terephthalate (PET), or the like. In some cases, a layer 875, such as a soft fabric layer, silicone layer, a low friction coating layer (e.g., Teflon), etc. may be placed over the projection 112 to act as a skin interface between the projection 112 and the user's skin. See FIG. 28E, for example. The projections 112 may be connected to the wrist band and/or the housing 124 in any suitable manner, including welding, adhesive, fasteners, sewing, heat staking, or the like.

In the version shown in FIG. 29, a post 832 extends upwardly from the enclosure 126 in which the haptic generator 46 resides. In the version shown, the post 832 is fixed to the housing 124. A head 834, such as a spherical shaped-head, is connected to the post 832 and is sized to fit through an opening 836 in the projection 112 in a snap-fit manner (the head 834 is slightly larger than the opening 836 to retain the head 834). The haptic generator 46, during operation, causes vibration of the post 832 and/or the head 834 to vibrate the one or more projections 112 to provide haptic therapy to the acupressure point P6.

When the projection 112 is connected to the housing 124 (see FIG. 28), the one or more flexible layers 74, 76 are captured (trapped) between the projection 112 and the housing 124. The post 832 and the head 834, which may be integrally formed together, are sized to fit through a hole or opening formed in the one or more flexible layers 74, 76 to further secure the housing 124 and the projection 112 to the one or more flexible layers 74, 76. Capturing of the one or more layers 74, 76 is shown in FIG. 29. The projection 112 can be connected to the housing 124 in any suitable manner, e.g., snap-fit, press-fit, fasteners, adhesive, or the like to connect the projection 112 and/or the housing 124 to the one or more flexible layers 74, 76. In some versions, the post 832 is fixed to the projection 112 and penetrates the flexible layers 74, 76 to connect to the housing 124. Variations for connecting the housing 124 and the one or more projections 112 to the wrist band are shown in FIGS. 28A and 28C through 28E. The one or more flexible layers 74, 76 can be captured between the projection 112 and the housing 124 and/or the one or more flexible layers 74, 76 may be routed through the housing 124. In some cases, ends of the one or more flexible layers 74, 76 are attached the housing 124 (e.g., via adhesive, fasteners, welding, etc.).

As shown in FIG. 29, the controller 66 may be connected to one or more haptic generators 46 (shown as vibration motors in this version). The user interface UI in this version may comprise one or more buttons, such as an "on" button 840 (an example of a therapy trigger) and/or an "off" button 842. The display of the user interface UI may be configured to display the current state of the wearable device 830. The one or more haptic generators 46 may be disposed in the enclosure 126 in proximity to the projection 112 to cause vibrations of the projection 112, the post 832, and/or the head 834. These vibrations provide haptic therapy (vibration therapy) to the user by focusing such energy on the acupressure point P6 on the wrist W of the user. The haptic therapy may be controlled in any suitable manner, including in any of the ways described herein to provide relief to the user.

In some versions, a temperature sensor 59 (e.g., a thermocouple) may be disposed in the head 834 and routed through the post 832 to measure a skin temperature of the user. The display may then be configured to display the measured temperature. Any suitable type of temperature sensor 59 may be employed, e.g., infrared thermometer, thermocouple, thermistor, or the like. An alarm may be generated by the controller 66 in response to the temperature measured exceeding a predetermined threshold, such as 100 degrees, 101 degrees, 101.4 degrees, or the like. The alarm may be audible, tactile, visual, or the like. The display could display the visual alarm. A speaker 844, coupled to the controller 66, could provide the audible alarm. The one or more haptic generators 46 could provide the tactile alarm. The benefit of the tactile alarm is that the user will know that their temperature has exceeded the threshold, but without alarming surrounding persons. Additional sensors, such as any of those previously described, could also be placed in the head 834 and their measurements shown on the display. Such temperature measurement functionality could be employed in any of the wearable devices disclosed herein.

FIG. 30 illustrates one possible circuit 850 that could form the controller 66 of the wearable device 830. In this circuit 850, the "on" and "off" buttons 840, 842 are momentary contact switches connected to a timer circuit, such as that provided by a 555 timer integrated circuit 555IC. Resistors 852 (e.g., 47K resistors) are connected on lines leading to the buttons 840, 842. One or more batteries BT provide power for the circuit 850. The one or more batteries BT may be a 3V coin cell battery, a 9V battery, or the like. The 555 timer integrated circuit 555IC is designed to provide power to the output for a predetermined period of time (e.g., 1 minute, 5 minutes, 10 minutes, etc.) and then automatically shutoff power to the output. In this case, the "off" button 842 acts merely as a reset in case the user wishes to discontinue powering the output before the time period set by the circuit 850 has expired. The output may be used to power the one or more haptic generators 46, the temperature sensor 59, and/or the other sensors, the display, and the like. The time period set for the circuit 850 is dependent on the value of the resistor 856 and the capacitor 858, e.g., $t = 1.1 \times R \times C$.

FIGS. 31-34 illustrate another wearable device 930 that comprises the wearable support 32 and a haptic generator 46. In this version, the wearable support 32 includes a wrist band that completely encircles the user's wrist that may be elastic, semi-elastic, inelastic, combinations thereof, or the like, and able to stretch or be adjusted to fit to most users. In this version, the controller 66 includes a circuit 950 (see FIG. 34). The haptic generator 46 is connected to the controller 66 to provide therapy to the user, such as providing one or more of the haptic therapies previously described. For instance, the haptic generator 46 may be activated to generally vibrate against the acupressure point P6 to calm the user, provide nausea relief, or the like. In this version, the controller 66 is located on the wearable support 32 in a housing 124 fixed to the wrist band. The haptic generator 46 is disposed in an enclosure 126 of the housing 124 (e.g., in a boss portion integral with a main portion of the housing 124 that extends upwardly from the main portion of the housing 124). In some versions, the housing 124 is formed of plastic and may be compact in size, e.g., just sized slightly larger than a coin cell battery. In the version shown, the housing 124 has a thickness T of 0.5 inches or less and a maximum length/width dimension of 1.25 inches (e.g., diameter D). In some versions, the thickness is from 0.2 to 0.5 inches, from 0.2 to 0.4 inches, or the like, and the maximum length/width dimension is from 0.6 to 1.0 inches, from 0.6 to 0.9 inches, or the like.

In some versions, the haptic generator 46 may be attached to the housing 124 and exposed outside of the housing 124 to be in direct contact with the user when the wearable support 32 is worn by the user. In other versions, the haptic generator 46 may be captured between the flexible layers 74, 76 such that vibrations from the haptic generator 46 are able to be felt/sensed by the user. In some versions, a band tensioner 128, described above can be employed to first tighten the wrist band about the user's wrist W to a predetermined tension (which can be measured by any suitable pressure sensor, strain gauge, or the like connected to the controller 66). Thereafter, the haptic generator 46 can be activated for therapy.

A projection 112 in the form of a massage head, such as a separate dome-shaped cap, is connected to the housing. The projection 112 extends from the wrist band to apply pressure on the acupressure point P6 of the user's wrist W when the wrist band is worn by the user and properly positioned so that the projection 112 is applying pressure to the acupressure point P6. The projection 112 may be spherically-shaped, hemi-spherically shaped, or have any suitable shape for engaging the user's skin. The projection 112 may have a smooth portion 115 (arcuate, flat, or the like) that is located to engage the user's skin. In some versions, multiple projections 112 may be provided to engage the user's skin. The projection 112 may be substantially rigid compared to the wrist band, and be formed of plastic, such as high-density polyethylene (HDPE), polystyrene (PS), polyethylene terephthalate (PET), or the like. In some cases, a layer 875 (see FIG. 28E), such as a soft fabric layer, silicone layer, a low friction coating layer (e.g., Teflon), etc. may be placed over the projection 112 to act as a skin interface between the projection 112 and the user's skin. The projections 112 may be connected to the wrist band and/or the housing 124 in any suitable manner, including welding, adhesive, fasteners, sewing, heat staking, or the like.

Figure 31:
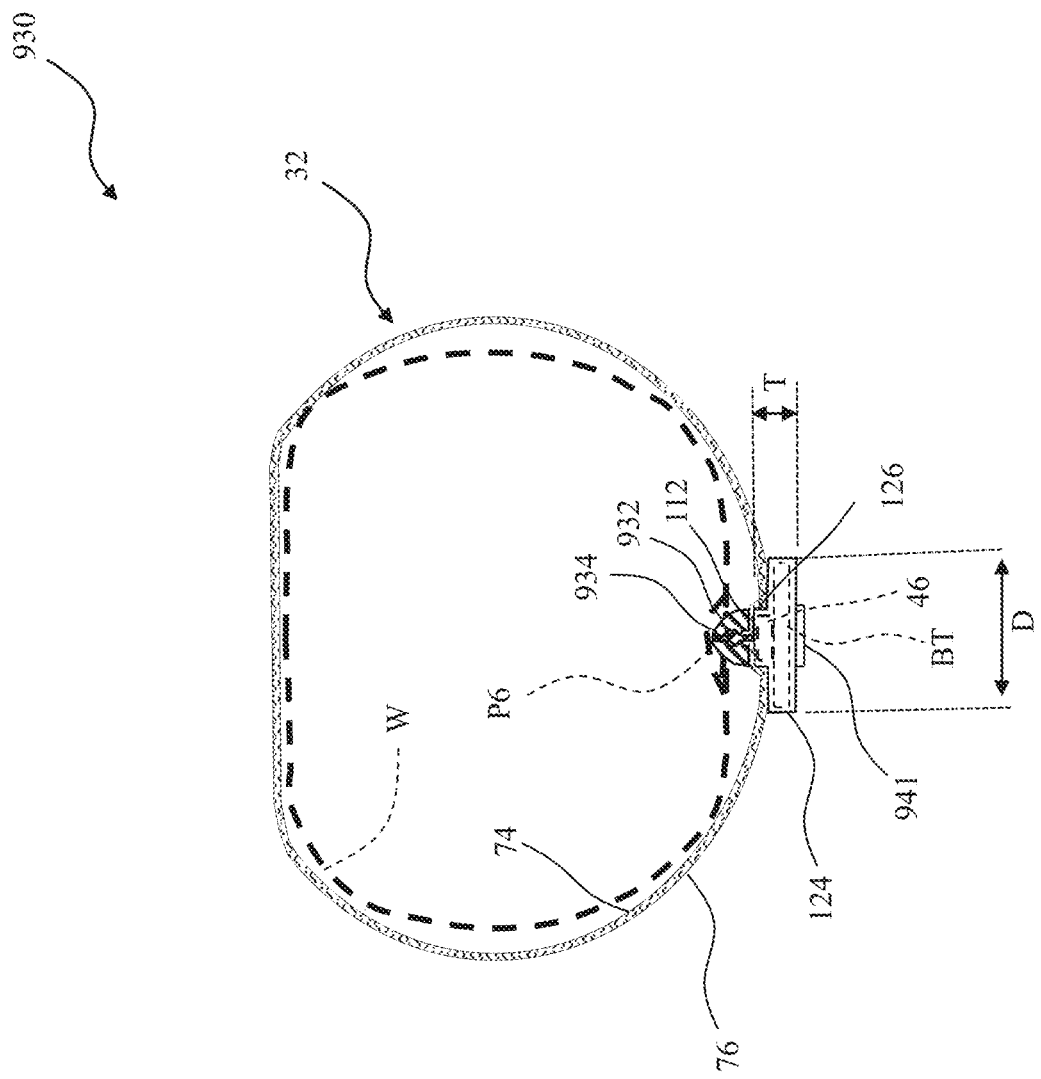
FIG. 31 is a cross-sectional view of a wearable device including a wrist band and a haptic generator being placed against the acupressure point of the user during therapy.
Figures 32, 33:
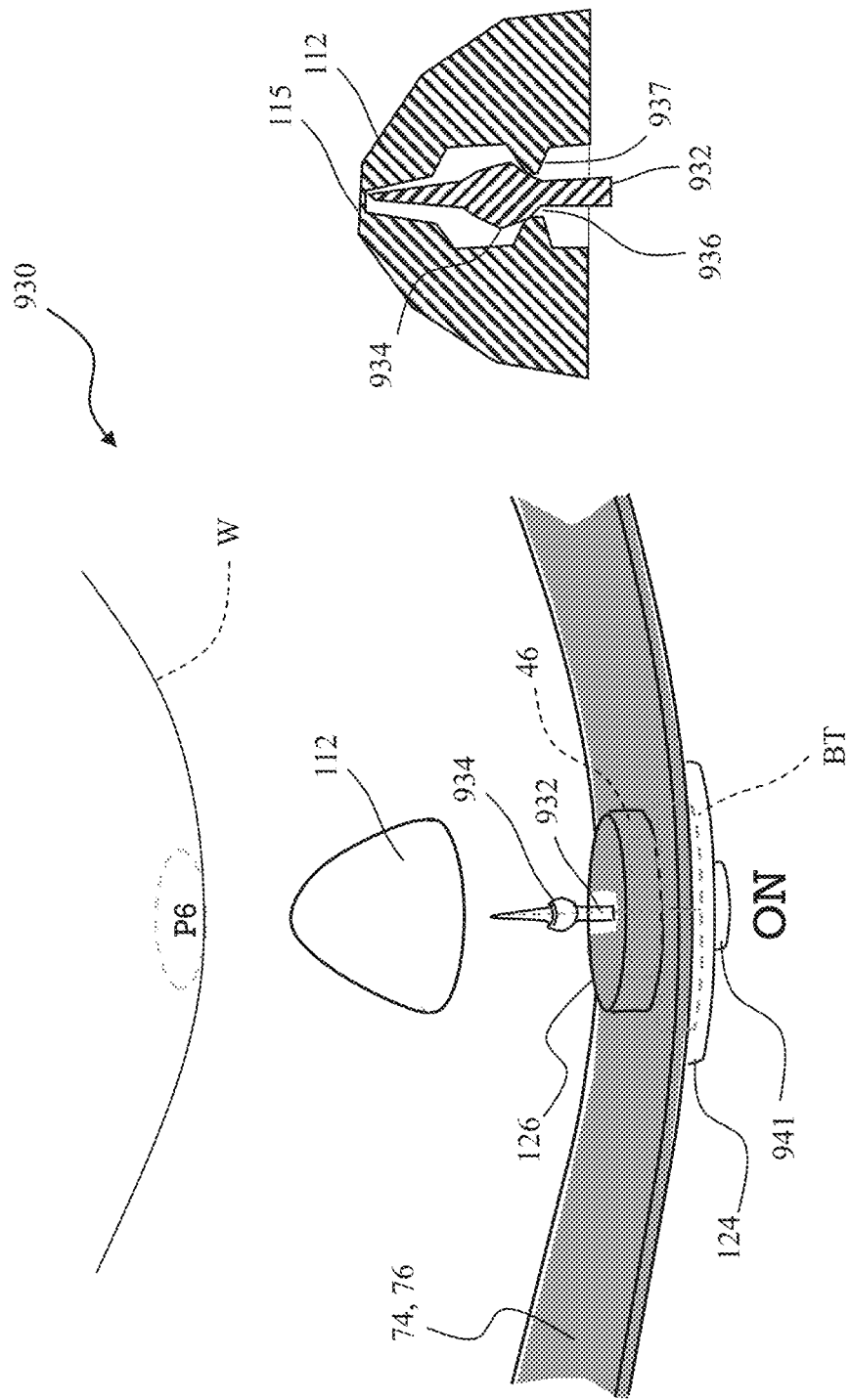
FIG. 32 is a partially exploded view of the wearable device of FIG. 31.
FIG. 33 is a cross-sectional view of a post and projection of the wearable device of FIG. 31.

In the version shown in FIGS. 31-33, a post 932 extends upwardly from the enclosure 126 in which the haptic generator 46 resides. In the version shown, the post 932 is fixed to the housing 124. An enlarged portion 934, such as a spherical shaped-portion, is connected to the post 932 (e.g., integrally formed therewith) and is sized to fit through an opening 936 in the projection 112 in a snap-fit manner. The opening 936 is formed by a radially inwardly projecting flange 937. The enlarged portion 934 is slightly larger than the opening 936 to retain the post 932 once the snap-fit connection is made. The haptic generator 46, during operation, causes vibration of the post 932 and/or the enlarged portion 934 to vibrate the one or more projections 112 to provide haptic therapy to the acupressure point P6.

When the projection 112 is connected to the housing 124 (see FIG. 31), the one or more flexible layers 74, 76 are captured (trapped) between the projection 112 and the housing 124. The post 932 and the enlarged portion 934, which may be integrally formed together, are sized to fit through a hole or opening formed in the one or more flexible layers 74, 76 to further secure the housing 124 and the projection 112 to the one or more flexible layers 74, 76. Such hole/opening may be formed separately or may be present in the flexible layers 74, 76, such as when the flexible layers 74, 76 are woven. Capturing of the one or more layers 74, 76 is shown in FIG. 32. The projection 112 can be connected to the housing 124 in any suitable manner, e.g., snap-fit, press-fit, fasteners, adhesive, or the like to connect the projection 112 and/or the housing 124 to the one or more flexible layers 74, 76. In some versions, the post 932 is fixed to the projection 112 and penetrates the flexible layers 74, 76 to connect to the housing 124. Variations for connecting the housing 124 and the one or more projections 112 to the wrist band are also contemplated. The one or more flexible layers 74, 76 can be captured between the projection 112 and the housing 124 and/or the one or more flexible layers 74, 76 may be routed through the housing 124. In some cases, ends of the one or more flexible layers 74, 76 are attached the housing 124 (e.g., via adhesive, fasteners, welding, etc.).

As shown in FIG. 32, one or more batteries BT may be connected to one or more haptic generators 46 (shown as vibration motors in this version). The user interface UI in this version may comprise one or more buttons, such as an "on" button 941 (an example of a therapy trigger). The one or more haptic generators 46 may be disposed in the enclosure 126 in proximity to the projection 112 to cause vibrations of the projection 112, the post 932, and/or the enlarged portion 934. These vibrations provide haptic therapy (vibration therapy) to the user by focusing such energy on the acupressure point P6 on the wrist W of the user. The haptic therapy may be controlled in any suitable manner, including in any of the ways described herein to provide relief to the user.

Figure 34:
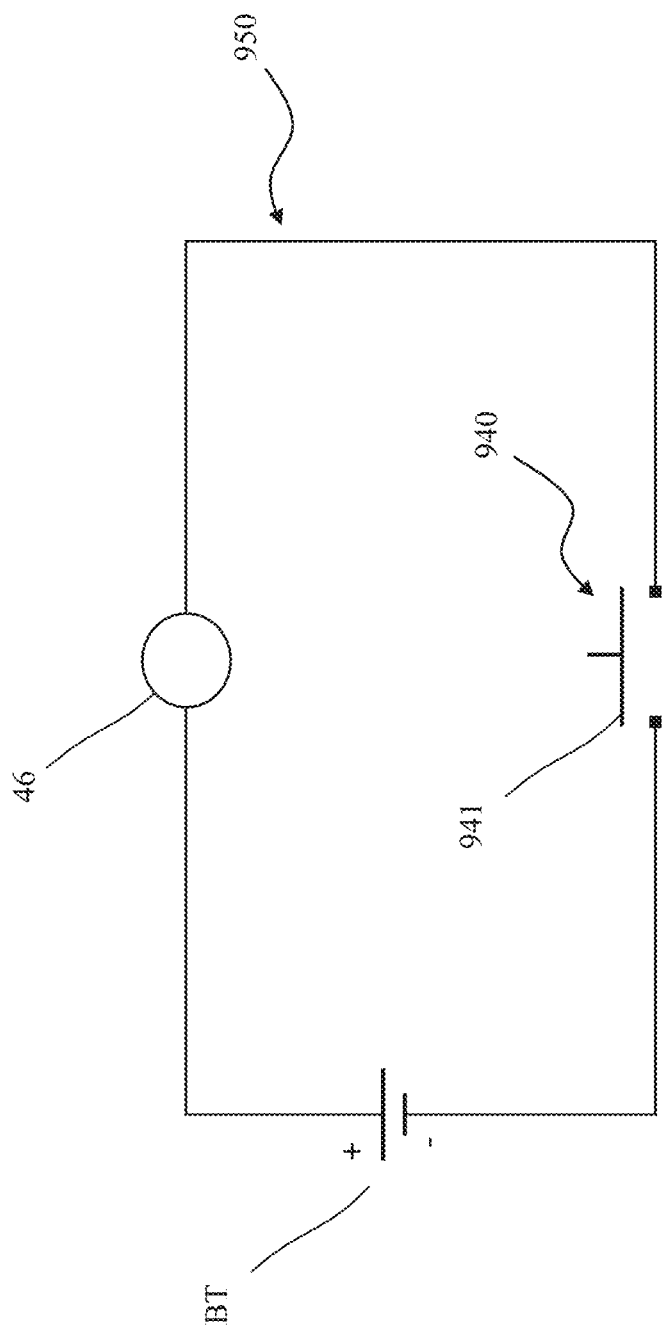
FIG. 34 is an electrical schematic diagram of a circuit.

FIG. 34 illustrates one possible circuit 950 that could form the controller 66 of the wearable device 930. In this circuit 950, the "on" button 941 is part of a momentary contact switch 940 that must be actively pressed by a user to connect power from the one or more batteries BT (e.g., a 3V coin battery) to the one or more haptic generators 46. Once released, the momentary contact switch 940 opens the circuit 950 and the batteries BT cease providing power to the haptic generators 46. In some versions, the button 941 may be a touch sensor (e.g., a capacitive sensor) that operates in the same manner as a momentary contact switch and only operates the haptic generator 46 when touched. Although not shown, one or more resistors may also be present in the circuit 950, including a resistor between the haptic generator 46 and the momentary contact switch 940. The one or more batteries BT provides power for the circuit 950. The one or more batteries BT may be a 3V coin cell battery, a 4.5V battery, a 9V battery, or the like.

Figure 35:
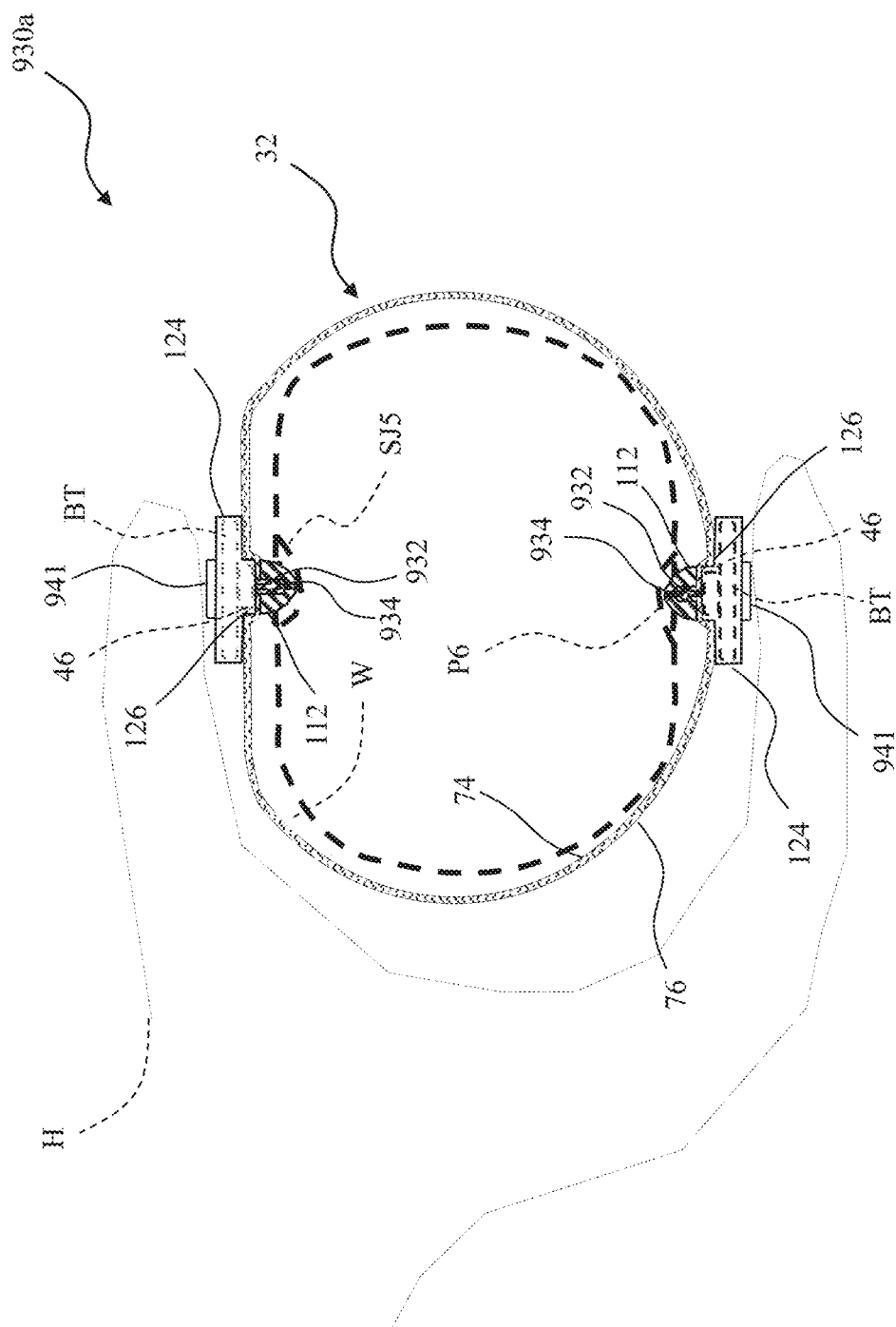
FIG. 35 is a cross-sectional view of a wearable device including a wrist band and two haptic generators being placed against acupressure points of the user during therapy.

FIG. 35 shows another wearable device 930a, similar to the wearable device 930, but in this case the same components shown previously in FIGS. 31-34 for treating the acupressure point P6 are attached to the wrist band at diametrically opposed positions, e.g., to provide haptic therapy to a top and bottom of the user's wrist W. In some versions, a second haptic generator 46, one or more additional batteries BT, a second housing 124, a second momentary contact switch 940 and associated second button 941, a second projection 112, a second post 932, and a second enlarged portion 934 are provided. The second haptic generator 46 is connected to the second controller (e.g., the one or more additional batteries BT and the second button momentary contact switch 940) or may be connected to the same controller through flexible layers 74, 76) to provide therapy to the user by providing haptic therapy to another acupressure point SJ5 (also referred to as San Jiao 5 or triple warmer 5) on the opposite side of the user's wrist W from the acupressure point P6. In some forms of therapy, both the haptic generators 46 are activated simultaneously to vibrate against the two acupressure points P6, SJ5. In some versions, the band tensioner 128, described above, can be employed to first tighten the wrist band about the user's wrist W to a predetermined tension (which can be measured by any suitable pressure sensor, strain gauge, or the like connected to the controller 66). Thereafter, the haptic generators 46 can be activated for therapy. The haptic generators 46 can be activated simultaneously, sequentially, in the same repeating pattern, in different repeating patterns, combinations thereof, and the like.

In the version shown in FIG. 35, separate buttons 941 are provided to activate the two haptic generators 46. Also, in the version shown, these are both parts of momentary contact switches and require constant activation to operate the haptic generators 46, i.e., once released, the momentary contact switches open the circuits 950 and the batteries cease providing power to the haptic generators 46. As a result, a smaller battery, such as 3V coin cell batteries can be utilized and have sufficient life to power the wearable device 930a since they only provide therapy while the user is pressing the buttons 941. See, e.g., the user's thumb and finger on their other hand H in FIG. 35 simultaneously pressing both buttons 941. The buttons 941 can be arranged as shown to project radially outwardly from the wrist band in opposite directions to allow such one-handed operation of both the haptic generators 46. The arrangement of the buttons 941 also results in the user additional applying pressure directly toward the acupressure points P6, SJ5 to further provide therapy to the user. In some versions, the buttons 941 may be touch sensors (e.g., capacitive sensors) that operate in the same manner as the momentary contact switches and only operate the haptic generators 46 when touched.

Figure 36:
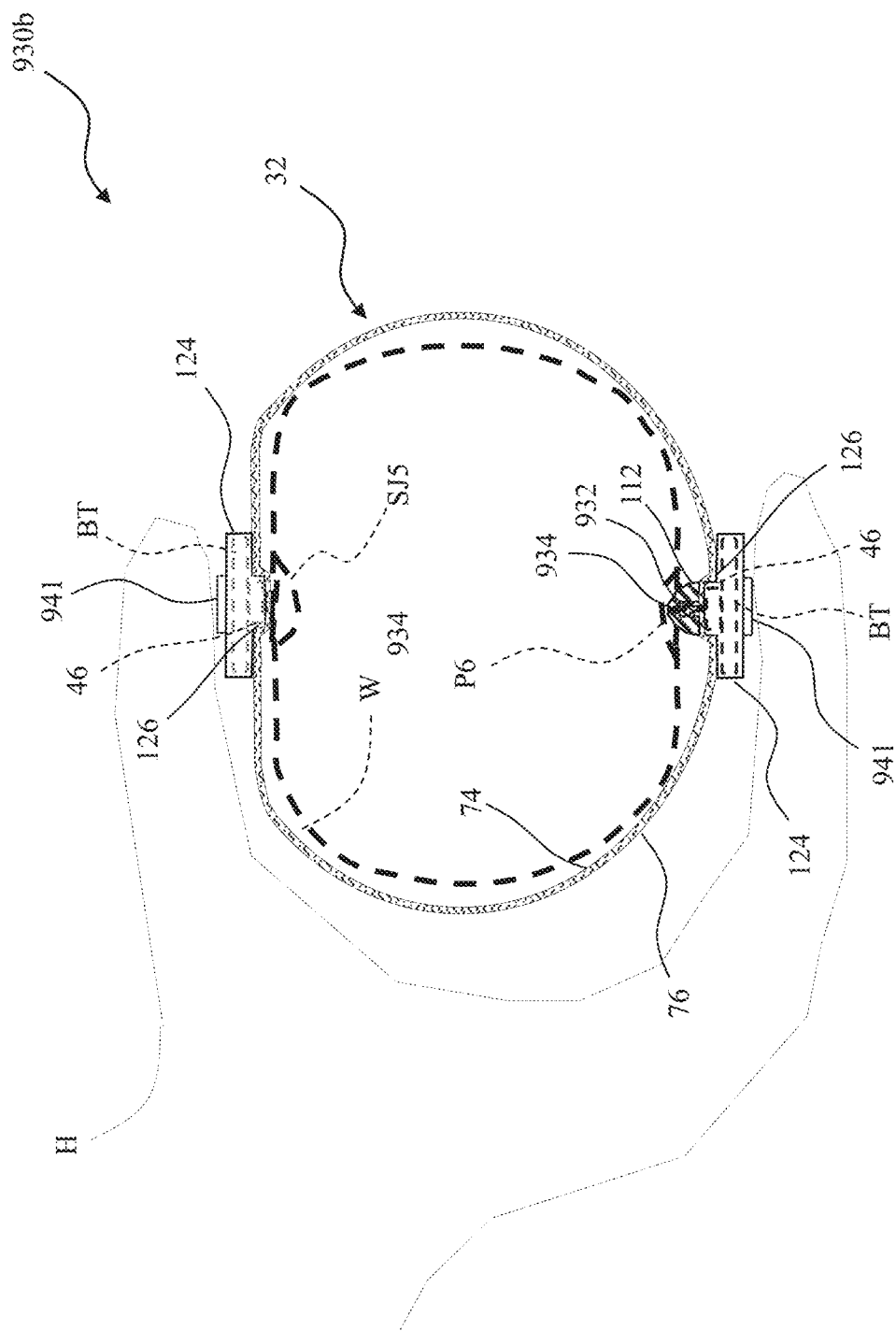
FIG. 36 is a cross-sectional view of a wearable device including a wrist band and two haptic generators being placed against acupressure points of the user during therapy.

FIG. 36 shows another wearable device 930b, similar to the wearable device 930a, but in this case the components used to treat the acupressure point SJ5 lacks the projection 112 and post 932. In this version, the enclosure 126 acts like the projection 112, albeit less pronounced than the projection 112. In some versions the enclosure 126 is removed and the housing 124 has a relatively flat or arcuate wall that engages the wrist band in this location. In the various versions of wearable devices shown herein for use with the user's wrist W, two such devices may be employed, one for each wrist W of the user.

Figure 37:
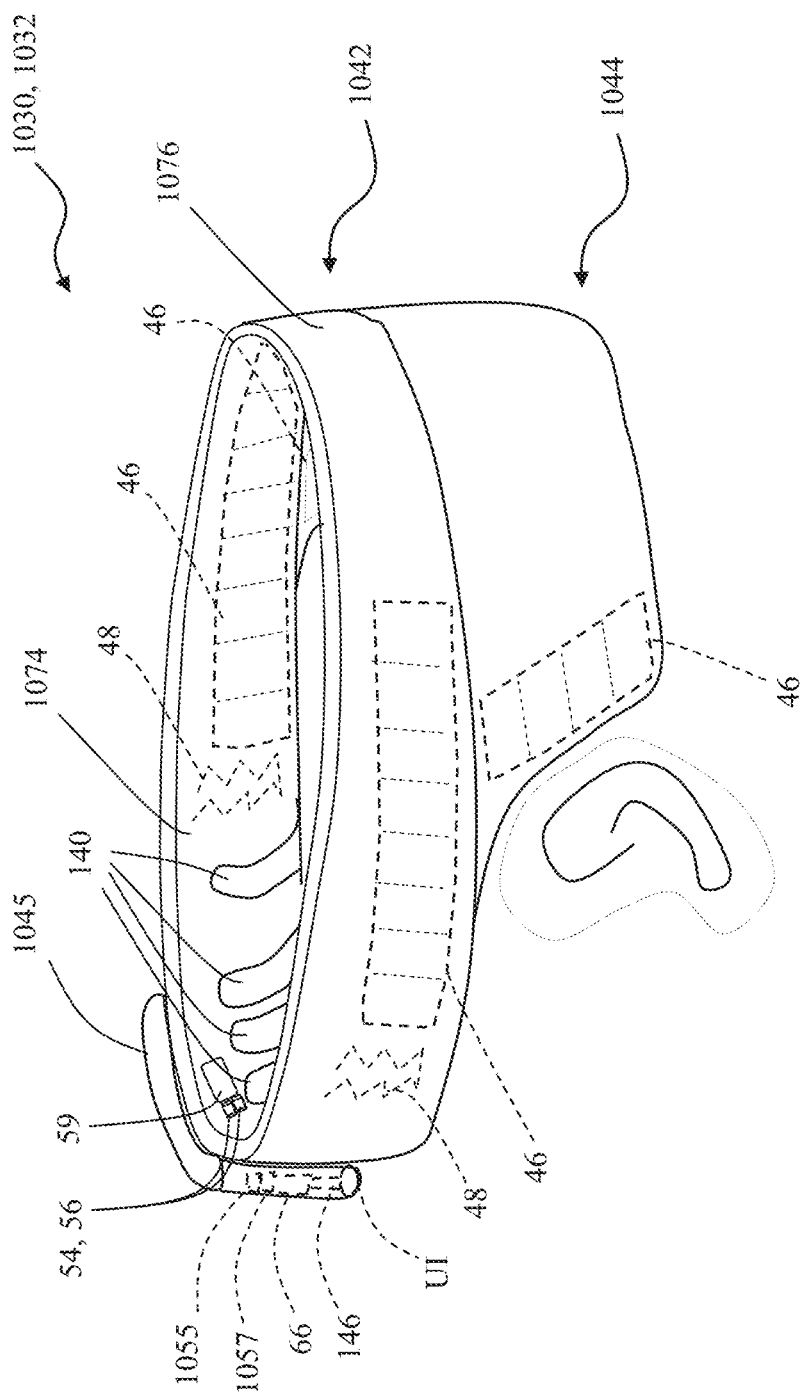
FIG. 37 is a perspective view of a wearable device including a head band.

FIG. 37 illustrates another wearable device 1030 comprising haptic generators 46, thermal elements 48, optical sensors 54, light emitting diodes 56, temperature sensor 59, and EEG sensors 140 (other sensors as previously described may also be present). The EEG sensors 140 are integrated into a wearable support 1032 in the form of a headband 1042. In this version, the headband 1042 completely encircles the head of the user. The headband 1042 may be formed of elastic, semi-elastic, and/or inelastic material and may be formed of plastic, fabric, non-woven fabric, woven fabric, neoprene, and/or any other suitable materials. The headband 1042 includes one or more earpieces 1044 (one shown) that extend downwardly from a main portion of the headband 1042 to extend behind the user's ear. There are one or more haptic generators 46 mounted to the main portion of the headband 1042 extending from the user's temple to the back of the user's ear and one or more haptic generators 46 extending downwardly behind the ear of the user. Two strips of piezoelectric material are shown, but several strips may be present or separate haptic generators like those shown in FIG. 24. The haptic generators 46 are mounted to the main portion of the headband 1042 and the earpiece 1044 to be positioned against a side of the user's head adjacent to their ears and acupressure points surrounding the user's ear. In some versions, the headband 1042 is formed of two or more layers of flexible material 1074, 1076, much like flexible layers 74, 76 and the haptic generators 46 are located between the flexible layers 1074, 1076. The haptic generators 46, thermal elements 48, optical sensors 54, light emitting diodes 56, and other sensors (not shown) can be used as previously described. Additionally, the controller 66 may be integrated into a forehead housing 1045 and a port 146 (USB, USB-C, etc.) may be used to connect the wearable device 1030 (may be present on any of the wearable devices) to a computer. The housing 1045 is connected to the headband 1042 via a releasable connection, including one or more magnetic connections, snaps, hook and loop fasteners, or any other suitable connection. The housing 1045 may also be fixed to the headband 1042 in some versions, such as by fasteners, adhesive, or the like. A user interface UI including one or more user input devices may also be located on the housing 1045 to operate the wearable device 1030 and the housing 1045 may include other sensors, such as one or more accelerometers 1055, gyroscopes 1057, magnetometers, or the like to detect positions, velocities, and/or accelerations of the wearable device 1030 in one or more degrees of freedom.

In this version, the EEG sensors 140 additionally measure one or more brainwaves (see FIG. 25) of the user and can determine whether the user is in a relaxed state or a state of elevated stress or anxiety. During therapy, the haptic generators 46 can be activated in sequence, e.g., from front to back, to provide therapy to the user. The sequence may include at least one haptic generator 46 being active at all times to generate haptic output, or there may be pauses between activation of the next haptic generator 46 in the sequence. Possible sequences may also include waves of activation, e.g., repeated activation of the haptic generators 46 from front to back, back to front, combinations thereof, and the like. These patterns may be utilized for purposes of training and therapy, as previously described, or for other purposes. The controller 66 may be configured to activate the plurality of haptic generators 46 in a predetermined sequence in which two or more of the plurality of haptic generators 46 are activated at different levels, at different times, or at different levels and different times. Activation of the haptic generators 46 may also replicate a therapist following a meridian of the user by sequentially activating (and deactivating) the haptic generators 46 to mimic a therapist's finger tracing around the user's ear as shown in the illustration of FIG. 25A to follow the user's meridians, such as the triple warmer meridian TWM (also referred to as San Jiao meridian/channel). Such activation and deactivation may occur one time or a plurality of times over the duration of therapy.

Figure 40:
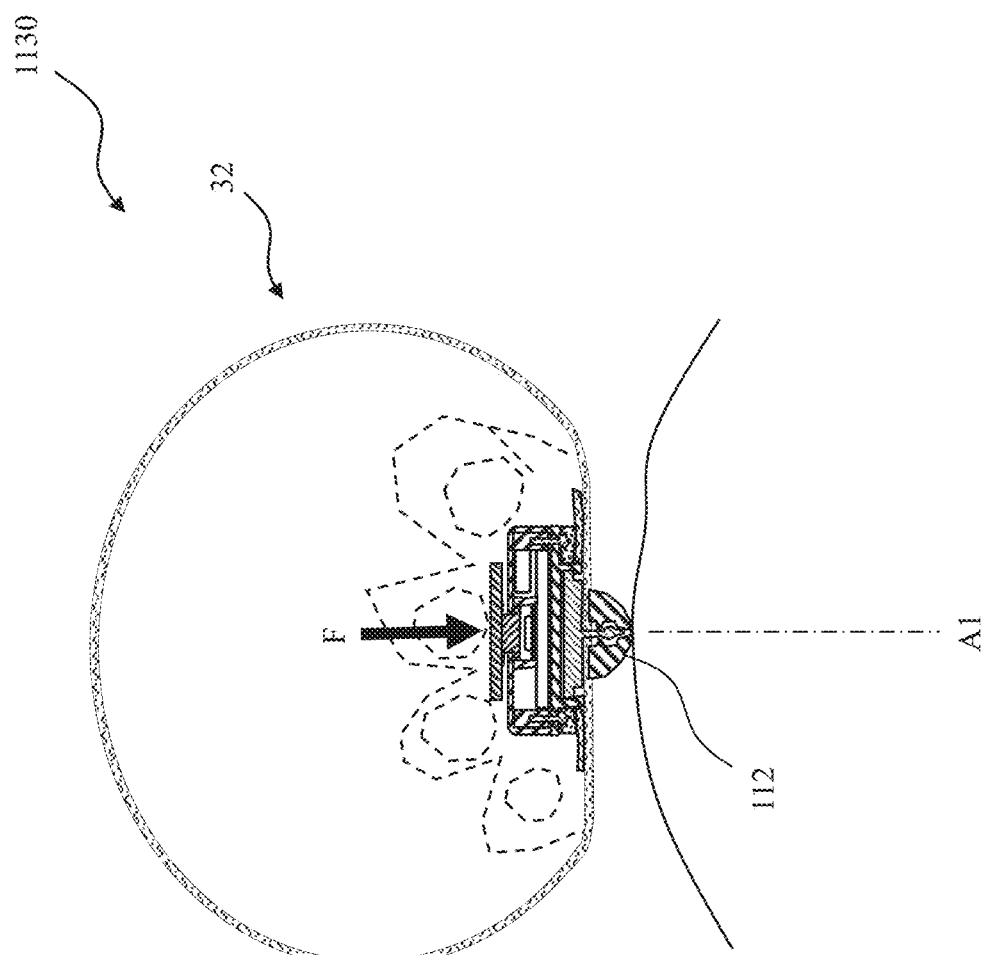
FIG. 40 is a cross-sectional view illustrating the wearable device of FIG. 38 being reversible (inside-out) so that the projection is able to treat other anatomical sites of the user.

FIGS. 38-40 illustrate another wearable device 1130 that comprises the wearable support 32 and one or more haptic generators 46 (only one haptic generator 46 in the version shown). The wearable support 32 includes a wrist band formed of one or more flexible layers 74, 76 (only one layer 74 in the version shown) that completely encircles the user's wrist that may be elastic, semi-elastic, inelastic, combinations thereof, or the like, and able to stretch or be adjusted to fit to most users. In the version shown, the wrist band is formed of elastic fabric that is cut in a single strip and its ends sewn together as shown. The haptic generator 46 is electrically connected to a battery BT (e.g., a coin cell battery or other form of battery BT) via a momentary contact switch 1140 to provide therapy to the user, such as providing one or more of the haptic therapies previously described. The momentary contact switch 1140 may be a micro tactile switch, for example, and may be activated by an integrated button or by a separate button, such as the button 1141 shown. The haptic generator 46 may be activated to generally vibrate against the acupressure point P6, other acupressure points, or other anatomical sites to calm the user, provide nausea relief, or the like.

In this version, the haptic generator 46, battery BT, and momentary contact switch 1140 are substantially enclosed in a housing 124 releasably coupled to the wrist band. In some versions, the housing 124 is formed of plastic and may be compact in size, e.g., just sized slightly larger than the battery BT. In the version shown, the housing 124 has a thickness T of 0.5 inches or less and a maximum length/width dimension of 1.5 inches, e.g., diameter D (see FIG. 39A). In some versions, the thickness is from 0.2 to 0.5 inches, from 0.2 to 0.4 inches, or the like, and the maximum length/width dimension is from 0.6 to 1.5 inches, from 0.6 to 1.0 inches, or the like. The housing 124 includes a housing base 124a with a bottom and a wall extending upwardly therefrom to form a chamber for the electronic components and a housing top 124b connected to the housing base 124a (e.g., via one or more fasteners such as screws or bolts, via snap-fit, via welding or adhesive, combinations thereof, etc.). The chamber is shaped and sized to receive the battery BT, which in this version may be a coin cell battery.

In some versions, the haptic generator 46 may be attached to the housing 124 and exposed outside of the housing 124 to be in direct contact with the user when the wearable support 32 is worn by the user. In some versions, the haptic generator 46 may be captured between flexible layers 74, 76 such that vibrations from the haptic generator 46 are able to be felt/sensed by the user. In some versions, a band tensioner 128, described above can be employed to first tighten the wrist band about the user's wrist W to a predetermined tension (which can be measured by any suitable pressure sensor, strain gauge, or the like connected to the controller 66). Thereafter, the haptic generator 46 can be activated for therapy.

A projection 112 in the form of a massage head, such as a separate dome-shaped cap, extends from the wrist band to apply pressure on the acupressure point P6 of the user's wrist W when the wrist band is worn by the user and properly positioned so that the projection 112 is applying pressure to the acupressure point P6. The projection 112 may be spherically-shaped, hemi-spherically shaped, or have any suitable shape for engaging the user's skin. The projection 112 may have a smooth portion 115 (arcuate, flat, or the like) that is located to engage the user's skin. In some versions, multiple projections 112 may be provided to engage the user's skin. The projection 112 may be substantially rigid compared to the wrist band, and be formed of plastic, such as high-density polyethylene (HDPE), polystyrene (PS), polyethylene terephthalate (PET), or the like. In some cases, a layer, such as a soft fabric layer, silicone layer, a low friction coating layer (e.g., Teflon), etc. may be placed over the projection 112 to act as a skin interface between the projection 112 and the user's skin. The projections 112 may be connected to the wrist band and/or the housing 124 in any suitable manner, including welding, adhesive, fasteners, sewing, heat staking, or the like.

In the version shown in FIGS. 38-40, a post 1132 extends upwardly from a base 1126. The post 1132 is fixed to the base 1126 (e.g., integrally formed therewith). An enlarged portion 1134, such as a spherical shaped-portion, bulbous portion, etc. is connected to the post 1132 and is sized to fit through an opening 1136 in the projection 112 in a snap-fit manner. The opening 1136 is formed by a radially inwardly projecting flange 1137 that is flexible to yield during snap-fit engagement. The enlarged portion 1134 is slightly larger than the opening 1136 to retain the post 1132 once the snap-fit connection is made. The haptic generator 46, during operation, causes vibration of the post 1132 and/or the enlarged portion 1134 to vibrate the one or more projections 112 to provide haptic therapy to the acupressure point P6.

When the projection 112 is connected to the base 1126 and post 1132 (see also FIG. 39A), the flexible layer 74 is captured (trapped) between the projection 112 and the base 1126. The post 1132 and the enlarged portion 1134, which may be integrally formed together, are sized to fit through a hole or opening formed in the flexible layer 74 to secure the projection 112 to the flexible layer 74. Such hole/opening may be formed separately or may be present in the flexible layer 74, such as when the flexible layer 74 is woven. The projection 112 and base 1126 can be connected to the housing 124 in any suitable manner, e.g., snap-fit, press-fit, fasteners, adhesive, or the like to connect the projection 112 and/or the housing 124 to the flexible layer 74. Variations for connecting the housing 124 and the one or more projections 112 to the wrist band are also contemplated.

In the version shown, the housing 124, and specifically the housing top 124b, has a first coupling interface that is shaped to releasably engage a second coupling interface of the base 1126. The coupling interfaces may include any form of coupling elements to secure the housing 124 to the wrist band. In the version shown, the first coupling interface includes one or more first snap elements 1160 and the base 1126 includes one or more second snap elements 1162. The snap elements 1160, 1162 are shaped to engage one another in a snap-fit manner to releasably couple the housing 124 to the wrist band. In the version shown, the first snap elements 1160 include four detent fingers having snap-fit heads and the second snap element includes a flange of the base 1126 engageable by the four detent fingers (compare FIGS. 39A and 39B to see the snap-fit engagement process and FIG. 39C that shows the engagement). Additionally, or alternatively, the wrist band includes one or more hook-and-loop-type fasteners 1164 and the housing, specifically the housing top 124b, includes one or more hook-and-loop-type fasteners 1166 configured to releasably engage the one or more hook-and-loop-type fasteners 1164 of the wrist band when releasably coupling the housing 124 to the wrist band. The hook-and-loop-type fasteners 1164, 1166 may be attached to the wrist band and the housing top 124b, respectively, by any suitable method, including being sewn, fastened, welded, adhered, etc. When the housing 124 is disengaged from the wrist band, then the wrist band remains useable for providing nausea relief to the user via the projection 112. Thus, the releasable nature of the housing 124 provides additional flexibility in use of the wrist band.

In the version shown in FIGS. 38-40, the housing 124 has a top (part of the housing top 124b) and an opposing bottom (part of the housing base 124a). The button 1141 is located on the bottom such that when the user applies force to the button 1141 to operate the haptic generator 46, the force is directed toward the projection 112 to further press the projection 112 into the acupressure point Pericardium 6 of the user. In other words, a center of the button 1141 and a center of the projection 112 are generally aligned along an axis A1 that passes through the acupressure point Pericardium 6 so that any pressure applied onto the button 1141 is directed through the housing 124, through the base 1126 and the projection 112, and to the acupressure point Pericardium 6 to further enhance the therapy to the user. In some versions, the button 1141 is smaller and located on a side of the housing base 124a, extending from the wall of the housing base 124a.

As shown in FIG. 40, the wrist band is reversible so that the projection 112 protrudes outwardly away from the wrist band so that the user is able to apply the projection 112 to other anatomical sites while the one or more haptic generators 46 produce vibrations through the projection 112 to the other anatomical sites. This further enhances haptic therapy that can be provided to the user by allowing the user to apply the projection 112 to other acupressure points on the user, or other locations of tension to treat those locations, e.g., via vibration massage. The user can apply such pressure by placing one or more fingers through the wrist band to engage the housing 124 and press the button 1141 and housing 124 in the direction of the projection 112, as shown, to further apply force through the projection 112 (e.g., massage head) onto the patient's treatment area. The user can also hold/grip the housing 124 to move the housing 124 and thereby move the projection 112 in small circles to massage any areas of interest while simultaneously operating the haptic generator 46 to provide haptic therapy. In some versions, such as when the button 1141 operates a momentary contact switch, operation of the haptic generator 46 stops when the user ceases applying pressure on the button 1141 (by virtue of the spring force of the momentary contact switch opening the circuit).

Figure 41:
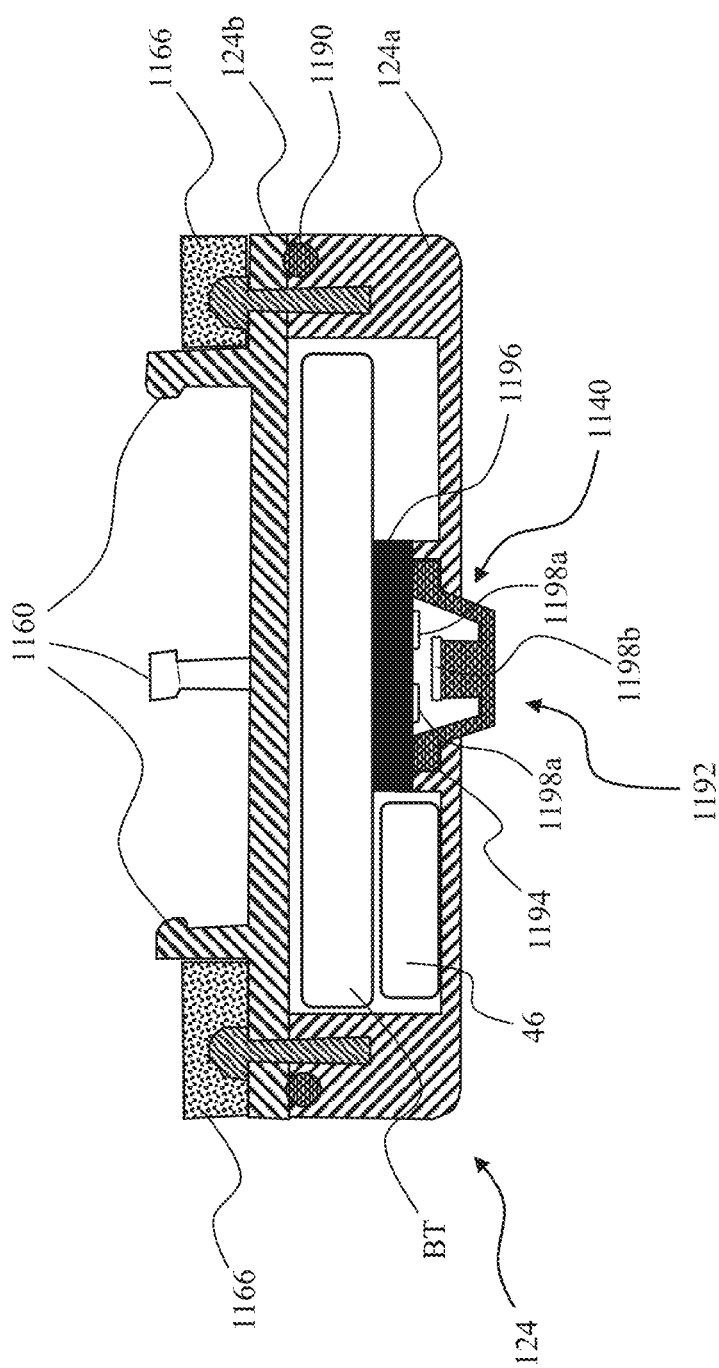
FIG. 41 is a cross-sectional view illustrating a waterproof housing.
Figure 42:
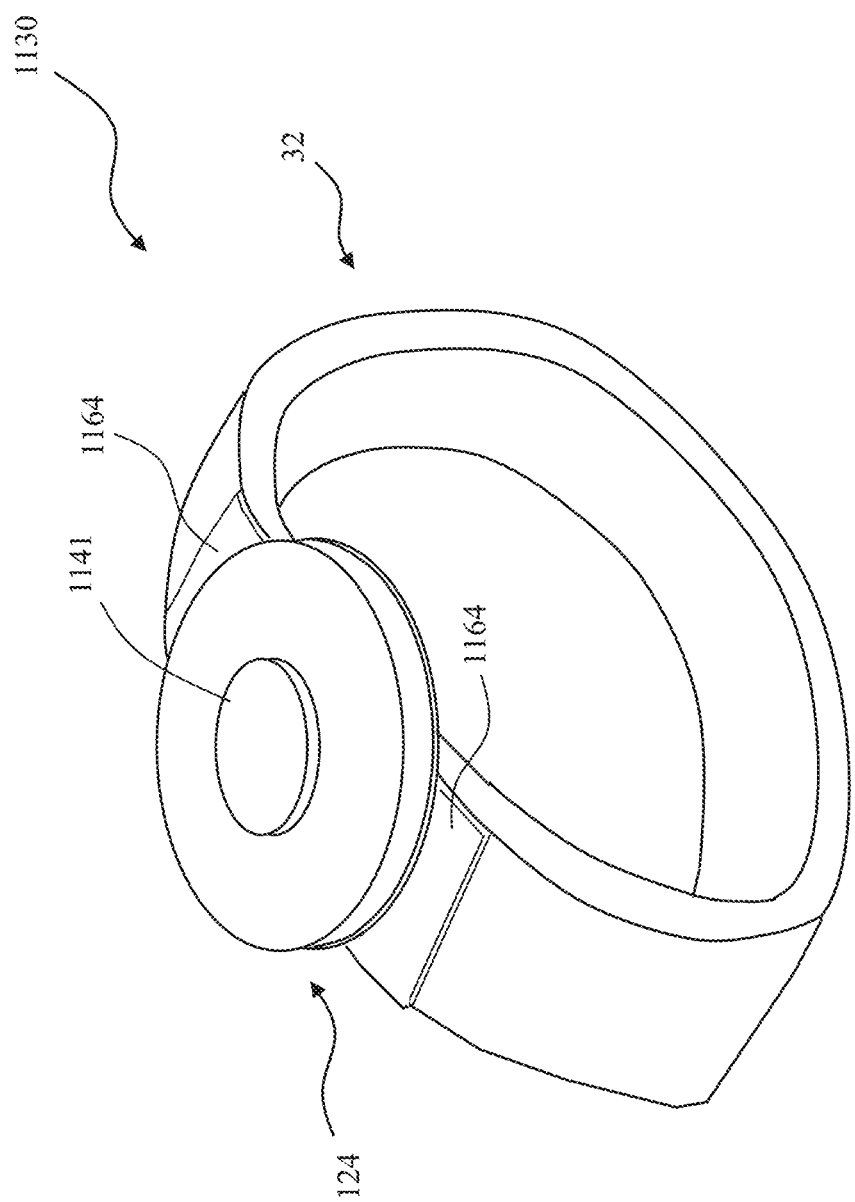
FIG. 42 is a bottom perspective view of the wearable device of FIG. 38.

Referring to FIG. 41, a waterproof (or at least water resistant) version of the housing 124 is shown. In this version, the housing 124 is generally cylindrical in shape. A seal 1190 (e.g., o-ring, gasket, etc.) is located in an annular groove in the housing base 124a to seal against the housing top 124b when the housing top 124b is connected to the housing base 124a. In this version, the button 1141 is a silicone rubber button 1192 with integrally formed gasket 1194 that is captured between the bottom of the housing base 124a and a printed circuit board 1196. The button 1141 may also be centrally located on the bottom of the housing 124 and have a cylindrical shape as well, such that the housing 124 and button 1141 are disposed about the axis that passes normal to the wrist band and through the acupressure point P6 and the housing 124 and the button 1141 extend radially equidistantly from the axis. As a result, the housing 124 and the button 1141 appear to the user to be in the same position relative to the wrist band regardless of their actual orientation relative to the wrist band (see, e.g., FIG. 42). The gasket 1194 acts as a seal to further inhibit liquids, such as water, from intruding into the housing 124 through an opening formed in the bottom for the silicone rubber button 1192. The printed circuit board 1196 includes spaced apart contacts 1198a forming part of the momentary contact switch. A moving contact 1198b is mounted on the silicone rubber button 1192 (e.g., via adhesive, insert molding, etc.) and moves toward and makes contact with the contacts 1198a when the silicone rubber button 1192 is depressed to complete the circuit operating the haptic generator 46. The silicone rubber button 1192 includes webs/walls that are resilient to return the silicone rubber button 1192 to its normal position with the moving contact 1198b spaced from the contacts 1198a when released.

Figure 43:
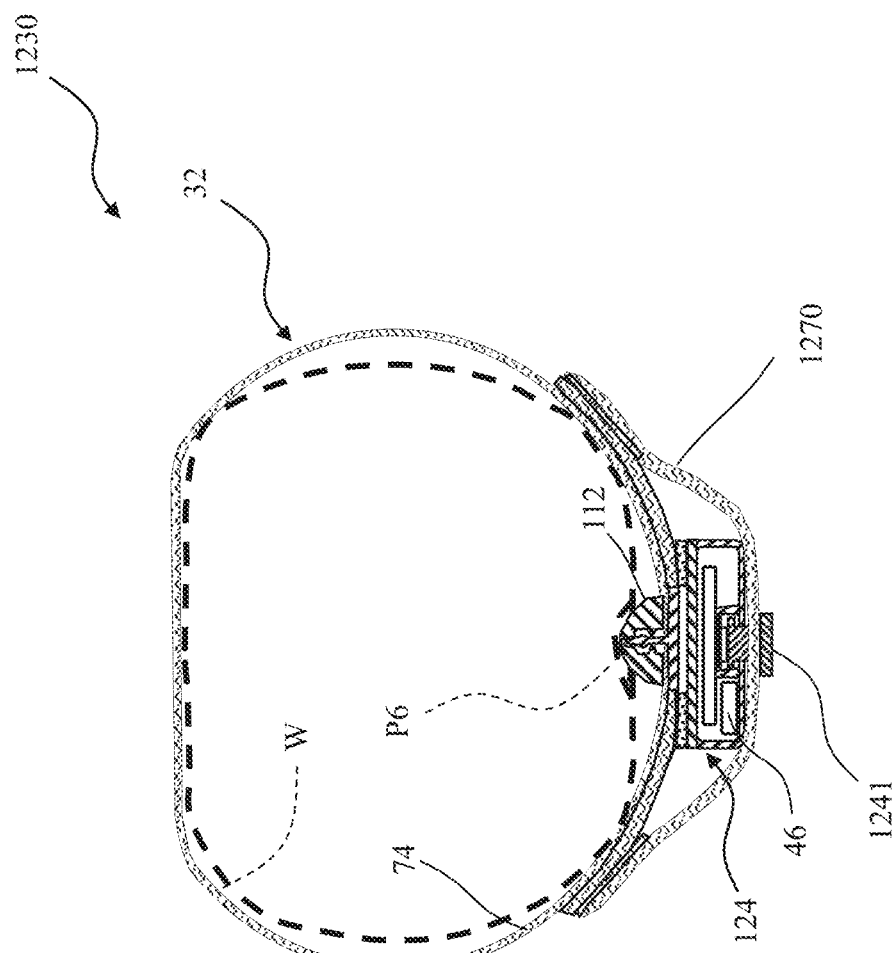
FIG. 43 is a cross-sectional view of a wearable device including a wrist band and a haptic generator for being placed against an acupressure point of a user during therapy, wherein the haptic generator is located in a housing that is attached to a separate band that is releasably attachable to the wrist band.

FIG. 43 illustrates another wearable device 1230 that comprises the wearable support 32 and a haptic generator 46. This version is similar to the version shown in FIGS. 38-40 except that the housing 124 is mounted to a separate strap 1270 and the separate strap 1270 is then fastened to the wrist band via one or more hook-and-loop-type fasteners, adhesive, welding, or the like. In this version, the separate strap 1270 may be releasably fastened to the wrist band to supplement the wrist band with haptic therapy, while also allowing the wrist band and the projection 112 to be separately used for nausea relief, for example. In the version shown, separate hook-and-loop-type fasteners are mounted to the wrist band and the separate strap 1270. The separate strap 1270 may be formed of the same materials as the flexible layer 74. The button 1241 may also be located beneath the separate strap 1270 or on one side of the separate strap 1270 opposite the housing 124, as shown.

Figure 44A:
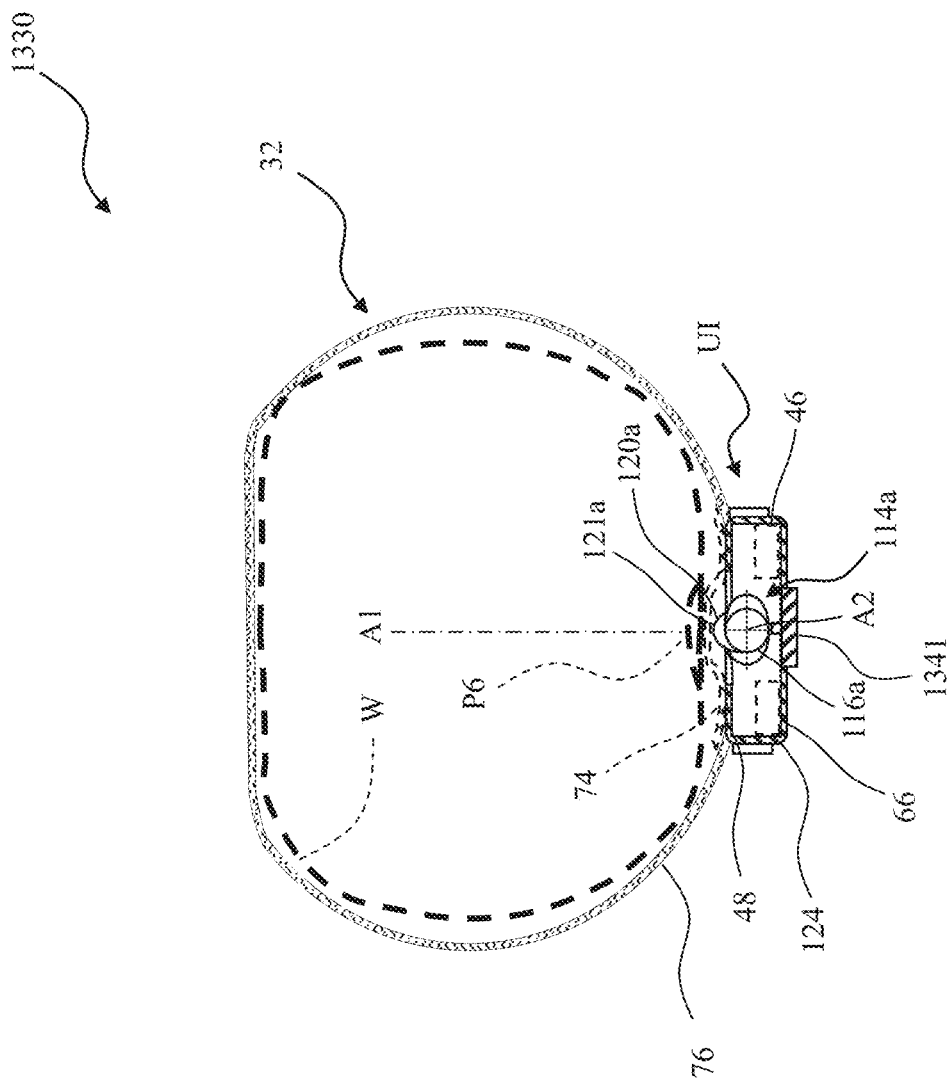
FIG. 44A is a cross-sectional view of a wearable device with a cam in a treatment position.
Figures 44B, 45:
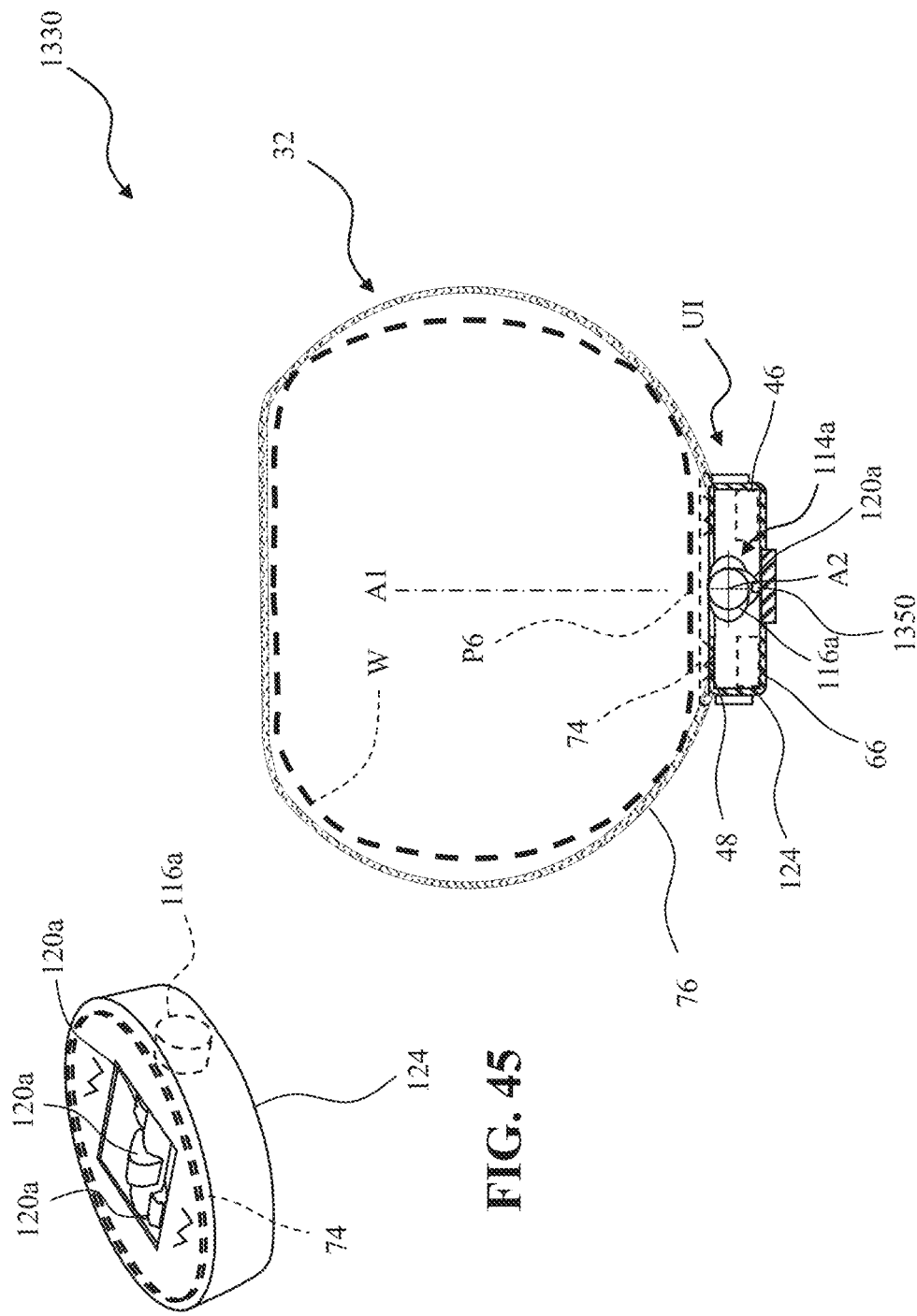
FIG. 44B is a cross-sectional view of the wearable device of FIG. 44A with the cam in a home position.
FIG. 45 is a perspective view of a housing of the wearable device of FIG. 44A illustrating an arrangement of cams to be rotated for treatment.

FIGS. 44A-45 illustrate a variation of the wearable device 1330 that employs a rotary actuator 114a to apply pressure to the acupressure point P6 of the user and/or to other treatment sites. In some versions, a linear actuator, and/or other form of actuator could be employed. The rotary actuator 114a is connected to the controller 66 to be activated by the controller 66. The rotary actuator 114a is mounted to a rigid housing 124. The housing 124 is attached and fixed to the first and/or second flexible layer 74, 76 using any attachment method as previously described, or any suitable attachment method. The rotary actuator 114a comprises a motor 116a (e.g., a 3V, reversible DC motor or other suitable motor) that is mounted to the housing 124 and one or more rotationally-movable cams 120a connected to a drive shaft of the motor 116a to rotate relative to the housing 124 about axis A2. As shown in FIG. 45, the drive shaft of the motor 116a is effectively a cam shaft having the one or more cams 120a fixed thereto to protrude into and out of the housing 124 through an opening 124c in the housing 124 during rotation of the drive shaft. A transmission may also be coupled to the motor 116a with the cam shaft being an output shaft from the transmission.

During actuation of the rotary actuator 114a, as shown in FIG. 44A, each of the one or more cams 120a has a cammed portion 121a that rotates toward the acupressure point P6 or other treatment site to apply pressure. In some versions, the motor 116a rotates in full 360-degree rotations to rotate the one or more cams 120a. In some versions, the motor 116a oscillates back and forth without making a full rotation (e.g., rotating less than 360 degrees). The one or more cams 120a may be located underneath flexible material of the wearable support 32 (e.g., under flexible layer 74) to protrude into the flexible material to apply pressure to the treatment area. The motor 116a may rotate from 1 to 1000 rotations per minute (RPM), from 10 to 100 rotations per minute, from 10 to 60 rotations per minute, or the like. In some versions, the wearable device 1330 further includes a haptic generator 46 to additionally provide vibrations to the one or more cams 120a during actuation. The haptic generator 46 may operate as previously described.

The user interface UI of the wearable device 1330, which is coupled to the controller 66, may include a button 1341 of a momentary contact switch as previously described that is pressed to activate the motor 116a and/or the haptic generator 46. In some versions, the user interface UI includes an on/off switch and maintains the wearable device 1330 in an active state when depressed once and then deactivates the wearable device 1330 when depressed a second time. Any suitable form of switch may be used to activate/deactivate the motor 116a and/or the haptic generator 46. Heat may also be applied to the user via one or more thermal elements 48 coupled to the controller 66 that can be activated in response to input from the user (e.g., separate buttons to activate heat and possibly at different temperature settings).

In some versions, the controller 66 is configured to rotate the one or more cams 120a to a home position in response to user actuation of a home button of the user interface UI, or the controller 66 may automatically place the one or more cams 120a in the home position when the wearable device 1330 is deactivated. The home position is a position in which none of the cams 120a are protruding out of the housing 124 through the opening 124c in the housing 124 such that the cams 120a are no longer applying pressure against the user's skin. In this state, the wearable device 1330 operates as a conventional wrist band. The home position may be such that one of the cams 120a is directed downward in the housing 124 and may be signaled by activation of a limit switch 1350 that is coupled to the controller 66 to provide a signal to the controller 66 when the cams 120a are in their home position (see FIG. 44B). This allows the user to actively wear the wearable device 1330 on their wrist W without any pressure being applied to their wrist W.

In some versions, the controller 66 is configured to place one of the cams 120a in contact with the acupressure point P6 and keep the cam 120a in that treatment position (e.g., fully up position) until instructed otherwise (see FIG. 44A). This may be controlled by another button of the user interface UI that indicates nausea relief is desired—in which case the cam 120a that is kept in contact with the acupressure point P6 acts to provide such relief. Another button (or the same button) may be actuated by the user to start massage therapy by causing the one or more cams 120a to begin rotating at their normal operational speed. The user interface UI may also provide speed control settings, such as high, medium, or low speeds, as desired by the user. One or more buttons of the user interface UI may be associated with such speed control settings (e.g., one button depressed one or more times to toggle through speed control, one button for each speed setting, etc.). The wearable device 1330 of FIGS. 44A-45 is also reversible, similar to the wearable device 1130 shown in FIG. 40 and can therefore also be used to provide massage therapy to the user in a similar manner.

The terms "comprise", "comprises," and "comprising", "has", "have", and "having", "include", "includes", and "including" are open-ended linking verbs. For instance, a system, device, or apparatus, or element thereof, that "comprises," "has," or "includes" one or more elements possesses those one or more elements, but is not limited to possessing only those one or more elements.

Numerous wearable devices are disclosed herein with various combinations of therapy devices for providing therapy to the user and/or measuring devices for measuring physiological parameters of the user. It should be appreciated that other wearable devices are also contemplated that include one or more of these therapy devices, one or more of these measuring devices, or combinations thereof, even though not described in detail. It should also be appreciated that any one or more of the various therapy devices described can be used in combination with any one or more of the various measuring devices to form additional wearable devices.

What is claimed is:

1. A wearable device for providing pressure therapy to a user, the wearable device comprising:
   a wearable support to be worn by the user, wherein the wearable support includes an outer layer and a plurality of inflatable regions capable of being separately inflated;
   a pump operatively coupled to the plurality of inflatable regions to inflate the plurality of inflatable regions;
   an inflator housing attached to the outer layer of the wearable support, wherein the inflator housing has a base and a lid to enclose the pump inside the inflator housing so that the pump is mounted to the wearable support;
   a plurality of conduits to fluidly connect the pump to the plurality of inflatable regions, wherein the plurality of conduits extends through the lid of the inflator housing and through the outer layer to the plurality of inflatable regions;
   a plurality of valves operable to open and close fluid communication between the pump and the plurality of inflatable regions such that the plurality of inflatable regions can be separately inflated;
   a controller coupled to the pump to control operation of the pump to inflate the plurality of inflatable regions, wherein the controller is operable to inflate and deflate the plurality of inflatable regions in a repeated pattern to provide the pressure therapy; and
   a display housing carrying a user interface and a display, wherein the display housing is separate from the inflator housing and is coupled to the wearable support such that, when the wearable support is worn by the user, the display housing is located adjacent a top of the wearable support and the inflator housing is located on a bottom of the wearable support and extends from the bottom of the wearable support.

2. The wearable device of claim 1, wherein the lid has an upper surface that interfaces with the outer layer of the wearable support on the bottom of the wearable support.

3. The wearable device of claim 1, further comprising one or more sensors to monitor one or more physiological parameters of the user, wherein the controller is configured to control inflation of the plurality of inflatable regions based on values of the one or more physiological parameters.

4. The wearable device of claim 1, further comprising a sensor to monitor a heart rate of the user, wherein the controller is configured to control inflation of the plurality of inflatable regions based on the heart rate of the user.

5. The wearable device of claim 1, further comprising a sensor coupled to the wearable support to monitor a heart rate of the user, wherein the plurality of inflatable regions includes a first inflatable region and the sensor is arranged relative to the first inflatable region such that inflation of the first inflatable region causes movement of the sensor toward the user.

6. The wearable device of claim 1, further comprising one or more thermal elements connected to the controller to provide thermal therapy to the user.

7. The wearable device of claim 1, further comprising one or more vibration motors coupled to the wearable support, wherein the controller is operable to generate vibrations with the one or more vibration motors to be felt by the user and that mimic a breathing pattern for the user.

8. The wearable device of claim 7, wherein the controller is configured to operate the one or more vibration motors to mimic the breathing pattern in a manner that differentiates between inhaling and exhaling phases of breathing.

9. The wearable device of claim 7, wherein the controller is configured to operate the one or more vibration motors to mimic the breathing pattern in a manner that prescribes inhaling for five seconds and exhaling for five seconds.

10. The wearable device of claim 7, wherein the controller is configured to operate the one or more vibration motors to mimic the breathing pattern in a manner that differentiates between inhaling and exhaling phases of breathing by activating and deactivating the one or more vibration motors.

11. The wearable device of claim 1, wherein the user interface includes a button and the display is a light emitting diode (LED) display.

12. The wearable device of claim 1, further comprising one or more light sources coupled to the controller and arranged to emit light on the user.

13. The wearable device of claim 1, wherein the plurality of inflatable regions are defined by a plurality of bladder layers.

14. The wearable device of claim 1, further comprising a power cable extending from the display housing into the wearable support.

15. The wearable device of claim 1, wherein the wearable support is a wrist band.

16. The wearable device of claim 1, wherein the plurality of valves is a plurality of solenoid valves.

17. The wearable device of claim 1, further comprising a pressure sensor connected to the controller, wherein the controller is operable to inflate the plurality of inflatable regions to different pressures during the pressure therapy.

18. The wearable device of claim 1, wherein the plurality of inflatable regions includes a first inflatable region and a second inflatable region.

19. A wearable device for providing pressure therapy to a user, the wearable device comprising:
- a wearable support to be worn by the user, wherein the wearable support includes an outer flexible layer and a plurality of bladder layers defining a plurality of inflatable regions capable of being separately inflated;
- a pump operatively coupled to the plurality of inflatable regions to inflate the plurality of inflatable regions;
- an inflator housing attached to the outer flexible layer of the wearable support, wherein the inflator housing has a base and a lid to enclose the pump inside the inflator housing so that the pump is mounted to the wearable support, and wherein the lid has an upper surface interfacing with the outer flexible layer;
- a plurality of conduits to fluidly connect the pump to the plurality of inflatable regions, wherein the plurality of conduits extends through the lid of the inflator housing and through the outer flexible layer to the plurality of inflatable regions;
- a plurality of valves operable to open and close fluid communication between the pump and the plurality of inflatable regions such that the plurality of inflatable regions can be separately inflated;
- a controller coupled to the pump to control operation of the pump to inflate the plurality of inflatable regions, wherein the controller is operable to inflate and deflate the plurality of inflatable regions in a repeated pattern to provide the pressure therapy;
- a display housing carrying a user interface and a display, wherein the display housing is separate from the inflator housing and is coupled to the wearable support such that, when the wearable support is worn by the user, the display housing is located adjacent a top of the wearable support and the inflator housing is located on a bottom of the wearable support and extends from the bottom of the wearable support; and
- a power cable extending from the display housing into the wearable support.

20. A wearable device for providing pressure therapy to a user, the wearable device comprising:
- a wearable support to be worn by the user, wherein the wearable support includes an outer layer, an inner layer, and a plurality of inflatable regions capable of being separately inflated;
- a pump to inflate the plurality of inflatable regions;
- a plurality of conduits to fluidly connect the pump to the plurality of inflatable regions, wherein the plurality of conduits extends through the outer layer to the plurality of inflatable regions;
- a plurality of valves operable to open and close fluid communication between the pump and the plurality of inflatable regions such that the plurality of inflatable regions can be separately inflated;
- a controller coupled to the pump to control operation of the pump to inflate the plurality of inflatable regions, wherein the controller is operable to inflate and deflate the plurality of inflatable regions in a repeated pattern to provide the pressure therapy; and
- a plurality of vibration motors positioned between the inner layer and the outer layer of the wearable support, wherein the controller is operable to control the plurality of vibration motors.

\* \* \* \* \*